United States Patent
Norton et al.

(10) Patent No.: US 9,686,979 B2
(45) Date of Patent: Jun. 27, 2017

(54) PYRETHROID FORMULATIONS

(75) Inventors: Danielle Norton, Toronto (CA); Nikolai Loukine, Toronto (CA); Rachel Gong, Mississauga (CA); Henry Galas, Toronto (CA); Jose Amado Dinglasan, Toronto (CA); Anjan Kumar Das, Oakville (CA); Darren J. Anderson, Toronto (CA)

(73) Assignee: Vive Crop Protection Inc., Toronto, Ontario (CA)

(*) Notice: Subject to any disclaimer, the term of this patent is extended or adjusted under 35 U.S.C. 154(b) by 0 days.

(21) Appl. No.: 14/240,222

(22) PCT Filed: Aug. 23, 2012

(86) PCT No.: PCT/IB2012/002832
§ 371 (c)(1),
(2), (4) Date: Feb. 21, 2014

(87) PCT Pub. No.: WO2013/041975
PCT Pub. Date: Mar. 28, 2013

(65) Prior Publication Data
US 2014/0187424 A1    Jul. 3, 2014

Related U.S. Application Data

(60) Provisional application No. 61/526,433, filed on Aug. 23, 2011, provisional application No. 61/589,548, filed on Jan. 23, 2012, provisional application No. 61/641,384, filed on May 2, 2012, provisional application No. 61/641,518, filed on May 2, 2012.

(51) Int. Cl.
| | |
|---|---|
| *A01N 53/00* | (2006.01) |
| *A01N 57/20* | (2006.01) |
| *A01N 25/14* | (2006.01) |
| *A01N 25/22* | (2006.01) |
| *C05G 3/02* | (2006.01) |

(52) U.S. Cl.
CPC ............. *A01N 25/14* (2013.01); *A01N 53/00* (2013.01); *A01N 57/20* (2013.01); *C05G 3/02* (2013.01)

(58) Field of Classification Search
None
See application file for complete search history.

(56) References Cited

U.S. PATENT DOCUMENTS

| | | | |
|---|---|---|---|
| 6,596,292 B2 * | 7/2003 | Nishi | A01N 25/08 424/405 |
| 2004/0048833 A1 | 3/2004 | Kohn | |
| 2007/0122436 A1 | 5/2007 | Koltzenburg et al. | |
| 2008/0090886 A1 | 4/2008 | Gottsche et al. | |
| 2008/0138371 A1 | 6/2008 | Amrhein et al. | |
| 2008/0213326 A1 * | 9/2008 | Amrhein et al. | 424/405 |
| 2010/0016443 A1 | 1/2010 | Toledano et al. | |
| 2010/0210465 A1 | 8/2010 | Li et al. | |
| 2012/0214857 A1 * | 8/2012 | Reinhard | A01N 25/04 514/407 |
| 2013/0078297 A1 * | 3/2013 | Schlotterbeck | A01N 25/04 424/405 |

FOREIGN PATENT DOCUMENTS

| | | |
|---|---|---|
| CN | 1491541 A | 4/2004 |
| EP | 0183999 A1 | 6/1986 |
| WO | WO-2006/060551 A2 | 6/2006 |
| WO | WO 2010/078852 | 7/2010 |
| WO | WO-2013/014127 A1 | 1/2013 |

OTHER PUBLICATIONS

International Search Report for PCT/IB2012/002832, mailed May 17, 2013, 3 pages.
Written Opinion for PCT/IB2012/002832, mailed May 17, 2013, 8 pages.
European Search Report EP12833626, 3 pages (Mar. 11, 2015).

* cited by examiner

*Primary Examiner* — Alton Pryor
(74) *Attorney, Agent, or Firm* — Choate, Hall and Stewart LLP; Charles E. Lyon; Su Kyung Suh

(57) ABSTRACT

The present disclosure provides formulations of pyrethroid compounds comprising nanoparticles of polymer-associated pyrethroid compounds along with various formulating agents. The present disclosure also provides methods for producing and using these formulations. The disclosure describes various formulations and formulating agents that can be included in the formulations. Additionally, the disclosures describes application to various plants and pests as well as advantages of the disclosed formulations.

24 Claims, 1 Drawing Sheet

PYRETHROID FORMULATIONS

BACKGROUND

Pyrethroid compounds are widely used for the control of insect pests in agricultural areas as well as for structural pest control in urban areas. This class of pesticides is non-systemic and has contact and stomach action. Most pyrethroids act on the nervous system of insects, and disrupt the function of the neurons by interacting with sodium channels. Pyrethroids are highly nonpolar, have low water solubility, low volatility, high octanol-water partition coefficients, and have high affinity for soil and sediment particulate matter. As a result pyrethroids are easily adsorbed to the sediments of natural water systems and have low soil mobility. Pyrethroids in water solution tend to be stable at acid and neutral pH but become increasingly susceptible to hydrolysis under alkaline conditions. Pyrethroids can vary in their susceptibility to sunlight (e.g., see *Rev. Environ. Contam. Toxicol.* 2002; 174:49-170).

Because of their low water solubility, pyrethroids are currently formulated into various usable forms such as emulsifiable concentrates (ECs), liquid concentrate (SL), and suspension concentrates (SC) that use petroleum or non-petroleum based solvents along with anionic and non-ionic emulsifiers and stabilizers. Pyrethroids have also been formulated as water dispersible powders or granules (WPs or WGs) and soluble powders (SP) that use organic or inorganic carriers. These formulations are available as solid or liquid formulations with varying contents of active ingredient (low or high) that can be used as is or after dilution with water. As described below, while these formulations address some of the inherent challenges that are associated with pyrethroids there remains a need in the art for improved pyrethroid formulations.

SUMMARY OF THE INVENTION

The present disclosure provides formulations of pyrethroid compounds comprising nanoparticles of polymer-associated pyrethroid compounds along with various formulating agents. The present disclosure also provides methods for producing and using these formulations.

In various aspects, the present disclosure provides a formulation comprising a nanoparticle comprising a polymer-associated pyrethroid compound with an average diameter of between about 1 nm and about 500 nm; and the polymer is a polyelectrolyte, and a dispersant or a wetting agent.

In some embodiments, the nanoparticle has a diameter of between about 1 nm and about 100 nm. In some embodiments, the nanoparticle has a diameter of between about 1 nm and about 20 nm.

In some embodiments, the formulation includes a plurality of nanoparticles, wherein the nanoparticles are in an aggregate and the aggregate has a diameter of between about 10 nm and about 5000 nm. In some embodiments, the formulation includes a plurality of nanoparticles, wherein the nanoparticles are in an aggregate and the aggregate has a diameter of between about 100 nm and about 2500 nm. In some embodiments, the formulation includes a plurality of nanoparticles, wherein the nanoparticles are in an aggregate and the aggregate has a diameter of between about 100 nm and about 1000 nm. In some embodiments, the formulation includes a plurality of nanoparticles, wherein the nanoparticles are in an aggregate and the aggregate has a diameter of between about 100 nm and about 300 nm.

In some embodiments, the ratio of pyrethroid compound to polymer within the nanoparticles is between about 10:1 and about 1:10 on a w/w basis. In some embodiments, the ratio of pyrethroid compound to polymer within the nanoparticles is between about 5:1 and about 1:5. In some embodiments, the ratio of pyrethroid compound to polymer within the nanoparticles is between about 2:1 and about 1:2. In some embodiments, the ratio of pyrethroid compound to polymer within the nanoparticles is about 1:1. In some embodiments, the ratio of pyrethroid compound to polymer within the nanoparticles is about 5:1. In some embodiments, the ratio of pyrethroid compound to polymer within the nanoparticles is about 4:1.

In some embodiments, the pyrethroid compound is a cyhalothrin. In some embodiments, the pyrethroid compound is lambda-cyhalothrin. In some embodiments, the pyrethroid compound is cypermethrin. In some embodiments, the pyrethroid compound is bifenthrin.

In some embodiments, the polymer in the formulation is selected from the group consisting of poly(methacrylic acid co-ethyl acrylate); poly(methacrylic acid-co-styrene); poly(methacrylic acid-co-butylmethacrylate); poly(ethylene glycol) methyl ether methacrylate; poly(n-butylmethacrylcate-co-methacrylic acid). In some embodiments, the polymer is a homopolymer. In some embodiments, the polymer is a copolymer. In some embodiments, the polymer is a random copolymer.

In some embodiments of the formulation the dispersant and/or wetting agent is selected from the group consisting of lignosulfonates, organosilicones, methylated or ethylated seed oils, ethoxylates, sulfonates, sulfates and combinations thereof. In some embodiments, the dispersant and/or wetting agent is sodium lignosulfonate. In some embodiments, the dispersant and/or wetting agent is a sodium sulfonate. In some embodiments, the dispersant and/or wetting agent is a sodium dodecylbenzene sulfonate. In some embodiments, the wetting agent and the dispersant are the same compound. In some embodiments, the wetting agent and the dispersant are different compounds. In some embodiments, the formulation excludes a wetting agent. In some embodiments, the formulation excludes a dispersant.

In some embodiments, the wetting agent is less than about 30 weight % of the formulation. In some embodiments, the wetting agent is less than about 5 weight % of the formulation. In some embodiments, the dispersant is less than about 30 weight % of the formulation. In some embodiments, the dispersant is less than about 5 weight % of the formulation.

In some embodiments, the formulation is in the form of a high solids liquid suspension.

In some embodiments the formulation includes between about 0.05 weight % and about 5 weight % of a thickener. In some embodiments, the thickener is less than about 1 weight % of the formulation. In some embodiments, the thickener is less than about 0.5 weight % of the formulation. In some embodiments, the thickener is less than about 0.1 weight % of the formulation. In some embodiments, the thickener is selected from the group consisting of guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd, fumes silica and combinations thereof.

In some embodiments the formulation includes between about 0.01 weight % and about 0.2 weight % of a preservative. In some embodiments, the preservative is less than about 0.1 weight % of the formulation. In some embodiments, the preservative is less than about 0.05 weight % of the formulation. In some embodiments, the preservative is selected from the group consisting of tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof.

In some embodiments the formulation includes between about 0.05 weight % and about 10 weight % of an anti-freezing agent. In some embodiments, the anti-freezing agent is less than about 5 weight % of the formulation. In some embodiments, the anti-freezing agent is less than about 1 weight % of the formulation. In some embodiments, the anti-freezing agent is selected from the group consisting of ethylene glycol; propylene glycol; urea and combinations thereof.

In some embodiments the formulation includes water. In some embodiments, the water is less than about 50 weight % of the formulation. In some embodiments, the water is less than about 25 weight % of the formulation. In some embodiments, the water is less than about 10 weight % of the formulation.

In some embodiments, the nanoparticles of polymer-associated pyrethroid compound comprise between about 20 weight % and about 80 weight % of the formulation. In some embodiments, the nanoparticles of polymer-associated pyrethroid compound comprise between about 20 weight % and about 60 weight % of the formulation. In some embodiments, the nanoparticles of polymer-associated pyrethroid compound comprise between about 20 weight % and about 50 weight % of the formulation. In some embodiments, the nanoparticles of polymer-associated pyrethroid compound comprise between about 25 weight % and about 50 weight % of the formulation. In some embodiments, the nanoparticles of polymer-associated pyrethroid compound comprise between about 30 weight % and about 40 weight % of the formulation. In some embodiments, the polymer-associated pyrethroid compound is between about 5 weight % and about 40 weight % of the formulation. In some embodiments, the polymer-associated pyrethroid compound is between about 5 weight % and about 25 weight % of the formulation. In some embodiments, the polymer-associated pyrethroid compound is between about 10 weight % and about 25 weight % of the formulation. In some embodiments, the polymer-associated pyrethroid compound is between about 15 weight % and about 25 weight % of the formulation.

In some aspects the formulation includes a nanoparticle comprising a polymer-associated pyrethroid compound with an average diameter of between about 1 nm and about 500 nm wherein the polymer is a polyelectrolyte, a dispersant or a wetting agent, a thickener, a preservative, an anti-freezing agent and water.

In some aspects the formulation includes a nanoparticle comprising a polymer-associated pyrethroid compound with an average diameter of between about 1 nm and about 500 nm wherein the polymer is a polyelectrolyte, between about 1 weight % and about 30 weight % of a dispersant or a wetting agent, between about 0.05 weight % and about 5 weight % of a thickener, between about 0.01 weight % and about 0.2 weight % of a preservative, between about 0.05 weight % and about 10 weight % of an anti-freezing agent and water.

In some embodiments the formulation is a wettable granule. In some embodiments the formulation includes an inert filler. In some embodiments, the inert filler makes up less than about 90 weight % of the formulation. In some embodiments, the inert filler makes up less than about 40 weight % of the formulation. In some embodiments, the inert filler makes up less than about 5 weight % of the formulation. In some embodiments, the inert filler is selected from the group consisting of saccharides, celluloses, starches, carbohydrates, vegetable oils, protein inert fillers, polymers and combinations thereof.

In some embodiments the wettable granule formulation includes water. In some embodiments, the water is less than about 50 weight % of the formulation. In some embodiments, the water is less than about 25 weight % of the formulation. In some embodiments, the water is less than about 10 weight % of the formulation.

In some embodiments the formulation includes between about 1 weight % and about 20 weight % of a disintegrant. In some embodiments, the disintegrant is selected from the group consisting of polyvinyl pyrrolidone, modified cellulose gum, pregelatinized starch, cornstarch, modified corn starch, sodium carboxymethyl starch, microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides, alkylcelullose, hydroxyalkylcellulose, alginates, dextrans and poly(alkylene oxide), a combination of citric acid or bicarbonate, a combination of ascorbic acid and bicarbonate, lactose, anhydrous dibasic calcium phosphate, dibasic calcium phosphate, magnesium aluminometasilicate, synthesized hydrotalcite, silicic anhydride synthesized aluminum silicate and combinations thereof.

In some embodiments the formulation excludes a UV-blocker.

In some embodiments the formulation excludes a thickener.

In some embodiments the formulation includes between about 1 weight % and about 20 weight % of a non-ionic surfactant. In some embodiments, the non-ionic surfactant is less than about 1 weight % of the formulation. In some embodiments, the non-ionic surfactant is less than about 0.5 weight % of the formulation. In some embodiments, the non-ionic surfactant is selected from the group consisting of alkylphenol ethoxylates, aliphatic alcohol ethoxylates, aliphatic alkylamine ethoxylates, sorbitan esters and their ethoxylates, castor oil ethoxylates, ethylene oxide/propylene oxide copolymers, polymeric surfactants and combinations thereof.

In some embodiments the formulation includes between about 0.1 weight % and about 90 weight % of a solvent. In some embodiments, the solvent is less than about 20 weight % of the formulation. In some embodiments, the solvent is less than about 10 weight % of the formulation. In some embodiments, the solvent is selected from the group consisting of alcohols, alkenes, alkanes, alkynes, phenols, hydrocarbons, chlorinated hydrocarbons, ketones, water, ethers and combinations thereof.

In some embodiments the formulation includes between about 0.05 weight % and about 5 weight % of an anti-foaming agent. In some embodiments, the anti-foaming agent is less than about 1 weight % of the formulation. In some embodiments, the anti-foaming agent is selected from the group consisting of sodium or ammonium phosphates, sodium carbonate or bicarbonate, sodium acetate, sodium metasilicate, magnesium or zinc sulfates, magnesium hydroxide hydrates of any of the forgoing, sodium alkylsulfosuccinates, silicious compounds, magnesium compounds, C10-C22 fatty acids, polyvalent metal salt compounds and combinations thereof.

In some embodiments the formulation includes between about 0.05 weight % and about 3 weight % of an anti-caking agent. In some embodiments, the anti-caking agent is less than about 1 weight % of the formulation. In some embodiments, the anti-caking agent is selected from the group consisting of attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids, refined kaolin clay, amorphous precipitated silica dioxide, refined clay, fumed silica and combinations thereof.

In some embodiments, the formulation is diluted so that the concentration of the polymer-associated pyrethroid compound is between about 0.1 to about 1000 ppm. In some embodiments, the formulation is diluted so that the concentration of the polymer-associated pyrethroid compound is between about 10 to about 1000 ppm. In some embodiments, the formulation is diluted so that the concentration of the polymer-associated pyrethroid compound is between about 10 to about 500 ppm. In some embodiments, the formulation is diluted so that the concentration of the polymer-associated pyrethroid compound is between about 10 to about 100 ppm.

In some embodiments, the formulation is in an aqueous dispersion. In some embodiments, the concentration of the pyrethroid in the dispersion is less than solubility limit of the pyrethroid in water. In some embodiments, the pyrethroid is associated with the polymer in the dispersion. In some embodiments, the water used to form the dispersion has an ionic strength of between about 0 to about 8000 ppm calcium +2 equivalent. In some embodiments, the water used to form the dispersion has an ionic strength of between about 100 to about 2000 ppm calcium +2 equivalent. In some embodiments, the water used to form the dispersion has an ionic strength of between about 100 to about 400 ppm calcium +2 equivalent. In some embodiments, the water used to form the dispersion has an ionic strength of between about 50 to about 400 ppm calcium +2 equivalent. In some embodiments, the water used to form the dispersion has an ionic strength of between about 1000 to about 4000 ppm calcium +2 equivalent.

In some embodiments, the aqueous dispersion further contains an herbicide. In some embodiments, the herbicide is glyphosate. In some embodiments, the formulation further includes a fertilizer. In some embodiments, the fertilizer is a liquid fertilizer. In some embodiments, the fertilizer comprises at least one of the elements selected from the group consisting of the following: boron, copper, manganese, iron, chorine, molybdenum, zinc sulfur, nitrogen, phosphorus and potassium.

In some embodiments the formulation includes between about 1 weight % and about 20 weight % of a non-ionic surfactant. In some embodiments, the non-ionic surfactant is less than about 1 weight % of the formulation. In some embodiments, the non-ionic surfactant is less than about 0.5 weight % of the formulation. In some embodiments, the non-ionic surfactant is selected from the group consisting of alkylphenol ethoxylates, aliphatic alcohol ethoxylates, aliphatic alkylamine ethoxylates, sorbitan esters and their ethoxylates, castor oil ethoxylates, ethylene oxide/propylene oxide copolymers, polymeric surfactants and combinations thereof.

In some embodiments, the formulation shows less than about a 10% drop in mortality rate seven days after application, as compared to the day of application. In some embodiments, the formulation shows less than about a 25% drop in mortality rate fourteen days after application, as compared to the day of application. In some embodiments, the mortality rate drops by less than 15% between seven days and fourteen days after application.

In various aspects the present disclosure provides a method of using the formulation described above by applying the formulation to the root zone of a plant.

In various aspects the present disclosure provides a method of using the formulation described above by applying the formulation to one part of a plant and the pyrethroid translocates to an unapplied part of the plant. In some embodiments, the unapplied part of the plant comprises new plant growth since the application.

In various aspects the present disclosure provides a method of inoculating a plant with a pyrethroid against pests by applying the any formulation described above to the plant's roots. In various aspects the present disclosure provides a method of increasing a plant's pest resistance by applying the any formulation described above to the plant's roots. In some embodiments, pest is a soil borne pest.

In some embodiments, the concentration of the polymer-encapsulated pyrethroid compound is between about 0.1 to about 1000 ppm. In some embodiments, the concentration of the polymer-encapsulated pyrethroid compound is between about 10 to about 1000 ppm. In some embodiments, the concentration of the polymer-encapsulated pyrethroid compound is between about 10 to about 500 ppm. In some embodiments, the concentration of the polymer-encapsulated pyrethroid compound is between about 10 to about 100 ppm.

In some embodiments, the plant is selected from the families fabaceaae, brassicaceae, rosaceae, solanaceae, convolvulaceae, poaceae, amaranthaceae, laminaceae and apiaceae. In some embodiments, the plant is selected from oil crops, cereals, pasture, turf, ornamentals, fruit, legume vegetables, bulb vegetables, cole crops, tobacco, soybeans, cotton, sweet corn, field corn, potatoes and greenhouse crops.

In some embodiments, the pest is selected from the classes lepidoptera, diptera, syphonaptera, ixodida, blattaria, isoptera, hymenoptera, hemiptera, coleoptera and combinations thereof.

In various aspects the present disclosure provides a method of using any formulation as described above by applying the formulation trees, bushes or shrubs.

In various aspects the present disclosure provides a method of using any formulation as described above to target a pest and the formulation is applied to a soybean plant at a concentration of between about 4 and about 37 grams of bifenthrin per hectare and the pest is selected from the group consisting of Alfalfa Caterpillar, Aphids, Aster Leafhopper, Bean Leaf Beetle, Beet Armyworm, Cloverworm, Corn Earworm, Corn Rootworm (adult), Cucumber Beetles, Cutworms, European Corn Borer, Fall Armyworm, Flea Beetle, Grasshoppers, Imported Cabbageworm, Japanese Beetle (Adult), Leafhoppers, Leafminer, Loopers, Mexican Bean Beetle (adult), Pea Leaf Weevil, Pea Weevil, Plant Bug, Saltmarsh Caterpillar, Sap Beetle, Southern Armyworm, Stink Bugs, Tarnished Plant Bug, *Thrips*, Tobacco budworm, Webworms, Western Bean Cutworm, Whitefly, and Yellowstriped armyworm.

In various aspects the present disclosure provides a method of using any formulation as described above to target a pest and the formulation is applied to a soybean plant at a concentration of between about 9 and about 90 grams of bifenthrin per hectare and the pest is selected from the group consisting of *Lygus* species, Whitefly, and Two Spotted Spider Mite.

In various aspects the present disclosure provides a method of using any formulation as described above to target a pest and the formulation is applied to a corn plant at a concentration of between about 4 and about 37 grams of bifenthrin per hectare and the pest is selected from the group consisting of Aphids, Army Cutworm, Beet Armyworm, Cereal Leaf Beetle, Chinch Bug, Common Stalk Borer, Corn Earworm, Corn Rootworm (Adults), Cucumber Beetle (Adults), Cutworm Species, European Corn Borer, Fall Armyworm, Flea Beetle, Grasshoppers, Greenbug, Japanese Beetle (Adult), Sap Beetle, Southern Armyworm, Southern Corn Leaf Beetle, Southwestern Corn Borer, Stinkbugs, Tarnished Plant Bug, True Armyworm or Armyworm Species, Webworms, Western Bean Cutworm, and Yellowstriped Armyworm.

In various aspects the present disclosure provides a method of using any formulation as described above to target a pest wherein the formulation is applied to a soybean plant at a concentration of between about 2 and about 17 grams of lambda-cyhalothrin per hectare and the pest is selected from the group consisting of Bean Leaf Beetle, Cabbage Looper Corn Earworm, Cutworm spp., Green Cloverworm, Mexican Bean Beetle, Mexican Corn Rootworm Beetle (Adult), Northern Corn Rootworm Beetle (Adult), Painted Lady (Thistle) Caterpillar, Potato Leafhopper, Saltmarsh Caterpillar, Southern Corn Rootworm Beetle (Adult), Soybean Aphids, Three-cornered Alfalfa Hopper, *Thrips*, Velvetbean Caterpillar, Western Corn Rootworm Beetle (Adult), and Woollybear Caterpillar.

In various aspects the present disclosure provides a method of using any formulation as described above to target a pest and the formulation is applied to a soybean plant at a concentration of between about 3 and about 29 grams of lambda-cyhalothrin per hectare and the pest is selected from the group consisting of Armyworm, Blister Beetle spp., European Corn Borer, Fall Armyworm, Grasshopper species, Japanese Beetle (Adult), Plant Bug species, Silverspotted Skipper, Stink Bug species, Tobacco Budworm, and Webworm species.

In various aspects the present disclosure provides a method of using any formulation as described above to target a pest and the formulation is applied to a corn plant at a concentration of between about 2 and about 17 grams of lambda-cyhalothrin per hectare and the pest is selected from the group consisting of Corn Earworm, Cutworm species, Green Cloverworm, Meadow Spittlebug, and Western Bean Cutworm.

In various aspects the present disclosure provides a method of using any formulation as described above to target a pest and the formulation is applied to a corn plant at a concentration of between about 2 and about 23 grams of lambda-cyhalothrin per hectare and the pest is selected from the group consisting of Armyworm, Bean Leaf Beetle, Bird Cherry-Oat Aphid, Cereal Leaf Beetle, Corn Leaf Aphid, English Grain Aphid, European Corn Borer, Flea Beetle species, and Grasshopper species.

In various aspects the present disclosure provides a method of using any formulation as described above to target a pest and the formulation is applied to a corn plant at a concentration of between about 1 and about 8 grams of cyfluthrin per hectare and the pest is selected from the group consisting of Cutworms, Black Cutworm, Granulate Cutworm, Sand Hill Cutworm; and Flea beetles.

In various aspects the present disclosure provides a method of using any formulation as described above to target a pest and the formulation is applied to a corn or cornplant at a concentration of between about 1 and about 15 grams of cyfluthrin per hectare and the pest is selected from the group consisting of Armyworm, Bean leaf beetle. Cereal leaf beetle, Chinch bug, Click beetle, Corn earworm, Corn rootworms, European corn borer, Grape colaspis, Japanese beetle, June beetle, Leafhoppers, Masked chafer, Southern armyworm, Southern corn leaf beetle, Southwestern corn borer, Stalk borer, Stink bugs, Webworm, Western bean cutworm, and Yellowstriped armyworm In various aspects the present disclosure provides a method of using any formulation as described above to target a pest and the formulation is applied to a soybean plant at a concentration of between about 1 and about 8 grams of cyfluthrin per hectare and the pest is selected from the group consisting of Bean leaf beetle, Cutworms, Potato leafhopper, *Thrips*, and Green cloverworm.

In various aspects the present disclosure provides a method of using any formulation as described above to target a pest and the formulation is applied to a soybean plant at a concentration of between about 1 and about 15 grams of cyfluthrin per hectare and the pest is selected from the group consisting of Armyworm, Bean leaf beetle, Bean leaf webber, Beet armyworm, Blister beetle, Cabbage looper, Click beetle, Corn earworm, Corn rootworms, Cucumber beetle, European corn borer, Fall armyworm, Grape colaspis, Japanese beetle, June beetle, *Lygus* bug, Masked chafer, Mexican bean beetle, Saltmarsh caterpillar, Silverspotted skipper, Southern armyworm, Stink bugs, Tarnished plant bug, Threecornered alfalfa hopper, Tobacco budworm, Velvetbean caterpillar, Webworm, Woolybear caterpillar, and Yellowstriped armyworm.

In various aspects the present disclosure provides a method of making a high solids liquid suspension formulation including the steps of milling nanoparticles of a polymer-associated pyrethroid compound with, a dispersant and/or wetting agent; and water.

In various aspects the present disclosure provides a method of making a high solids liquid suspension formulation including the steps of milling polyelectrolyte nanoparticles with, a pyrethroid compound, a dispersant and/or wetting agent; and water.

In various aspects the present disclosure provides a method of making a wettable granule formulation including the steps of mixing dried nanoparticles of a polymer-associated pyrethroid compound with water, extruding the mixture through an orifice; and dividing the extruded material into granules.

In some embodiments, the pyrethroid compound used in the method of making described above has a melting point below 100° C. In some embodiments, the pyrethroid compound used in the method of making described above has a melting point below 80° C.

In some embodiments, the pyrethroid compound used in the method of making described above is selected from the group consisting of the following bifenthrin, gamma-cyhalothrin, lambda-cyhalothrin, cypermethrin, zeta-cypermethrin, beta-cypermethrin, esfenvalerate, fenvalerate, permethrin, resmethrin, acrinathrin and combination thereof.

In some embodiments, the pyrethroid compound used in the method of making described above is between about 5 weight % and about 25 weight % of the formulation. In some embodiments, the pyrethroid compound used in the method of making described above is between about 10 weight % and about 25 weight % of the formulation. In some embodiments, the pyrethroid compound used in the method of making described above is between about 15 weight % and about 25 weight % of the formulation.

In some embodiments, the polymer nanoparticles and the pyrethroid compound used in the method of making described above the are together between about 20 weight % and about 80 weight % of the formulation. In some embodiments, the polymer nanoparticles and the pyrethroid compound used in the method of making described above the are together between about 20 weight % and about 60 weight % of the formulation. In some embodiments, the polymer nanoparticles and the pyrethroid compound used in the method of making described above the are together between about 20 weight % and about 50 weight % of the formulation. In some embodiments, the polymer nanoparticles and the pyrethroid compound used in the method of making described above the are together between about 30 weight % and about 50 weight % of the formulation.

In some embodiments the ratio of pyrethroid compound to polymer within the nanoparticles used in the methods of making described above is between about 5:1 and about 1:5.

In some embodiments, the methods of making described above further include one or more of the following formulating agents: an anti-freeze, an anti-foaming agent, a thickener, a preservative.

DEFINITIONS

Figure 1:
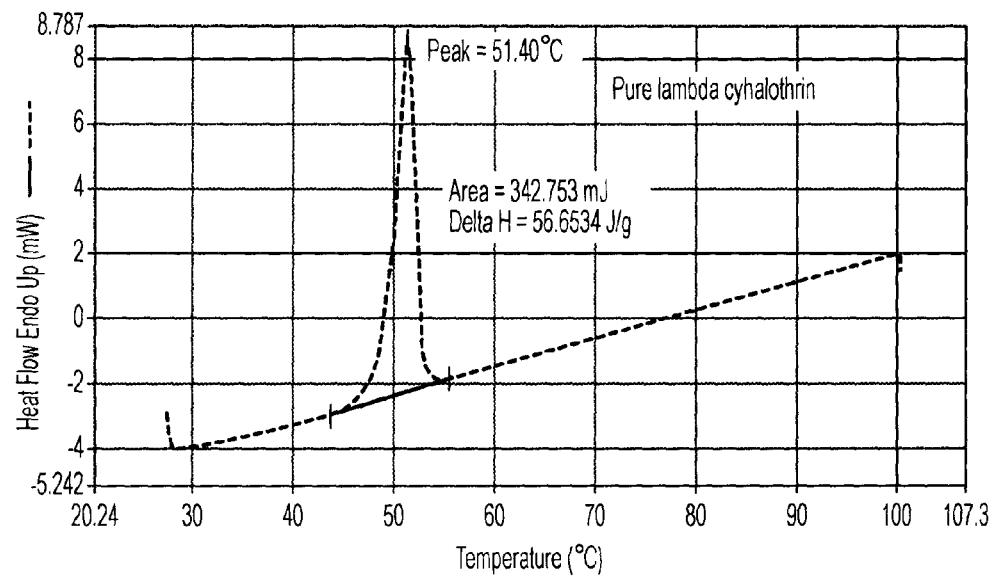
FIG. 1 shows the results of Differential Scanning calorimetry (DSC) analysis of pure lambda cyhalothrin and FIG. 2 shows a solid formulation of lambda cyhalothrin prepared according to Example 7.

As used herein, the term "inoculation" refers to a method used to administer or apply a formulation of the present disclosure to a target area of a plant or pest. The inoculation method can be, but is not limited to, aerosol spray, pressure spray, direct watering, and dipping. Target areas of a plant could include, but are not limited to, the leaves, roots, stems, buds, flowers, fruit, and seed. Target areas of a pest (e.g., insect) could include, but are not limited to, the head, eyes, maxilla, mandible, antennae, thorax, leg, wings, and abdomen. Inoculation can include a method wherein a plant is treated in one area (e.g., the root zone or foliage) and another area of the plant becomes protected (e.g., foliage when applied in the root zone or new growth when applied to foliage).

As used herein, the term "wettable granule" also referred to herein as "WG", "water dispersible granule", and "dispersible granule" refers to a solid granular formulation that is prepared by a granulation process and that contains nanoparticles of polymer-associated active ingredient, or aggregates of the same, a wetting agent and/or a dispersant, and optionally an inert filler. Wettable granules can be stored as a formulation, and can be provided to the market and/or end user without further processing. In some embodiments, they can be placed in a water-soluble bag for ease of use by the end user. In practical application, wettable granules are prepared for application by the end user. The wettable granules are mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "wettable powder" also referred to herein as "WP", "water dispersible powder" and "dispersible powder", refers to a solid powdered formulation that contains nanoparticles of polymer-associated active ingredient, or aggregates of the same, and optionally one or more of a dispersant, a wetting agent, and an inert filler. Wettable powders can be stored as a formulation, and can be provided to the market and/or end user without further processing. In some embodiments, they can be placed in a water-soluble bag for ease of use by the end user. In practical application, a wettable powder is prepared for application by the end user. The wettable powder is mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "high solids liquid suspension" also referred to herein as "HSLS" refers to a liquid formulation that contains nanoparticles of polymer nanoparticles associated with active ingredient, or aggregates of the same, a wetting agent and/or a dispersant, an anti-freezing agent, optionally an anti-settling agent or thickener, optionally a preservative, and water. High solids liquid suspensions can be stored as a formulation, and can be provided to the market and/or end user without further processing. In practical application, high solids liquid suspensions are prepared for application by the end user. The high solids liquid suspensions are mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, "control of pests" and the like refer to the reduction of pests to undetectable levels, or to the reduction or suppression of pests to acceptable levels as determined by one of ordinary skill in the art (e.g. a crop grower). Determinations of acceptable levels of pest reduction are based on a number of factors, including to the crop, pest, severity of the pest, use restrictions, economic thresholds and others know to those of ordinary skill in the art.

DESCRIPTION OF VARIOUS EMBODIMENTS
OF THE INVENTION

Pyrethroids are a very important class of pesticide globally. They are used in crop and non-crop plant protection applications, as well as human health and animal health applications. Pyrethroids as a class are derived from pyrethrum, which is a substance of plant origin from chrysanthemum flowers. Pyrethrum has been used since antiquity but is deactivated in sunlight extremely rapidly. Synthetic pyrethroids have therefore been developed. However, pyrethroids, whether naturally occurring or synthesized suffer from several major problems that make them challenging to use as pesticides. In particular, in addition to being UV sensitive, pyrethroids are very poorly soluble in water, hydrolyze under alkaline conditions, exhibit low soil mobility and do not work systemically in plants. Different formulation techniques have therefore been developed in an attempt to address these deficiencies. An ideal formulation would have adequate loading of the active ingredient, be non-odorous, non-caking, non-foaming, stable under extreme conditions for extended periods of time, disperse rapidly upon addition to a spray tank, be compatible with a range of secondary additives and other agricultural products (fertilizer, fungicide, herbicide and other formulations) added to a spray tank, pourable or flowable, and non-dusty (for solid formulations), and have sufficient/superior rainfast properties after application.

UV Stability

Current pyrethroids vary in their susceptibility to sunlight and exhibit a wide range of half lives as shown in Table 1.

TABLE 1

Photolytic stability of some pyrethroids

| Pyrethroid | Photolytic stability |
| --- | --- |
| Bifenthrin | $DT_{50}$ 255 days in natural daylight[+] |
| Cyhalothrin | Stable to light; slow hydrolysis by water in sunlight at pH 7-9[+] |
| Gamma-cyhalothrin | Photolysis $DT_{50}$ (aqueous solution) 10.6 days[+] |
| Lambda-cyhalothrin | Photodegraded in water and soil; half-life of 5 days on plant surface[++] |
| Cypermethrin | Relatively stable to light in field conditions; half-life of 5 days on foliage[+, ++] |
| Zeta-cypermethrin | Photolysis $DT_{50}$ (aqueous solution) 20-26 days[+] |
| Deltamethrin | Ester bond splitting and bromine loss under sunlight[+] |
| Esfenvalerate | Stable[+] |
| Fenvalerate | Decarboxylation occurs in light[+] |
| Permethrin | Photolysis in water[++] |
| Resmethrin | Decomposes rapidly on exposure to air and light[+] |

[+]The e-pesticide manual, Ver. 5. British Crop Protection Council
[++]National Pesticide Telecommunications Network General and Technical Fact Sheets)

Due to the tendency of pyrethroids to degrade in sunlight, most pyrethroid formulations include a UV-blocker such as titanium dioxide or 1,2-dihydroxybenzophenone. The addition of UV-blockers into a formulation can complicate formulations, as UV-blockers need to be soluble or dispersible in the matrix in which the product is formulated. It would therefore be desirable to provide formulations that do not require UV-blockers.

Solubility

Pyrethroids are typically very poorly soluble in water, usually with parts per billion (ppb) or lower level solubility. They have higher solubility in polar organic solvents such as acetone, methanol, or acetonitrile. See Table 2 for a list of typical pyrethroids and their solubility in different common solvents (taken from the e-pesticide manual, Ver. 5. British Crop Protection Council; National Pesticide Telecommunications Network General and Technical Fact Sheets).

TABLE 2

Solubility of some pyrethroids in common solvents and octanol-water partition coefficients and melting temperatures

| Pyrethroid | Solubility (μg/L or ppb) | $K_{OW}$ | $T_{melting}$ (° C.) |
| --- | --- | --- | --- |
| Bifenthrin | water: <1 ug/L<br>acetone, chloroform, dichloromethane, diethyl ether, toluene: soluble | logP > 6 | 68-70 |
| Cyhalothrin | water: 4.2 ug/L (pH5, 20° C.)<br>acetone, dichloromethane, methanol, diethyl ether, ethyl acetate, hexane, toluene: >500 g/L | logP = 6.9 (20° C.) | — |
| Gamma-cyhalothrin | water 2.1 × 10$^{-3}$ mg/l (20° C.) | logP = 4.96 (19° C.) | 55.6 |
| Lambda-cyhalothrin | water 0.005 mg/l (pH 6.5, 20° C.)<br>acetone, methanol, toluene, hexane, ethyl acetate > 500 g/l | logP = 7 (20° C.) | 47-49 |
| Cypermethrin | water: 4 ug/L (pH7)<br>acetone, chloroform, cyclohexanone, xylene > 450, ethanol 337, hexane 103 (all in g/l, 20° C.) | logP = 6.6 | 61-83 * |
| Alpha-cypermethrin | water: 0.67 ug/L (pH 4); 3.97 ug/L (pH 7); 4.54 ug/L (pH 9).<br>n-hexane: 6.5 g/L<br>toluene: 596 g/L<br>methanol: 21.3 g/L<br>isopropanol 9.6 g/L | logP = 6.954 (pH7) | 81.5 |
| Beta-cypermethrin | water: 51.5 ug/L (5° C., pH7); 93.4 ug/L (25° C., pH7); 276 ug/L (35° C., pH7)<br>Isopropanol: 11 mg/mL<br>xylene: 349 mg/mL<br>acetone: 2102 mg/mL<br>ethyl acetate: 1427 mg/mL | logP = 4.7 | 63-69 |
| Theta-cypermethrin | water 114.6 μg/l (pH 7, 25° C.)<br>isopropyl alcohol 18.0, diisopropyl ether 55.0, hexane 8.5 (all in mg/ml, 20° C.) | | 81-87 |
| Zeta-cypermethrin | water 0.045 mg/l (25° C.)<br>miscible in most organic solvents | logP = 5-6 | — |
| Deltamethrin | water < 0.2 μg/l (25° C.)<br>dioxane 900, cyclohexanone 750, dichloromethane 700, acetone 500, benzene 450, DMSO 450, xylene 250, ethanol 15, isopropanol 6 (all in g/l, 20° C.) | logP = 4.6 (25° C.) | 100-102 |

TABLE 2-continued

Solubility of some pyrethroids in common solvents and octanol-water partition coefficients and melting temperatures

| Pyrethroid | Solubility (µg/L or ppb) | $K_{OW}$ | $T_{melting}$ (° C.) |
|---|---|---|---|
| Esfenvalerate | water 0.002 mg/l (20° C.) xylene, acetone, chloroform, ethanol, methanol, DMF, hexylene glycol > 450, hexane 77 (all in g/l, 20° C.) | logP = 6.5 (pH 7, 25° C.) | 38-54 |
| Fenvalerate | water < 10 µg/l (25° C.) n-hexane 53, xylene ≥ 200, methanol 84 (all in g/l, 20° C.) | logP = 5.01 (23° C.) | 39-53 |
| Permethrin | water $6 \times 10^{-3}$ mg/l (pH 7, 20° C.); cis-isomers 0.20 mg/l (pH not stated, 25° C.); trans-isomers 0.13 mg/l (pH not stated, 25° C.) xylene, hexane > 1000, methanol 258 (all in g/kg, 25° C.) | logP = 6.1 (20° C.) | 34-35 |
| Resmethrin | water 37.9 µg/l (25° C.) acetone c. 30%, chloroform, dichloromethane, ethyl acetate, toluene > 50%, xylene > 40%, ethanol, n-octanol c. 6%, n-hexane c. 10%, isopropyl ether c. 25%, methanol c. 3% (all m/v, 20 ° C.) | logP = 5.43 (25° C.) | 56.5 |

* Depends on isomer ratio

Because pyrethroids have such low water solubility they need to be formulated to disperse in water before they can be applied to a plant or pest. The two most common liquid formulation techniques that are currently used to achieve this involve preparing an emulsifiable concentrate or a suspension concentrate of the pyrethroid in question.

An emulsifiable concentrate (EC) is a formulation where the active ingredient is dissolved in a suitable organic solvent in the presence of surfactants. When the EC is dispersed into the spray tank and agitated, the surfactants emulsify the organic solvent into water, and the active ingredient is delivered in the organic solvent phase to the plant or pest.

A suspension concentrate (SC) is a high solids concentrate in water. The active ingredient is milled into particles that are 1-10 microns (Alan Knowles, *Agrow Reports: New Developments in Crop Protection Product Formulation*. London: Agrow Reports May 2005). These solid particles are then dispersed into water at high concentration using surfactants. After adding the SC into the spray tank, the surfactant-stabilized particles disperse into water and are applied (still as solid particles) to the plant or pest.

Solid formulation techniques that are currently used include wettable granules or powders, where the active ingredient is absorbed to a dispersible carrier that is provided dry to the end user. When mixed into the spray tank, the carrier disperses into the water, carrying the active ingredient with it. Particle sizes for these carriers can be anywhere in the range of 1-10 microns (Alan Knowles, *Agrow Reports: New Developments in Crop Protection Product Formulation*. London: Agrow Reports May 2005). As discussed in more detail below there remains a need for alternative formulations that can be used to disperse pyrethroids in water.

Hydrolysis

Pyrethroids are typically quite stable when dispersed in water at acidic and neutral pH but become increasingly susceptible to hydrolysis under alkaline conditions. Stability data for some pyrethroids is provided in Table 3 (taken from the e-pesticide manual, Ver. 5. British Crop Protection Council).

TABLE 3

Stability data of some pyrethroids in different media

| Pyrethroid | Stability data |
|---|---|
| Bifenthrin | Soil $DT_{50}$ (lab.) 53-192 d (mean 106 d) |
| Cyhalothrin | Slowly hydrolyzed by water in sunlight at pH 7-9, more rapidly at pH > 9; pKa > 9 (hydrolysis prevents measurement) |
| Gamma-cyhalothrin | — |
| Lambda-cyhalothrin | Rapid and extensive degradation of parent compound in aquatic systems; $DT_{50}$ for degradation in lab. water-sediment systems 7-15 d; in a microcosm, $DT_{50}$ < 3 h, $DT_{90}$ < 3 d |
| Cypermethrin | Hydrolyzed in alkaline media; $DT_{50}$ 1.8 d (pH 9, 25° C.); stable at pH 5 and 7 (20° C.) |
| Alpha-cypermethrin | Hydrolyzed in strongly alkaline media; $DT_{50}$ (pH 4, 50° C.) stable over 10 d, (pH 7, 20° C.) 101 d, (pH 9, 20° C.) 7.3 d. Thermally stable up to 220° C. |
| Beta-cypermethrin | Hydrolyzed in strongly alkaline media. $DT_{50}$ (extrapolated) 50 d (pH 3, 5, 6), 40 d (pH 7), 20 d (pH 8), 15 d (pH 9) (all at 25° C.) |
| Theta-cypermethrin | In water, $DT_{50}$ (extrapolated) 50 d (pH 3, 5, 6), 20 d (pH 7), 18 d (pH 8), 10 d (pH 9) (all at 25° C.) |
| Zeta-cypermethrin | Hydrolysis $DT_{50}$ stable (pH 5), 25 d (pH 7, 25° C.), 1.5 h (pH 9, 50° C.) |
| Deltamethrin | $DT_{50}$ 31 d (pH 8), 2.5 d (pH 9), stable at pH 5 and 7 |
| Esfenvalerate | Stable to hydrolysis at pH 5, 7 and 9 (25° C.). |
| Fenvalerate | rapidly hydrolyzed in alkaline media |
| Permethrin | More stable in acidic than alkaline media, with optimum stability c. pH 4; $DT_{50}$ 50 d (pH 9), stable (pH 5, 7) (all 25° C.) |
| Resmethrin | Unstable in alkaline media |

Soil Mobility

Pyrethroids have high affinity for soil and sediment particulate matter. Without wishing to be bound by any theory, this is thought to be primarily due to their very non-polar nature and lack of water solubility. When pyrethroids are dispersed in water they therefore have a tendency to associate with natural organic matter found in soils and have low mobility within the soil. General information about specific pyrethroid solid persistence and mobility can be found in the General and Technical Fact Sheets from the National Pesticide Telecommunications Network; the e-pesticide manual, Ver. 5. British Crop Protection Council; and Laskowski D A, "Physical and Chemical Properties of Pyrethroids," *Rev. Environ. Contam. Toxicol.* 2002; 174:49-170. This lack of soil mobility limits the pests that can be targeted with pyrethroids. In particular, soil-borne pests such as grubs are not usually targets for pyrethroids. Similar issues arise when pyrethroids need to penetrate a biological barrier above the soil surface, such as thatch or crop waste left on the field. It would therefore be desirable to provide pyrethroid formulations that have increased soil mobility.

Lack of Systemic Effect

Pyrethroids are non-systemic. This means that they do not penetrate the leaf cuticle and are not taken up into plant tissue after application. They are also non-systemic from root uptake; that is, they do not get taken up from the root and distributed throughout the plant tissue. This can be problematic, as it means that any plant tissue that needs to be protected needs to be efficiently covered by the application process. Aerial spray or foliar spray is often non-uniform and does not lead to complete coverage of the exterior of the plant (e.g., see Henriet and Baur, *Bayer CropScience Journal* 62(2):243, 2009). In addition, as plants grow they develop new foliar tissue that was not treated with pyrethroid and hence will not be protected from insect pressure until the next application. Thus, in a recent summary of pyrethroid formulations Housset and Dickmann stated that "the non-systemic nature of pyrethroids presents a challenge for use as the active ingredient must be efficiently delivered directly to the target insect" (see *Bayer CropScience Journal* 62(2):138, 2009). In other words, in order to be effective, the insecticide has to be on the exterior surface of the plant where it will be in direct contact with the insect. No current formulations of pyrethroids are marketed as having systemic activity. If a pyrethroid insecticide could be made systemic through improvements in formulation, it would dramatically improve its ability to be used on crops due to improved coverage over and throughout the individual plants as well as protection of new growth.

Efficacy Against "Sap-Sucking Insects"

Pyrethroid compounds have been widely used as broad spectrum insecticides and miticides in agricultural and structural pest control applications. However, formulations of pyrethroid compounds, such as bifenthrin, suffer from the limitation of not being effective against some types of important sap-sucking pests. Many pyrethroids are not recommended for use to control sap-sucking pests, or if they are recommended, the doses used are generally higher, as compared to the doses used to control other pests (e.g., lepidopterans). As used herein, "sap-sucking pests" or "sucking pests" refers to insects that puncture plants using piercing or rasping mouthparts to gain access to and feed on plant fluids such as phloem sap, xylem sap and cellular fluids. Exemplary sap-sucking pests include, but are not limited to, members of the hemiptera order, (e.g., aphids, leafhoppers, stink bugs, whiteflies, scale insects, mealybugs, members of the Miridae family), members of the thysanoptera order (e.g., *thrips*).

Many sap-sucking insects and mites cause crop damage in a number of ways. As from the mechanical damage of plant tissues and depletion of sap fluids which negatively affects crop vitality and yield, disease-causing viruses, bacteria and fungi can be transmitted or introduced to the crop during feeding by these pests. Toxins, which can cause a variety of harmful effects including stunting of plant growth and even plant death, are injected into crops by various kinds of these insects. In addition, some sap-sucking insects secrete honeydew, a sticky, high-sugar content liquid onto the plants on which they feed. Honeydew, in turn, attracts and allows fungi to grow on the crop, imparting a sooty appearance to the affected crop and fruit. Such contamination can lead to a reduction of palatability of the crop to livestock, a reduction of the value of the crop, culling of affected crop, and other undesirable outcomes.

Efficacy against Mites

Various species of mites are pests of plants, including many important agricultural crops. Mites are arachnids that are members of the Acari subclass. Pyrethroids are not generally recommended to controls mites, acaricides such as avermectins and carbamate, among others being favored. If pyrethroids are to be used to control mites, the recommended doses are generally higher than the recommended doses for other pests (e.g. lepidopterans). Table 4 provides representatives example of application rates for the control of various pests on Head Lettuce with Brigade® 2EC, a typical commercially available bifenthrin emulsion concentrate (25.1% bifenthrin). It is notable that the minimum doses listed for the control of the labeled mite pests are higher than the minimum doses for the majority of labelled insect pests. Exemplary mite pests include, but are not limited to, members of the prostigmata family and members of the *Rhizoglyphus* genus.

TABLE 4

Application doses for control of various insect pests on Head Lettuce by Brigade® 2EC

| Dosage | Pest Type |
|---|---|
| 37-112 g of bifenthrin/ha | Aphids |
| | Armyworms |
| | Corn earworm |
| | Cucumber Beetles |
| | Cutworms |
| | Diamondback moth |
| | Flea beetles |
| | Imported Cabbageworm |
| | Leafhoppers |
| | Salt Marsh Caterpillar |
| | Stink bug spp. |
| | Tobacco Budworm |
| | Whitefly |
| 90-112 g of bifenthrin/ha | *Lygus* spp. |
| | Carmine Mite |
| | Two Spotted Spider Mite |

Skin Irritation

Some pyrethroids cause skin irritation (e.g., itching or sensitization) when contacted with the skin of end users. In order to protect the end user from this effect, formulations have been developed that minimize the interaction between the end user and the formulation, e.g., microencapsulation.

Formulations—Generally

The aforementioned limitations of pyrethroids as a class manifest themselves in (a) how they are currently applied to plants and (b) how they are formulated by manufacturers. As an example, because pyrethroids are susceptible to UV degradation, end users (e.g., farmers or golf course maintenance managers) need to apply pyrethroids more often than if they were longer lasting. As another example, because pyrethroids lack systemic activity (which would protect new growth of crops), end users need to continually re-apply pyrethroids in order to protect fast growing crops or fruit bearing crops. Similarly, pyrethroids will also need to be re-applied in certain cases because some pyrethroid formulations are not rainfast and may easily get washed off the foliage if heavy rainfall occurs soon after application. These limitations present real issues to end users who are faced with increasing regulatory and consumer pressure to use fewer pesticides. With respect to manufacturing, pyrethroid formulations require a variety of complicated formulation techniques and/or the use of formulation agents to counter to the UV instability, water insolubility, non-systemic nature, and low soil mobility of pyrethroids. For example, as discussed above UV-blockers are used in many formulations to preserve the pyrethroids, and a variety of synthetic variations of common pyrethroids have been developed in an attempt to provide UV stable pyrethroids.

In order to address these challenges we have developed new pyrethroid formulations. As demonstrated in the Examples and discussed below, in some embodiments these new pyrethroid formulations are soluble in water, UV stable (i.e., longer lasting), rainfast, mobile in soil and/or systemic. In some embodiments, these new pyrethroid formulations are compatible with other agricultural products (surfactants, leaf wetters, fertilizers, etc.) and stable in non-ideal solution conditions such as high salt, extreme pH, hard water, elevated temperatures, etc. In general, these new pyrethroid formulations comprise nanoparticles (optionally in aggregate form) of polymer-associated pyrethroids along with various formulating agents. Before discussing in detail various embodiments of the chemical and physical characteristics of these nanoparticles and formulating agents we turn to some general considerations of our pyrethroid formulations.

First, we note that for many of the aforementioned applications of pyrethroids the end user would like to receive a dry powder or granulated product containing the pyrethroid. Solid products are not only less expensive and easier to store and ship, but, generally, handling and environment risks (e.g., spills) are reduced as compared to liquid formulations. The dry product is added to water in the spray tank, agitated, and applied to the plant or pest. It is useful that the dry product disperse quickly in the spray tank and that there be as little as possible or no non-dispersible fraction (which can sediment or cake and can cause problems with spray equipment). Although granulation formulations are common in the art, it is important to note that individual formulations are not necessarily transferable from one active to another. Each active and application may need a different formulation, which can vary according to the target pest, the crop to which it is applied, the geography of its application, applicable regulatory structure, among other factors. Formulation development, even with well-known actives, is a complex and empirical process.

Second, formulation development (e.g., of granulation formulations) using pyrethroids and nanoparticles of polymer-associated active ingredient is non-trivial. In particular, traditional granulation processes are not particularly suitable to pyrethroids and nanoparticles of polymer-associated active ingredient. For example, traditional granulation of water-insoluble active ingredients normally involves first absorbing the active ingredient to a water-dispersible or water-soluble carrier, followed by addition of the other granulation ingredients and granulating. With our formulations, we do not use a traditional carrier. In addition, active ingredients with low melting points are difficult to granulate because the heat applied or generated during extrusion tends to melt the active ingredient and cause separation during granulation. As shown in Table 2, many pyrethroids have low melting points and would therefore suffer from this problem. Using nanoparticles of polymer-associated pyrethroid compounds was found to facilitate the granulation of these otherwise difficult to granulate actives ingredients by eliminating the need for low temperature granulation equipment (to prevent melting of the active). It was also found to facilitate the granulation of semi-solid or even liquid active ingredients. Thus, as described in the Examples, we have successfully prepared granules of cypermethrin (a syrupy liquid as received) and lambda cyhalothrin (a low-melting solid). Surprisingly, during granulation no phase separation or apparent melting of these active ingredients occurred. In fact, even if the granules were heated to above the melting point of the active ingredient no phase separation or apparent melting of the active ingredient occurred. Without wishing to be bound by theory, it is thought that the presence of the polymer nanoparticles provides a stable environment for the liquid active ingredients, preventing phase separation.

Third, in some embodiments, in order to make a water-dispersible granulated formulation with nanoparticles of polymer-associated active ingredient it was necessary to add a dispersant and a wetting agent. Although formulation agents, such as dispersants and wetting agents are known in the art, the selection of particular compounds and amounts for nanoparticles of polymer-associated active ingredient is non-trivial. Some dispersants, for example, were found to give rise to a negative effect in our formulations, e.g., dispersants like Soprophor BSU which are known to help decrease the particle size in standard granulated formulations unexpectedly gave rise to larger aggregates in our formulations.

Fourth, we have managed to produce high active ingredient (e.g., 30-80 weight %) content solid formulations using the nanoparticles of polymer-associated active ingredient. This is, in general, quite difficult to achieve using traditional solid formulating techniques, particularly if the active ingredient has a low melting point or is not solid at room temperature. Traditionally, in order to have such high active content formulations that have acceptable qualities such as rapid dispersion in water, adequate stability when dispersed, long-term storage stability, etc., a suspension concentrate is needed. Suspension concentrate formulations, though, have several problems ranging from the hydrolysis of the active ingredient, lower shelf life, and temperature sensitivity. Some active ingredients cannot be produced as suspension concentrates, because of the low melting point of the active ingredient. Low-melting active ingredients tend to suffer from long-term stability issues when stored. Additionally, active ingredients with moderate or high water solubility are difficult to formulate as suspension concentrates because they have a tendency to recrystallize and ripen over time, causing stability problems. Solid formulations do not suffer from hydrolysis issues because the formulation is nearly devoid of water. As shown in the Examples, our solid formulations are stable to temperature cycling and do not show any recrystallization or phase separation of the active ingredient even after repeated temperature cycling. In light of these results our solid formulations are expected to have a long shelf life.

Fifth, as an alternative to the aforementioned solid formulations we have also prepared high-concentration liquid suspensions (HCLS). These high-concentration liquid suspensions contain a significant amount of active ingredient associated with polymer nanoparticles and are added to water in a spray tank, agitated, and applied to the plant or pest. These formulations look like the traditional suspension concentrates that are discussed above and available from many manufacturers. However, because the nanoparticles of polymer-associated active ingredient, the formulations are prepared in different ways, described below, as compared to the traditional methods. Traditional suspension concentrates are milled surfactant-stabilized formulations of hard solid crystalline particles. In our case, because the polymer is a compressible, solvent-swellable solid, traditional methods would not work. Instead, we typically first manufacture the polymer nanoparticles, load them with active ingredient, and form the high-concentration liquid suspension either by drying the loaded polymer nanoparticles (with formulation agents if necessary) and re-suspending at the desired concentration. Alternatively, high concentration liquid suspensions with our polymer nanoparticles can be made by using water as the solvent during the loading process and removing water until the loaded polymer nanoparticles are at the desired concentration. Traditional suspension concentrates also require an anti-settling agent or thickener such as xanthan gum. The gum provides a polymer network that helps stabilize the micron-sized particles of active ingredient and prevent settling and coalescence. In our formulations, this is not required, because our particle size is smaller (nano vs. micro size) and hence settling and coalescence is less of a problem. In addition, without wishing to be limited by any theory, it is thought that the polymer nanoparticles themselves can help stabilize the formulation when dispersed at high concentration in water.

Sixth, because our formulations are based around nanoparticles of polymer-associated active ingredients, we can help improve the skin sensitization or irritation issue for some pyrethroids as mentioned above. Indeed, we have found that if skin exposure occurs they can be rinsed off more effectively than with traditional formulations such as EC formulations.

Seventh, because our formulations are based around nanoparticles of polymer-associated active ingredients, they are stable to relatively high salt conditions. Stability in high salt conditions is required especially when the formulation is to be mixed with other secondary agricultural products such as a concentrated fertilizer mix, exposed to high salt conditions (e.g. used in or with hard waters) mixed with other formulations (other pesticides, fungicides, and herbicides) or mixed with other tank-mix adjuvants. The ability to mix our formulations with other products can be beneficial to the end user because simultaneous agricultural products can be applied in a single application.

Eighth, our formulations are particularly rainfast. Without wishing to be bound by theory, polymer-associated active ingredients have an enhanced affinity to the target areas of the plant (and pest). When the formulation is applied to a plant/pest and then exposed to rain, the enhanced affinity can prevent washing off due to rain.

Formulations—Testing and Properties

After producing granulated, powdered, and high-concentration liquid suspension formulations, we decided to evaluate a range of biological activities. The Examples provided a detailed description of the experiments that were performed. Here we provide a summary.

In one example, we tested a granulated formulation of nanoparticles of polymer-associated lambda cyhalothrin for root uptake. In this experiment, the formulation was first dispersed in water and then applied by spray or irrigation to the root zone of the plant. After inoculating the plant in this way, the untreated foliage was harvested and evaluated for insecticidal activity. In general, pyrethroid insecticides that are in their soluble or molecular form (as would be the case in an EC formulation) would not show significant insecticidal activity when evaluated in this way, for the reasons described above (i.e., low soil mobility, water-insolubility and non-systemic nature of pyrethroids). We tested our formulation against a commercial microencapsulated formulation. We saw foliar activity for both our formulation and a commercial microencapsulated formulation, but significantly higher foliar activity for our formulation. It was surprising that either formulation would get taken up into the plant, but more so given the level of uptake for our formulations.

In another example, we tested a granulated formulation of polymer nanoparticle-associated lambda cyhalothrin for foliar uptake and translocation to growing tissue. In this experiment, the formulation was first dispersed in water and applied by spray to the foliar surface, with newly growing leaves covered from the spray. The covering was then removed and the new leaves were allowed to grow. After a certain interval, the leaves were harvested and assayed for insecticidal activity. In general, pyrethroid insecticides that are in their soluble or molecular form (as would be the case for, e.g., an EC formulation) would not show significant insecticidal activity when evaluated in this way. Again we tested our formulation against a commercial microencapsulated formulation. We saw insecticidal activity in the newly growing leaves for both formulations, but significantly improved activity for our formulation of polymer nanoparticle-associated lambda cyhalothrin. It was surprising that either formulation would get taken up into the plant in this way. In order for this to happen, the active ingredient would need to penetrate the waxy cuticle that prevents this type of transport.

In another experiment we tested granular and powdered formulations of polymer-associated cypermethrin for efficacy. In this experiment, the formulation was first dispersed in water and then leaf disks from cabbage or collard were dipped into the formulation. They were then dried and lepidoptera insects were exposed to the disks and mortality was measured as a function of time. We compared our formulations to a commercial formulation of cypermethrin that was an EC formulation. For some of our formulations, we saw dramatically improved mortality caused by the formulation, particularly at lower use rates.

In yet another experiment we tested granular formulations of polymer-associated lambda cyhalothrin for improvements in stability when exposed to UV irradiation. In this experiment, the formulation was first dispersed in water and then coated onto a glass substrate. The substrates were exposed to a solar light simulator and breakdown of the active ingredient was measured by thin layer chromatography ("TLC"). Our formulations, which did not contain a UV-blocker, took even longer to degrade than commercial formulations containing a UV-blocker. This was surprising, because our polymer nanoparticles only absorb 15% of the total UV radiation absorbed by a commercial UV-blocker. In order to check whether the improvements in UV stability impacted biological activity in the field, we tested the same formulations for improvements in residual activity. This experiment involved dispersing the formulation in water and then applying the formulation to a crop in the field. After a certain period of time, leaves were harvested and assayed for insecticidal activity. Our formulation had even longer-lasting activity as compared to a commercial microencapsulated product that is marketed as having superior residual activity.

Formulations—Components

In various aspects, the present disclosure provides formulations that comprise nanoparticles (optionally in aggregate form) of polymer-associated active ingredient along with various formulating agents.

Active Ingredient

As used herein, the term "active ingredient" ("AI", "ai") refers to pyrethroid compounds (i.e., pyrethroids). Pyrethroids are natural or synthetic chemical compounds that have similar pesticidal properties as the natural pyrethrins that are produced by the flowers of pyrethrums. In some embodiments, pyrethroids are synthetic esters derived from pyrethrins and have more stable pesticidal properties. The general pyrethrin structure is as follows:

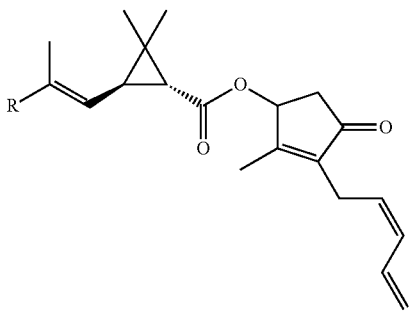

In some embodiments pyrethroids share a common chemical structure consisting of cyclopropane carboxylic acids, with variations in the alcohol portion of the compounds. Non-limiting examples of pyrethroid compounds are: acrinathrin, (S)-α-cyano-3-phenoxybenzyl (Z)-(1R,3S)-2,2-dimethyl-3-[2-(2,2,2-trifluoro-1-trifluoromethylethoxycarbonyl)vinyl]cyclopropane carboxylate; allethrin, RS)-3-allyl-2-methyl-4-oxocyclopent-2-enyl (+)-cis-trans-chrysanthemate; alpha-cypermethrin, A racemate comprising (S)-α-cyano-3-phenoxybenzyl (1R,3R)-3-(2,2-dichlorovinyl)-2,2-dimethylcyclopropanecarboxylate and (R)-α-cyano-3-phenoxybenzyl (1S,3S)-3-(2,2-dichlorovinyl)-2,2-dimethylcyclopropanecarboxylate; beta-cyfluthrin, a reaction mixture comprising two enantiomeric pairs: (S)-α-cyano-4-fluoro-3-phenoxybenzyl (1R,3R)-3-(2,2-dichlorovinyl)-2,2-dimethylcyclopropanecarboxylate and (R)-α-cyano-4-fluoro-3-phenoxybenzyl (1S,3S)-3-(2,2-dichlorovinyl)-2,2-dimethylcyclopropanecarboxylate (II) with (S)-α-cyano-4-fluoro-3-phenoxybenzyl (1R,3S)-3-(2,2-dichlorovinyl)-2,2-dimethylcyclopropanecarboxylate and (R)-α-cyano-4-fluoro-3-phenoxybenzyl (1S,3R)-3-(2,2-dichlorovinyl)-2,2-dimethylcyclopropanecarboxylate (IV) in ratio c. 1:2; beta-cypermethrin, A reaction mixture comprising the enantiomeric pair (R)-α-cyano-3-phenoxybenzyl (1S,3S)-3-(2,2-dichlorovinyl)-2,2-dimethylcyclopropanecarboxylate and (S)-α-cyano-3-phenoxybenzyl (1R,3R)-3-(2,2-dichlorovinyl)-2,2-dimethylcyclopropanecarboxylate with the enantiomeric pair (R)-α-cyano-3-phenoxybenzyl (1S,3R)-3-(2,2-dichlorovinyl)-2,2-dimethylcyclopropanecarboxylate and (5)-α-cyano-3-phenoxybenzyl (1R,3S)-3-(2,2-dichlorovinyl)-2,2-dimethylcyclopropanecarboxylate in ratio c. 2:3; bifenthrin, 2-methylbiphenyl-3-ylmethyl (Z)-(1RS,3RS)-3-(2-chloro-3,3,3-trifluoroprop-1-enyl)-2,2-dimethylcyclopropanecarboxylate; bioallethrin, (RS)-3-allyl-2-methyl-4-oxocyclopent-2-enyl (+)-trans-Page chrysanthemate; esdepalléthrine, (S)-3-allyl-2-methyl-4-oxocyclopent-2-enyl (+)-trans-chrysanthemate; bioresmethrin, 5-benzyl-3-furylmethyl (+)-trans-chrysanthemate; cycloprothrin, (RS)-α-cyano-3-phenoxybenzyl (RS)-2,2-dichloro-1-(4-ethoxyphenyl)cyclopropane carboxylate; cyfluthrin, (RS)-α-cyano-4-fluoro-3-phenoxybenzyl (1RS,3RS;1RS,3SR)-3-(2,2-dichlorovinyl)-2,2-dimethylcyclopropanecarboxylate; cyhalothrin, (RS)-α-cyano-3-phenoxybenzyl (Z)-(1RS,3RS)-3-(2-chloro-3,3,3-trifluoroprop-1-enyl)-2,2-dimethylcyclopropanecarboxylate; cypermethrin, (RS)-α-cyano-3-phenoxybenzyl (1RS,3RS;1RS,3SR)-3-(2,2-dichlorovinyl)-2,2-dimethylcyclopropanecarboxylate; cyphenothrin, (RS)-α-cyano-3-phenoxybenzyl (1RS,3RS;1RS,3SR)-2,2-dimethyl-3-(2-methylprop-1-enyl)cyclopropane carboxylate; deltamethrin, (S)-α-cyano-3-phenoxybenzyl (1R,3R)-3-(2,2-dibromovinyl)-2,2-dimethylcyclopropanecarboxylate; empenthrin, (E)-(RS)-1-ethynyl-2-methylpent-2-enyl (1R,3RS;1R,3SR)-2,2-dimethyl-3-(2-methylprop-1-enyl)cyclopropane carboxylate; esfenvalerate, (S)-α-cyano-3-phenoxybenzyl (S)-2-(4-chlorophenyl)-3-methylbutyrate; etofenprox, 2-(4-ethoxyphenyl)-2-methylpropyl 3-phenoxybenzyl ether; fenpropathrin, (RS)-α-cyano-3-phenoxybenzyl 2,2,3,3-tetramethylcyclopropanecarboxylate; fenvalerate, (RS)-α-cyano-3-phenoxybenzyl (RS)-2-(4-chlorophenyl)-3-methylbutyrate; flucythrinate, (RS)-α-cyano-3-phenoxybenzyl (S)-2-(4-difluoromethoxyphenyl)-3-methylbutyrate; flumethrin, α-cyano-4-fluoro-3-phenoxybenzyl 3-(β,4-dichlorostyryl)-2,2-dimethylcyclopropanecarboxylate; gamma-cyhalothrin, (S)-α-cyano-3-phenoxybenzyl (Z)-(1R,3R)-3-(2-chloro-3,3,3-trifluoroprop-1-enyl)-2,2-dimethylcyclopropanecarboxylate; halfenprox, 2-(4-bromodifluoromethoxyphenyl)-2-methylpropyl 3-phenoxybenzyl ether; imiprothrin, A mixture containing 20% of 2,5-dioxo-3-prop-2-ynylimidazolidin-1-ylmethyl (1R,3S)-2,2-dimethyl-3-(2-methylprop-1-enyl)cyclopropane carboxylate and 80% of 2,5-dioxo-3-prop-2-ynylimidazolidin-1-ylmethyl (1R,3R)-2,2-dimethyl-3-(2-methylprop-1-enyl)cyclopropane carboxylate; lambda-cyhalothrin, a reaction product comprising equal quantities of (S)-α-cyano-3-phenoxybenzyl (Z)-(1R,3R)-3-(2-chloro-3,3,3-trifluoroprop-1-enyl)-2,2-dimethylcyclopropanecarboxylate and (R)-α-cyano-3-phenoxybenzyl (Z)-(1S,3S)-3-(2-chloro-3,3,3-trifluoroprop-1-enyl)-2,2-dimethylcyclopropanecarboxylate; methothrin, 4-(methoxymethyl)benzyl (1RS)-cis,trans-2,2-dimethyl-3-(2-methylprop-1-enyl)cyclopropane carboxylate; metofluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate; permethrin, 3-phenoxybenzyl (1RS,3RS;1RS,3SR)-3-(2,2-dichlorovinyl)-2,2-dimethylcyclopropanecarboxylate; phenothrin, 3-phenoxybenzyl (1RS,3RS;1RS,3SR)-2,2-dimethyl-3-(2-methylprop-1-enyl)cyclopropane carboxylate; prallethrin, (RS)-2-methyl-4-oxo-3-prop-2-ynylcyclopent-2-enyl (1RS,3RS;1RS,3SR)-2,2-dimethyl-3-(2-methylprop-1-enyl)cyclopropane carboxylate; resmethrin, 5-benzyl-3-furylmethyl (1RS,3RS;1RS,3SR)-2,2-dimethyl-3-(2-methylprop-1-enyl)cyclopropane carboxylate; RU15525, 5-benzyl-3-furylmethyl (E)-(1R,3S)-2,2-dimethyl-3-(2-oxothiolan-3-ylidenemethyl)cyclopropane carboxylate; Silafluofen, (4-ethoxyphenyl)[3-(4-fluoro-3-phenoxyphenyl)propyl](dimethyl)silane; tau-fluvalinate, (RS)-α-cyano-3-phenoxybenzyl N-(2-chloro-α,α,α-trifluoro-p-tolyl)-D-valinate; tefluthrin, 2,3,5,6-tetrafluoro-4-methylbenzyl (Z)-(1RS,3RS)-3-(2-chloro-3,3,3-trifluoroprop-1-enyl)-2,2-dimethylcyclopropanecarboxylate; tetramethrin, cyclohex-1-ene-1,2-dicarboximidomethyl (1RS,3RS;1RS,3SR)-2,2-dimethyl-3-(2-methylprop-1-enyl)cyclopropane carboxylate; tetramethrin[(1R)-isomers], cyclohex-1-ene-1,2-dicarboximidomethyl (1R,3R;1R,3S)-2,2-dimethyl-3-(2-methylprop-1-enyl)cyclopropane carboxylate; theta-cypermethrin, A mixture of the enantiomers (R)-α-cyano-3-phenoxybenzyl (1S,3R)-3-(2,2-dichlorovinyl)-2,2-dimethylcyclopropanecarboxylate and (S)-α-cyano-3-phenoxybenzyl (1R,3S)-3-(2,2-dichlorovinyl)-2,2-dimethylcyclopropanecarboxylate in the ratio 1:1; tralomethrin, (S)-α-cyano-3-phenoxybenzyl (1R,3S)-2,2-dimethyl-3-[(RS)-1,2,2,2-tetrabromoethyl]cyclopropane carboxylate; transfluthrin, 2,3,5,6-tetrafluorobenzyl (1R,3S)-3-(2,2-dichlorovinyl)-2,2-dimethylcyclopropanecarboxylate; zeta-cypermethrin, A mixture of the stereoisomers (S)-α-cyano-3-phenoxybenzyl (1RS,3RS; 1RS,3SR)-3-(2,2-dichlorovinyl)-2,2-dimethylcyclopropanecarboxylate where the ratio of the (S);(1RS,3RS) isomeric pair to the (S);(1RS,3SR) isomeric pair lies in the ratio range 45-55 to 55-45; ZXI8901, 3-(4-bromophenoxy)-α-cyanobenzyl 2-[4-(difluoromethoxy)phenyl]-3-methylbutanoate, and other isomeric mixtures not explicitly described above. In some embodiments a pyrethroid compound can be a compound that falls under Insecticide Resistance Action Committee Mode of Action Classification Class 3A (sodium channel modulators; pyrethroids, pyrethrins).

Nanoparticles of Polymer-Associated Active Ingredient

As used herein, the terms "nanoparticles of polymer-associated active ingredient", "nanoparticles of polymer-associated pyrethroid compound" or "active ingredient associated with polymer nanoparticles" refer to nanoparticles comprising one or more collapsed polymers that are associated with the active ingredient. In some embodiments the collapsed polymers are cross-linked. As discussed below, in some embodiments, our formulations may include aggregates of nanoparticles. Exemplary polymers and methods of preparing nanoparticles of polymer-associated active ingredient are described more fully below.

In some embodiments, the active ingredient is associated with preformed polymer nanoparticles. The associating step may involve dispersing the polymer nanoparticles in a first solvent and then dispersing the active ingredient in a second solvent that is miscible or partially miscible with the first solvent, mixing the two dispersions and then either removing the second or first solvent from the final mixture. In some embodiments, all the solvent is removed by vacuum evaporation, freeze drying or spray drying. The associating step may also involve dispersing both the polymer nanoparticles and active ingredients in a common solvent and removing all or a portion of the common solvent from the final mixture.

In some embodiments, the associating step may involve milling the active ingredient in the presence of pre-formed nanoparticles. It is surprising that if the active ingredient alone is milled under these conditions, the resulting particle size is significantly larger than if it is milled in the presence of pre-formed polymer nanoparticles. In general, size reduction processes such as milling do not enable the production of particle sizes that are produced via milling in the presence of nanoparticles of the current disclosure. Without wishing to be bound by any theory, it is thought that interaction between the active ingredient and the nanoparticles during the milling process facilitates the production of smaller particles than would be formed via milling in the absence of the nanoparticles.

Non-limiting examples of milling methods that may be used for the association step can be found in U.S. Pat. No. 6,604,698 and include ball milling, bead milling, jet milling, media milling, and homogenization, as well as other milling methods known to those of skill in the art. Non-limiting examples of mills that can be for the association step include attritor mills, ball mills, colloid mills, high pressure homogenizers, horizontal mills, jet mills, swinging mills, and vibratory mills. In some embodiments, the associating step may involve milling the active ingredient in the presence of pre-formed polymer nanoparticles and an aqueous phase. In some embodiments, the associating step may involve wet or dry milling of the active ingredient in the presence of pre-formed nanoparticles. In some embodiments, the association step may involve milling the active ingredient and pre-formed polymer nanoparticles in the presence of one or more formulating agents.

In general, the active ingredient may be associated with regions of the polymer nanoparticle that elicit a chemical or physical interaction with the active ingredient. Chemical interactions can include hydrophobic interactions, affinity pair interactions, H-bonding, and van der Waals forces. Physical interactions can include entanglement in polymer chains or inclusion within the polymer nanoparticle structure. The active ingredient can be associated in the interior of the polymer nanoparticle, on the surface of the polymer nanoparticle, or both the surface and the interior of the polymer nanoparticle. Furthermore, the type of association interactions between the active ingredient and the polymer nanoparticle can be probed using spectroscopic techniques such as NMR, IR, UV-vis, and emission spectroscopies. For example, in cases where the pyrethroid active ingredient is normally crystalline when not associated with the polymer nanoparticles, the nanoparticles of polymer-associated pyrethroid compounds typically do not show the endothermic melting peak or show a reduced endothermic melting peak of the pure crystalline active ingredient as seen in differential thermal analysis (DTA) or differential scanning calorimetry (DSC) measurements.

Nanoparticles of polymer-associated active ingredients can be prepared with a range of average diameters, e.g., between about 1 nm and about 500 nm. The size of the nanoparticles can be adjusted in part by varying the size and number of polymers that are included in the nanoparticles. In some embodiments, the average diameter ranges from about 1 nm to about 10 nm, from about 1 nm to about 20 nm, from about 1 nm to about 30 nm, from about 1 nm to about 50 nm, from about 10 nm to about 50 nm, from about 10 nm to about 100 nm, from about 20 nm to about 100 nm, from about 20 nm to about 100 nm, from about 50 nm to about 200 nm, from about 50 nm to about 250 nm, from about 50 nm to about 300 nm, from about 100 nm to about 250 nm, from about 100 nm to about 300 nm, from about 200 nm to about 300 nm, from about 200 nm to about 500 nm, from about 250 nm to about 500 nm, and from about 300 nm to about 500 nm. These and other average diameters described herein are based on volume average particle sizes that were measured in solution by dynamic light scattering on a Malvern Zetasizer ZS in CIPAC D water, 0.1M NaCl, or in deionized water at 200 ppm active concentration. Various forms of microscopies can also be used to visualize the sizes of the nanoparticles such as atomic force microscopy (AFM), transmission electron microscopy (TEM), scanning electron microscopy (SEM) and optical microscopy.

As mentioned above, in some embodiments, the formulation may comprise aggregates of nanoparticles comprising polymer-associated active ingredients. In some embodiments, these aggregates can be loose aggregates that can be separated into isolated nanoparticles by vigorous mixing, sonication, dilution, etc. In some embodiments, these aggregates are hard aggregates that cannot be separated using simple physical techniques. In some embodiments, the aggregates are aggregated due to interactions between active ingredients exposed on the surface of the nanoparticles. In some embodiments, the aggregates have an average particle size between about 10 nm and about 5,000 nm when dispersed in water under suitable conditions. In some embodiments, the aggregates have an average particle size between about 10 nm and about 1,000 nm. In some embodiments, the aggregates have an average particle size between about 10 nm and about 500 nm. In some embodiments, the aggregates have an average particle size between about 10 nm and about 300 nm. In some embodiments, the aggregates have an average particle size between about 10 nm and about 200 nm. In some embodiments, the aggregates have an average particle size between about 50 nm and about 5,000 nm. In some embodiments, the aggregates have an average particle size between about 50 nm and about 1,000 nm. In some embodiments, the aggregates have an average particle size between about 50 nm and about 500 nm. In some embodiments, the aggregates have an average particle size between about 50 nm and about 300 nm. In some embodiments, the aggregates have an average particle size between about 50 nm and about 200 nm. In some embodiments, the aggregates have an average particle size between about 100 nm and about 5,000 nm. In some embodiments, the aggregates have an average particle size between about 100 nm and about 1,000 nm. In some embodiments, the aggregates have an average particle size between about 100 nm and about 500 nm. In some embodiments, the aggregates have an average particle size between about 100 nm and about 300 nm. In some embodiments, the aggregates have an average particle size between about 100 nm and about 200 nm. In some embodiments, the aggregates have an average particle size between about 500 nm and about 5000 nm. In some embodiments, the aggregates have an average particle size between about 500 nm and about 1000 nm. In some embodiments, the aggregates have an average particle size between about 1000 nm and about 5000 nm. Particle size can be measured by the techniques described above.

As described in detail in the examples, in some embodiments, pre-formed polymer nanoparticles that have been associated with active ingredient to generate nanoparticles or aggregates of nanoparticles of polymer-associated active ingredients (associated nanoparticles) can be recovered after extraction of the active ingredient. In some embodiments, the active ingredient can be extracted from nanoparticles or aggregates of nanoparticles of polymer-associated active ingredient by dispersing the associated nanoparticles in a solvent that dissolves the active ingredient but that is known to disperse the un-associated, preformed nanoparticles poorly or not at all. In some embodiments, after extraction and separation, the insoluble nanoparticles that are recovered have a size that is smaller than the nanoparticles or aggregates of nanoparticles of polymer-associated active ingredients as measured by DLS. In some embodiments, after extraction and separation, the insoluble nanoparticles that are recovered have a size that is similar or substantially the same as the size of original pre-formed polymer nanoparticles (prior to association) as measured by DLS. In some embodiments, the nanoparticles are prepared from poly (methacrylic acid-co-ethyl acrylate). In some embodiments, the active ingredient is bifenthrin. In some embodiments, the extraction solvent is acetonitrile.

It should be understood that the association step to generate nanoparticles of polymer associated active ingredient need not necessarily lead to association of the entire fraction the active ingredient in the sample with pre-formed polymer nanoparticles (not all molecules of the active ingredient in the sample must be associated with polymer nanoparticles after the association step). Likewise, the association step need not necessarily lead to the association of the entire fraction of the pre-formed nanoparticles in the sample with active ingredient (not all nanoparticle molecules in the sample must be associated with the active ingredient after the association step).

Similarly, in formulations comprising nanoparticles of polymer-associated active ingredient, the entire fraction of active ingredient in the formulation need not be associated with pre-formed polymer nanoparticles (not all molecules of the active ingredient in the sample must be associated with polymer nanoparticles in the formulation). Likewise, in formulations comprising nanoparticles of polymer-associated active ingredient, the entire fraction of pre-formed polymer nanoparticles in the formulation need not be associated with active ingredient (not all of nanoparticle molecules in the sample must be associated with the active ingredient in the formulation).

In some embodiments, the nanoparticles are prepared using a polymer that is a polyelectrolyte. Polyelectrolytes are polymers that contain monomer units of ionized or ionizable functional groups, they can be linear, branched, hyperbranched or dendrimeric, and they can be synthetic or naturally occurring. Ionizable functional groups are functional groups that can be rendered charged by adjusting solution conditions, while ionized functional group refers to chemical functional groups that are charged regardless of solution conditions. The ionized or ionizable functional group can be cationic or anionic, and can be continuous along the entire polymer chain (e.g., in a homopolymer), or can have different functional groups dispersed along the polymer chain, as in the case of a co-polymer (e.g., a random co-polymer). In some embodiments, the polymer can be made up of monomer units that contain functional groups that are either anionic, cationic, both anionic and cationic, and can also include other monomer units that impart a specific desirable property to the polymer.

In some embodiments, the polyelectrolyte is a homopolymer. Non limiting examples of homopolymer polyelectrolytes are: poly(acrylic acid), poly(methacrylic acid), poly (styrene sulfonate), poly(ethyleneimine), chitosan, poly (dimethylammonium chloride), poly(allylamine hydrochloride), and carboxymethyl cellulose.

In some embodiments, the polyelectrolyte is a co-polymer. In some embodiments, the polyelectrolyte co-polymer is poly(methacrylic acid-co-ethyl acrylate); poly(methacrylic acid-co-styrene); poly(methacrylic acid-co-butyl-methacrylate); poly[acrylic acid-co-poly(ethylene glycol) methyl ether methacrylate]; or poly(n-butylmethacrylcate-co-methacrylic acid).

In some embodiments, the polyelectrolyte can be made from one or more monomer units to form homopolymers, copolymers or graft copolymers of: carboxylic acids including acrylic acid, methacrylic acid, itaconic acid, and maleic acid; polyoxyethylenes or polyethyleneoxide; and unsaturated ethylenic mono or dicarboxylic acids; lactic acids; amino acids; amines including dimethlyammonium chloride, allylamine hydrochloride; along with other monomers such including methacrylic acid; ethyleneimine; ethylene; ethylene glycol; ethylene oxide acrylates including methyl acrylate, ethyl acrylate, propyl acrylate, n-butyl acrylate ("BA"), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate and partially hydrolyzed poly(vinyl acetate), vinylversatate, vinylpropionate, vinylformamide, vinylacetamide, vinylpyridines, and vinyllimidazole; vinylnapthalene, vinylnaphthalene sulfonate, vinylpyrrolidone, vinyl alcohol; aminoalkyls including aminoalkylacrylates, aminoalkyls-methacrylates, and aminoalkyl(meth)acrylamides; styrenes including styrene sulfonate, 2-Acrylamido-2-methylpropane sulfonic acid; d-glucosamine; glucaronic acid-N-acetylglucosamine; N-isopropylacrylamide; vinyl amine. In some embodiments, the polyelectrolyte polymer can include groups derived from polysaccharides such as dextran, gums, cellulose, or carboxymethyl cellulose In some embodiments, the mass ratio of methacrylic acid to ethyl acrylate in the poly(methacrylic acid co-ethyl acrylate) polymer is between about 50:50 and about 95:5. In some embodiments, the mass ratio of methacrylic acid to ethyl acrylate in the poly(methacrylic acid co-ethyl acrylate) polymer is between about 70:30 and about 95:5. In some embodiments, the mass ratio of methacrylic acid to ethyl acrylate in the poly(methacrylic acid co-ethyl acrylate) polymer is between about 80:20 and about 95:5. In some embodiments, the mass ratio of methacrylic acid to ethyl acrylate in the poly(methacrylic acid co-ethyl acrylate) polymer is between about 85:15 and about 95:5.

In some embodiments, the mass ratio of methacrylic acid to styrene in the poly(methacrylic acid-co-styrene) polymer is between about 50:50 and about 95:5. In some embodiments, the mass ratio of methacrylic acid to styrene in the poly(methacrylic acid-co-styrene) polymer is between about 70:30 and about 95:5. In some embodiments, the mass ratio of methacrylic acid to styrene in the poly(methacrylic acid-co-styrene) polymer is between about 80:20 and about 95:5. In some embodiments, the mass ratio of methacrylic acid to styrene in the poly(methacrylic acid-co-styrene) polymer is between about 85:15 and about 95:5.

In some embodiments, the mass ratio of methacrylic acid to butyl methacrylate in the poly(methacrylic acid co-butylmethacrylate) polymer is between about 50:50 and about 95:5. In some embodiments, the mass ratio of methacrylic acid to butyl methacrylate in the poly(methacrylic acid co-butylmethacrylate) polymer is between about 70:30 and about 95:5. In some embodiments, the mass ratio of methacrylic acid to butyl methacrylate in the poly(methacrylic acid co-butylmethacrylate) polymer is between about 80:20 and about 95:5. In some embodiments, the mass ratio of methacrylic acid to butyl methacrylate in the poly(methacrylic acid co-butylmethacrylate) polymer is between about 85:15 and about 95:5.

In some embodiments, the homo or co-polymer is water soluble at pH 7. In some embodiments, the polymer has solubility in water above about 1 weight %. In some embodiments, the polymer has solubility in water above about 2 weight %. In some embodiments, the polymer has solubility in water above about 3 weight %. In some embodiments, the polymer has solubility in water above about 4 weight %. In some embodiments, the polymer has solubility in water above about 5 weight %. In some embodiments, the polymer has solubility in water above about 10 weight %. In some embodiments, the polymer has solubility in water above about 20 weight %. In some embodiments, the polymer has solubility in water above about 30 weight %. In some embodiments, the polymer has solubility in water between about 1 and about 30 weight %. In some embodiments, the polymer has solubility in water between about 1 and about 10 weight %. In some embodiments, the polymer has solubility in water between about 5 and about 10 weight %. In some embodiments, the polymer has solubility in water between about 10 and about 30 weight %. In some embodiments the solubility of the polymer in water can also be adjusted by adjusting pH or other solution conditions in water.

In some embodiments, the polyelectrolyte polymer has a weight average ($M_w$) molecular weight between about 100,000 and about 4,000,000 Daltons. In some embodiments, the polyelectrolyte polymer has a weight average molecular weight of between about 100,000 and about 2,000,000 Daltons. In some embodiments, the polyelectrolyte polymer has a weight average molecular weight of between about 100,000 and about 1,000,000 Daltons. In some embodiments, the polyelectrolyte polymer has a weight average molecular weight of between about 100,000 and about 750,000 Daltons. In some embodiments, the polyelectrolyte polymer has a weight average molecular weight of between about 100,000 and about 500,000 Daltons. In some embodiments, the polyelectrolyte polymer has a weight average molecular weight of between about 100,000 and about 200,000 Daltons. In some embodiments, the polyelectrolyte polymer has a weight average molecular weight of between about 200,000 and about 2,000,000 Daltons. In some embodiments, the polyelectrolyte polymer has a weight average molecular weight of between about 200,000 and about 1,000,000 Daltons. In some embodiments, the polyelectrolyte polymer has a weight average molecular weight of between about 200,000 and about 500,000 Daltons. In some embodiments, the polyelectrolyte polymer has a weight average molecular weight of between about 300,000 and about 2,000,000 Daltons. In some embodiments, the polyelectrolyte polymer has a weight average molecular weight of between about 300,000 and about 1,000,000 Daltons. In some embodiments, the polyelectrolyte polymer has a weight average molecular weight of between about 300,000 and about 500,000 Daltons.

In some embodiments, the apparent molecular weight of the polyelectrolyte polymer (e.g. the molecular weight determined via certain analytical measurements such as size exclusion chromatography or DLS) is lower than the actual molecular weight of a polymer due to crosslinking within the polymer. In some embodiments, a crosslinked polyelectrolyte polymer of the present disclosure might have a higher actual molecular weight than the experimentally determined apparent molecular weight. In some embodiments, a crosslinked polyelectrolyte polymer of the present disclosure might be a high molecular weight polymer despite having a low apparent molecular weight.

Nanoparticles of polymer-associated active ingredients and/or aggregates of these nanoparticles can be part of a formulation in different amounts. The final amount will depend on many factors including the type of formulation (e.g., liquid or solid, granule or powder, concentrated or not, etc.). In some instances the nanoparticles (including both the polymer and active ingredient components) make up between about 1 and about 98 weight % of the total formulation. In some embodiments, the nanoparticles make up between about 1 and about 90 weight % of the total formulation. In some embodiments, the nanoparticles make up between about 1 and about 75 weight % of the total formulation. In some embodiments, the nanoparticles make up between about 1 and about 50 weight % of the total formulation. In some embodiments, the nanoparticles make up between about 1 and about 30 weight % of the total formulation. In some embodiments, the nanoparticles make up between about 1 and about 25 weight % of the total formulation. In some embodiments, the nanoparticles make up between about 1 and about 10 weight % of the total formulation. In some embodiments, the nanoparticles make up between about 10 and about 25 weight % of the total formulation. In some embodiments, the nanoparticles make up between about 10 and about 30 weight % of the total formulation. In some embodiments, the nanoparticles make up between about 10 and about 50 weight % of the total formulation. In some embodiments, the nanoparticles make up between about 10 and about 75 weight % of the total formulation. In some embodiments, the nanoparticles make up between about 10 and about 90 weight % of the total formulation. In some embodiments, the nanoparticles make up between about 10 and about 98 weight % of the total formulation. In some embodiments, the nanoparticles make up between about 25 and about 50 weight % of the total formulation. In some embodiments, the nanoparticles make up between about 25 and about 75 weight % of the total formulation. In some embodiments, the nanoparticles make up between about 25 and about 90 weight % of the total formulation. In some embodiments, the nanoparticles make up between about 30 and about 98 weight % of the total formulation. In some embodiments, the nanoparticles make up between about 50 and about 90 weight % of the total formulation. In some embodiments, the nanoparticles make up between about 50 and about 98 weight % of the total formulation. In some embodiments, the nanoparticles make up between about 75 and about 90 weight % of the total formulation. In some embodiments, the nanoparticles make up between about 75 and about 98 weight % of the total formulation.

In some embodiments, the nanoparticles of polymer-associated active ingredients are prepared according to a method disclosed in United States Patent Application Publication No. 20100210465, the entire contents of which are incorporated herein by reference. In some embodiments, polymer nanoparticles without active ingredients are made by collapse of a polyelectrolyte with a collapsing agent and then rendering the collapsed conformation permanent by intra-particle cross-linking. The active ingredient is then associated with this preformed polymer nanoparticle. In some embodiments, the formulation contains the same amount (by weight) of active ingredient and polymer, while in other embodiments the ratio of active ingredient to polymer (by weight) can be between about 1:10 and about 10:1, between about 1:10 and about 1:5, between about 1:5 and about 1:4, between about 1:4 and about 1:3, between about 1:3 and about 1:2, between about 1:2 and about 1:1, between about 1:5 and about 1:1, between about 5:1 and about 1:1, between about 2:1 and about 1:1, between about 3:1 and about 2:1, between about 4:1 and about 3:1, between about 5:1 and about 4:1, between about 10:1 and about 5:1, between about 1:3 and about 3:1, between about 5:1 and about 1:1, between about 1:5 and about 5:1, or between about 1:2 and about 2:1.

As noted above, in some embodiments, the associating step may involve dispersing the polymer nanoparticles in a first solvent, dispersing the active ingredient in a second solvent that is miscible or partially miscible with the first solvent, mixing the two dispersions and then either removing the second or first solvent from the final mixture. Alternatively, in some embodiments, the associating step may involve dispersing both the polymer nanoparticles and active ingredient in a common solvent and removing all or a portion of the common solvent from the final mixture. The final form of the nanoparticles of polymer-associated active ingredient can be either a dispersion in a common solvent or a dried solid. The common solvent is typically one that is capable of swelling the polymer nanoparticles as well as dissolving the active ingredient at a concentration of at least about 10 mg/mL, e.g., at least about 20 mg/mL. The polymer nanoparticles are typically dispersed in the common solvent at a concentration of at least about 10 mg/mL, e.g., at least about 20 mg/mL. In some embodiments, the common solvent is an alcohol (either long or short chain), preferably methanol or ethanol. In some embodiments the common solvent is selected from alkenes, alkanes, alkynes, phenols, hydrocarbons, chlorinated hydrocarbons, ketones, water, and ethers. In some embodiments, the common solvent is a mixture of two or more different solvents that are miscible or partially miscible with each other. Some or all of the common solvent is removed from the dispersion of polymer nanoparticles and active ingredients by either direct evaporation or evaporation under reduced pressure. The dispersion can be dried by a range of processes known by a practitioner of the art such as lyophilization (freeze-drying), spray-drying, tray-drying, evaporation, jet drying, or other methods to obtain the nanoparticles of polymers-associated with active ingredients. In general, the amount of solvent that is removed from the dispersion described above will depend on the final type of formulation that is desired. This is illustrated further in the Examples and in the general description of specific formulations.

In some instances the solids content (including both the polymer and active ingredient components as well as other solid form formulating agents) of the formulation is between about 1 and about 98 weight % of the total formulation. In some embodiments, the solids content of the formulation is between about 1 and about 90 weight % of the total formulation. In some embodiments, the solids content of the formulation is between about 1 and about 75 weight % of the total formulation. In some embodiments, the solids content of the formulation is between about 1 and about 50 weight % of the total formulation. In some embodiments, the solids content of the formulation is between about 1 and about 30 weight % of the total formulation. In some embodiments, the solids content of the formulation is between about 1 and about 25 weight % of the total formulation. In some embodiments, the solids content of the formulation is between about 1 and about 10 weight % of the total formulation. In some embodiments, the solids content of the formulation is between about 10 and about 25 weight % of the total formulation. In some embodiments, the solids content of the formulation is between about 10 and about 30 weight % of the total formulation. In some embodiments, the solids content of the formulation is between about 10 and about 50 weight % of the total formulation. In some embodiments, the solids content of the formulation is between about 10 and about 75 weight % of the total formulation. In some embodiments, the solids content of the formulation is between about 10 and about 90 weight % of the total formulation. In some embodiments, the solids content of the formulation is between about 10 and about 98 weight % of the total formulation. In some embodiments, the solids content of the formulation is between about 25 and about 50 weight % of the total formulation. In some embodiments, the solids content of the formulation is between about 25 and about 75 weight % of the total formulation. In some embodiments, the solids content of the formulation is between about 25 and about 90 weight % of the total formulation. In some embodiments, the solids content of the formulation is between about 30 and about 98 weight % of the total formulation. In some embodiments, the solids content of the formulation is between about 50 and about 90 weight % of the total formulation. In some embodiments, the solids content of the formulation is between about 50 and about 98 weight % of the total formulation. In some embodiments, the solids content of the formulation is between about 75 and about 90 weight % of the total formulation. In some embodiments, the solids content of the formulation is between about 75 and about 98 weight % of the total formulation.

Formulating Agents

As used herein, the term "formulating agents" refers to other materials used in the formulation other than the nanoparticles of polymer-associated active ingredient. Formulating agents can include, but are not limited to, compounds that can act as a dispersants or wetting agents, inert fillers, solvents, surfactants, anti-freezing agents, anti-settling agents or thickeners, disintegrants, and preservatives.

In some embodiments, a formulation may include a dispersant or wetting agent or both. In some embodiments the same compound may act as both a dispersant and a wetting agent. A dispersant is a compound that helps the nanoparticles disperse in water. Without wishing to be bound by any theory, dispersants are thought to achieve this result by absorbing on to the surface of the nanoparticles and thereby limiting re-aggregation. Wetting agents increase the spreading or penetration power of a liquid such as water onto a powder or granular formulation. Without wishing to be bound by any theory, wetting agents are thought to achieve this result by reducing the interfacial tension between the liquid and the substrate surface.

In a similar manner, some formulating agents may demonstrate multiple functionality. The categories and listings of specific agents below are not mutually exclusive. For example, fumed silica, described below in the thickener/anti-settling agent and anti-caking agent sections, is typically used for these functions. In some embodiments, however, fumed silica demonstrates the functionality of a wetting agent and/or dispersant. Specific formulating agents listed below are categorized based on their primary functionality, however, it is to be understood that particular formulating agents may exhibit multiple functions. Certain formulation ingredients display multiple functionalities and synergies with other formulating agents and may demonstrate superior properties in a particular formulation but not in another formulation.

In some embodiments, a dispersant or wetting agent is selected from organosilicones (e.g., SYLGARD 309 from Dow Corning Corporation or SILWET L77 from Union Carbide Corporation) including polyalkylene oxide modified polydimethylsiloxane (SILWET L7607 from Union Carbide Corporation), methylated seed oil, and ethylated seed oil (e.g., SCOIL from Agsco or HASTEN from Wilfarm), alkylpolyoxyethylene ethers (e.g., ACTIVATOR 90), alkylarylalolates (e.g., APSA 20), alkylphenol ethoxylate and alcohol alkoxylate surfactants (e.g., products sold by Huntsman), fatty acid, fatty ester and fatty amine ethoxylates (e.g., products sold by Huntsman), products sold by Cognis such as sorbitan and ethoxylated sorbitan esters, ethoxylated vegetable oils, alkyl, glycol and glycerol esters and glycol ethers, tristyrylphenol ethoxylates, anionic surfactants such as sulfonates, such as sulfosuccinates, alkylaryl sulphonates, alkyl napthalene sulfonates (e.g., products sold by Adjuvants Unlimited), calcium alkyl benzene sulphonates, and phosphate esters (e.g., products sold by Huntsman Chemical or BASF), as salts of sodium, potassium, ammonium, magnesium, triethanolamine (TEA), etc. Other specific examples of the above sulfates include ammonium lauryl sulfate, magnesium lauryl sulfate, sodium 2-ethyl-hexyl sulfate, sodium actyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate. Other examples of dispersants and wetting agents include, sulfo succinamates, disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid; dihexyl ester of sodium sulfosuccinic acid; and dioctyl esters of sodium sulfosuccinic acid; castor oil and fatty amine ethoxylates, including sodium, potassium, magnesium or ammonium salts thereof.

Dispersants and wetting agents also include natural emulsifiers, such as lecithin, fatty acids (including sodium, potassium or ammonium salts thereof) and ethanolamides and glycerides of fatty acids, such as coconut diethanolamide and coconut mono- and diglycerides. Dispersants and wetting agents also include sodium polycarboxylate (commercially available as Geropon TA/72); sodium salt of naphthalene sulfonate condensate (commercially available as Morwet (D425, D809, D390, EFW); calcium naphthalene sulfonates (commercially available as DAXAD 19LCAD); sodium lignosulfonates and modified sodium lignosulfonates; aliphatic alcohol ethoxylates; ethoxylated tridecyl alcohols (commercially available as Rhodasurf (BC420, BC610, BC720, BC 840); Ethoxylated tristeryl phenols (commercially available as Soprophor BSU); sodium methyl oleyl taurate (commercially available as Geropon T77); tristyrylphenol ethoxylates and esters; ethylene oxide-propylene oxide block copolymers; non-ionic block copolymers (commercially available as Atlox (4912). Examples of dispersants and wetting agents include, but are not limited to, sodium dodecylbenzene sulfonate; N-oleyl N-methyl taurate; 1,4-dioctoxy-1,4-dioxo-butane-2-sulfonic acid; sodium lauryl sulphate; sodium dioctyl sulphosuccinate; aliphatic alcohol ethoxylates; nonylphenol ethoxylates. Dispersants and wetting agents also include sodium taurates; and sodium or ammonium salts of maleic anhydride copolymers, lignosulfonic acid formulations or condensed sulfonate sodium, potassium, magnesium or ammonium salts, polyvinylpyrrolidone (available commercially as POLYPLASDONE XL-10 from International Specialty Products or as KOLLIDON C1 M-10 from BASF Corporation), polyvinyl alcohols, modified or unmodified starches, methylcellulose, hydroxyethyl or hydroxypropyl methylcellulose, carboxymethyl methylcellulose, or combinations, such as a mixture of either lignosulfonic acid formulations or condensed sulfonate sodium, potassium, magnesium or ammonium salts with polyvinylpyrrolidone (PVP).

In some embodiments, the dispersants and wetting agents can combine to make up between about 1 and about 30 weight % of the formulation. For example, dispersants and wetting agents can make up between about 1 and about 20 weight %, about 1 and about 10 weight %, between about 1 and about 5 weight %, between about 1 and about 3 weight %, between about 2 and about 30 weight %, between about 2 and about 20 weight %, between about 2 and about 10 weight %, between about 3 and about 30 weight %, between about 3 and about 20 weight %, between about 3 and about 10 weight %, between about 3 and about 5 weight %, between about 5 and about 30 weight %, between about 5 and about 20 weight %, between about 5 and about 10 weight % of the formulation. In some embodiments, dispersants or wetting agents can make up between about 0.1 and 1 weight % of the formulation. In some embodiments, a formulation may include an inert filler. For example, an inert filler may be included to produce or promote cohesion in forming a wettable granule formulation. An inert filler may also be included to give the formulation a certain active loading, density, or other similar physical properties. Non limiting examples of inert fillers that may be used in a formulation include bentonite clay, carbohydrates, proteins, lipids synthetic polymers, glycolipids, glycoproteins, lipoproteins, lignin, lignin derivatives, and combinations thereof. In a preferred embodiment the inert filler is a lignin derivative and is optionally calcium lignosulfonate. In some embodiments, the inert filler is selected from the group consisting of: monosaccharides, disaccharides, oligosaccharides, polysaccharides and combinations thereof. Specific carbohydrate inert fillers illustratively include glucose, mannose, fructose, galactose, sucrose, lactose, maltose, xylose, arabinose, trehalose and mixtures thereof such as corn syrup; sugar alcohols including: sorbitol, xylitol, ribitol, mannitol, galactitol, fucitol, iditol, inositol, volemitol, isomalt, maltitol, lactitol, polyglycitol; celluloses such as carboxymethylcellulose, ethylcellulose, hydroxyethylcellulose, hydroxymethylethylcellulose, hydroxyethylpropylcellulose, methylhydroxyethylcellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based formulations containing organic and inorganic ingredients such as molasses. Suitable protein inert fillers illustratively include soy extract, zein, protamine, collagen, and casein. Inert fillers operative herein also include synthetic organic polymers capable of promoting or producing cohesion of particle components and such inert fillers illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex.

In some embodiments, a formulation contains between about 1 and about 90 weight % inert filler, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, or between about 60 and about 90 weight %.

In some embodiments, a formulation may include a solvent or a mixture of solvents that can be used to assist in controlling the solubility of the active ingredient itself, the nanoparticles of polymer-associated active ingredients, or other components of the formulation. For example, the solvent can be chosen from water, alcohols, alkenes, alkanes, alkynes, phenols, hydrocarbons, chlorinated hydrocarbons, ketones, water, ethers, and mixtures thereof. In some embodiments, the formulation contains a solvent or a mixture of solvents that makes up about 0.1 to about 90 weight % of the formulation. In some embodiments, a formulation contains between about 0.1 and about 90 weight % solvent, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, or between about 60 and about 90 weight %, between about 0.1 and about 10 weight %, between about 0.1 and about 5 weight %, between about 0.1 and about 3 weight %, between about 0.1 and about 1 weight %, between about 0.5 and about 20 weight %, between about 0.5 and about 10 weight %, between about 0.5 and about 5 weight %, between about 0.5 and about 3 weight %, between about 0.5 and about 1 weight %, between about 1 and about 20 weight %, between about 1 and about 10 weight %, between about 1 and about 5 weight %, between about 1 and about 3 weight %, between about 5 and about 20 weight %, between about 5 and about 10 weight %, and between about 10 and about 20 weight %.

In some embodiments, a formulation may include a surfactant. When included in formulations, surfactants can function as wetting agents, dispersants, emulsifying agents, solublizing agents and bioenhancing agents. Without limitation, particular surfactants may be anionic surfactants, cationic surfactants, nonionic surfactants, amphoteric surfactants, silicone surfactants (e.g., Silwet L-77), and fluorosurfactants. Exemplary anionic surfactants include alkylbenzene sulfonates, alkyl sulfonates and ethoxylates, sulfosuccinates, phosphate esters, taurates, alkylnaphthalene sulfonates and polymers lignosulfonates. Exemplary nonionic surfactants include alkylphenol ethoxylates, aliphatic alcohol ethoxylates, aliphatic alkylamine ethoxylates, amine alkoxylates, sorbitan esters and their ethoxylates, castor oil ethoxylates, ethylene oxide/propylene oxide copolymers and polymeric surfactants. In some embodiments, surfactants can make up between about 1 and about 20 weight % of the formulation, e.g., between about 1 and about 15 weight %, between about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %. In some embodiments, a surfactant (e.g., a non-ionic surfactant) may be added to a formulation by the end user, e.g., in a spray tank. Indeed, when a formulation is added to the spray tank it becomes diluted and, in some embodiments, it may be advantageous to add additional surfactant in order to maintain the nanoparticles in dispersed form.

In some embodiments, a formulation may include an anti-settling agent or thickener that can help provide stability to a liquid formulation or modify the rheology of the formulation. Examples of anti-settling agents or thickeners include, but are not limited to, guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd resins such as Latron B-1956 from Rohm & Haas Co., plant oil based materials (cocodithalymide) with emulsifiers; polymeric terpenes; microcrystalline cellulose; methacrylates; poly(vinylpyrrolidone), syrups, and polyethylene oxide and fumed silica (e.g. Aerosil 380). In some embodiments, anti-settling agents or thickeners can make up between about 0.05 and about 10 weight % of the formulation, e.g., between about 0.05 to about 5 weight %, between about 0.05 to about 3 weight %, between about 0.05 to about 1 weight %, between about 0.05 to about 0.5 weight %, between about 0.05 to about 0.1 weight %, between about 0.1 to about 5 weight %, between about 0.1 to about 3 weight %, between about 0.1 to about 1 weight %, between about 0.1 to about 0.5 weight %, between about 0.5 to about 5 weight %, between about 0.5 to about 3 weight %, between about 0.5 to about 1 weight %, between about 1 to about 10 weight %, between about 1 to about 5 weight %, or between about 1 to about 3 weight %. In some embodiments, it is explicitly contemplated that a formulation of the present disclosure does not include a compound whose primary function is to act as an anti-settling or thickener. In some embodiments, compounds included in a formulation may have some anti-settling or thickening functionality, in addition to other, primary functionality, so anti-settling or thickening functionality is not a necessary condition for exclusion, however, formulation agents used primarily or exclusively as anti-settling agents or thickeners may be expressly omitted from the formulations.

In some embodiments, a formulation may include one or more preservatives that prevent microbial or fungal degradation of the product during storage. Examples of preservatives include but are not limited to, tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof. In some embodiments, preservatives can make up about 0.01 to about 0.2 weight % of the formulation, e.g., between about 0.01 and about 0.1 weight %, between about 0.01 and about 0.05 weight %, between about 0.01 and about 0.02 weight %, between about 0.02 and about 0.2 weight %, between about 0.02 and about 0.1 weight %, between about 0.02 and about 0.05 weight %, between about 0.05 and about 0.2 weight %, between about 0.05 and about 0.1 weight %, or between about 0.1 and about 0.2 weight %.

In some embodiments, a formulation may include anti-freezing agents, anti-foaming agents, and/or anti-caking agents that help stabilize the formulation against freezing during storage, foaming during use, or caking during storage. Examples of anti-freezing agents include, but are not limited to, ethylene glycol, propylene glycol, and urea. In certain embodiment a formulation may include between about 0.5 and about 10 weight % anti-freezing agents, e.g., between about 0.5 and about 5 weight %, between about 0.5 and about 3 weight %, between about 0.5 and about 2 weight %, between about 0.5 and about 1 weight %, between about 1 and about 10 weight %, between about 1 and about 5 weight %, between about 1 and about 3 weight %, between about 1 and about 2 weight %, between about 2 and about 10 weight %, between about 3 and about 10 weight %, or between about 5 and about 10 weight %.

Examples of anti-foaming agents include, but are not limited to, silicone based anti-foaming agents (aqueous emulsions of dimethyl polysiloxane FG-10 from Dow® Corning, Trans 10A from Trans-Chemo, Inc.), and non-silicone based anti-foaming agents such as octanol, nonanol, and silica. In some embodiments a formulation may include between about 0.05 and about 5 weight % of anti-foaming agents, e.g., between about 0.05 and about 0.5 weight %, between about 0.05 and about 1 weight %, between about 0.05 and about 0.2 weight %, between about 0.1 and about 0.2 weight %, between about 0.1 and about 0.5 weight %, between about 0.1 and about 1 weight %, or between about 0.2 and about 1 weight %.

Examples of an anti-caking agents include sodium or ammonium phosphates, sodium carbonate or bicarbonate, sodium acetate, sodium metasilicate, magnesium or zinc sulfates, magnesium hydroxide (all optionally as hydrates), sodium alkylsulfosuccinates, silicious compounds, magnesium compounds, C10-C22 fatty acid polyvalent metal salt compounds, and the like. Illustrative of anti-caking ingredients are attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids such as palmitic acid, stearic acid and oleic acid. Anti-caking agents also include refined kaolin clay, amorphous precipitated silica dioxide, such as HI SIL 233 available from PPG Industries, refined clay, such as HUBERSIL available from Huber Chemical Company, or fumed silica (e.g., Aerosil 380). In some embodiments, a formulation may include between about 0.05 and about 10 weight % anti-caking agents, e.g., between about 0.05 and about 5 weight %, between about 0.05 and about 3 weight %, between about 0.05 and about 2 weight %, between about 0.05 and about 1 weight %, between about 0.05 and about 0.5 weight %, between about 0.05 and about 0.1 weight %, between about 0.1 and about 5 weight %, between about 0.1 and about 3 weight %, between about 0.1 and about 2 weight %, between about 0.1 and about 1 weight %, between about 0.1 and about 0.5 weight %, between about 0.5 and about 5 weight %, between about 0.5 and about 3 weight %, between about 0.5 and about 2 weight %, between about 0.5 and about 1 weight %, between about 1 to 3 weight %, between about 1 to 10 weight %, between about or 1 and about 5 weight %.

In some embodiments, a formulation may include a UV-blocking compound that can help protect the active ingredient from degradation due to UV irradiation. Examples of UV-blocking compounds include ingredients commonly found in sunscreens such as benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof, UV-absorbing metal oxides such as titanium dioxide, zinc oxide, and cerium oxide, and nickel organic compounds such as nickel bis (octylphenol) sulfide, etc. Additional examples of each of these classes of UV-blockers may be found in Kirk-Othmer, Encyclopedia of Chemical Technology. In some embodiments, a formulation may include between about 0.01 and about 2 weight % UV-blockers, e.g., between about 0.01 and about 1 weight %, between about 0.01 and about 0.5 weight %, between about 0.01 and about 0.2 weight %, between about 0.01 and about 0.1 weight %, between about 0.01 and about 0.05 weight %, between about 0.05 weight % and about 1 weight %, between about 0.05 and about 0.5 weight %, between about 0.05 and about 0.2 weight %, between about 0.05 and about 0.1 weight %, between about 0.1 and about 1 weight %, between about 0.1 and about 0.5 weight %, between about 0.1 and about 0.2 weight %, between about 0.2 and about 1 weight %, between about 0.2 and about 0.5 weight %, or between about 0.5 and about 1 weight %. In some embodiments, it is explicitly contemplated that a formulation of the present disclosure does not include a compound whose primary function is to act as a UV-blocker. In some embodiments, compounds included in a formulation may have some UV-blocking functionality, in addition to other, primary functionality, so UV-blocking is not a necessary condition for exclusion, however, formulation agents used primarily or exclusively as UV-blockers may be expressly omitted from the formulations.

In some embodiments, a formulation may include a disintegrant that can help a solid formulation break apart when added to water. Examples of suitable disintegrants include cross-linked polyvinyl pyrrolidone, modified cellulose gum, pregelatinized starch, cornstarch, modified corn starch (e.g., STARCH 1500) and sodium carboxymethyl starch (e.g., EXPLOTAB or PRIMOJEL), microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides (e.g., EMCOSOY), alkylcelullose, hydroxyalkylcellulose, alginates (e.g., SATIALGINE), dextrans and poly(alkylene oxide) and an effervescent couple (citric or ascorbic acid plus bicarbonate), lactose, anhydrous dibasic calcium phosphate, dibasic calcium phosphate, magnesium aluminometasilicate, synthesized hydrotalcite, silicic anhydride and synthesized aluminum silicate. In some embodiments disintegrants can make up between about 1 and about 20 weight % of the formulation, e.g., between about 1 and about 15 weight %, between about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %.

As noted above, in some embodiments, a formulation may include fumed silica (e.g. Aerosil 380). While listed as a thickening and anti-caking agent above, it is though that the fumed silica also has dispersant and wetting agent properties in the formulations of the present disclosure. It is surprising that, in some embodiments, HSLS formulations that incorporate fumed silica have enhanced dispersibility and wettability properties, as silica is not a traditional component of current suspension concentrate formulations.

For example, fumed silica is traditionally used as an anti-settling agent and anti-caking agent, however, if our formulations this component appears to demonstrate dispersant and wetting agent properties as well.

Formulations

As described above, the nanoparticles of polymer-associated active ingredient can be formulated into different types of formulations for different applications. For example, the types of formulations can include wettable granules, wettable powders, and high solid liquid suspensions. Furthermore, as discussed above, formulation agents can include, but are not limited to dispersants, wetting agents, surfactants, anti-settling agents or thickeners, preservatives, anti-freezing agents, anti-foaming agents, anti-caking agents, inert fillers, and UV-blockers.

In some embodiments, a dispersion of polymer nanoparticles and active ingredient in a common solvent is dried (e.g., spray dried) to form a solid containing nanoparticles (optionally in aggregate form) of polymer-associated active ingredients. The spray dried solid can then be used as is or incorporated into a formulation containing other formulating agents to make a wettable granule (WG), wettable powder (WP), or a high solids liquid suspension (HSLS).

In some embodiments, active ingredient is milled in the presence of pre-formed polymer nanoparticles to form a solid containing nanoparticles (optionally in aggregate form) of polymer-associated active ingredients. The solid can then be used as is or incorporated into a formulation containing other formulating agents to make a wettable granule (WG), wettable powder (WP), or a high solids liquid suspension (HSLS). In some embodiments, the milling step may be performed in the presence of one or more formulating agents. In some embodiments, the milling step is performed in the presence of fumed silica. In some embodiments, the milling step may be performed in the presence of an aqueous phase.

Wettable Granules (WG)

In some embodiments, the dried solid can be made into a formulation that is a wettable granule (WG) by adding other formulating agents and by extruding the formulation to form granules. In some embodiments, a WG formulation may be made by mixing together a dried (e.g., spray-dried, freeze dried, etc.) or milled solid comprising nanoparticles of polymer-associated active ingredient (or aggregates thereof), a wetting agent (e.g., a surfactant such as sodium dodecylbenzene sulfonate) and/or a dispersant (e.g., a lignosulfonate such as Reax 88B, etc.) and an inert filler (e.g., lactose). In some embodiments a WG can be made using a wetting agent (e.g., a surfactant such as sodium dodecylbenzene sulfonate) and a dispersant (e.g., a lignosulfonate such as Reax 88B, etc.).

In some exemplary embodiments, the components of the WG formulation are all mixed in a vessel, moistened with about 30 to about 50% equivalent mass of water, and the resulting semi-solid is extruded to make granules. In some embodiments, the formulation of the final WG can be (by weight): 0-5% dispersant, 0-5% wetting agent, 5-80% nanoparticles of polymer-associated active ingredient (optionally in aggregate form), and inert filler to 100%. In some embodiments, the formulation of the final WG can be (by weight): 0.5-5% dispersant, 0.5%-5% wetting agent, 5-80% nanoparticles of polymer-associated active ingredient (optionally in aggregate form), and inert filler to 100%. As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g. wettable granules.

In some embodiments, a WG formulation comprising nanoparticles of polymer-associated active ingredients (optionally in aggregate form) may be made by using a dispersion of polymer nanoparticles and active ingredient in a common solvent, preferably methanol. In some embodiments, a WG formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and an inert filler (e.g., lactose), drying (freeze drying, spray drying, etc.) the resulting mixture to from a solid and then granulating the solid to obtain a WG formulation comprising nanoparticles of polymer-associated active ingredients (optionally in aggregate form). In some embodiments a WG can be made using a wetting agent (e.g., a surfactant such as sodium dodecylbenzene sulfonate) and a dispersant (e.g., a lignosulfonate such as Reax 88B, etc.). As described above in the Formulating Agents section, a wide variety of formulating agent(s) and various concentrations of wetting agents, dispersants, fillers and other formulating agents can be used to prepare exemplary formulations, e.g. wettable granules.

In addition to the various polymer nanoparticles described above, exemplary polymer nanoparticles are made from a co-polymer of methyl methacrylic acid and ethyl acrylate at a 90:10 mass ratio. In some embodiments, the polymer nanoparticles are made from a co-polymer of methyl methacrylic acid and styrene at a 90:10 mass ratio. In some embodiments, the polymer nanoparticles are made from a co-polymer of methyl methacrylic acid and butylmethacrylate at a 75:25 mass ratio. In some embodiments, the polymer nanoparticles are dispersed in a common solvent, in some cases at a concentration of 20 mg/mL or higher. As described above in the Nanoparticles of polymer-associated active ingredient section, many ratios of co-polymer constituents can be used.

In some exemplary embodiments, the active ingredient is selected from lambda cyhalothrin, cypermethrin, deltamethrin, and bifenthrin. In some embodiments, the ratio of active ingredient to polymer nanoparticle is 1:1, 2:1, 3:1, 4:1 or 5:1, a range between these values or another range as listed above. As described above in the Nanoparticles of polymer-associated active ingredient section, many ratios of pyrethroid to polymer can be used.

In some embodiments, the dispersion of polymer nanoparticles and active ingredient in a common solvent is slowly added to a vessel containing a second solvent, preferably water. In some embodiments, the second solvent is at least 20 times larger in volume than the common solvent containing the polymer nanoparticles and active ingredient. In some embodiments, the second solvent contains a dispersant, preferably but not limited to a lignosulfonate such as Reax 88B and/or a wetting agent, preferably but not limited to a surfactant such as sodium dodecylbenzene sulfonate and an inert filler, preferably but not limited to lactose.

In some embodiments, after the dispersion in a common solvent is mixed with the second solvent the solvents are removed by drying. In some embodiments, the solvents are removed by freeze drying. In some embodiments, the solvents are removed by spray drying. The resulting solid formulation is then moistened with about 30 to about 50% equivalent mass of water and is then extruded to form granules. In some exemplary embodiments, the granules are formed by hypodermic syringe extrusion. In some embodiments, the granules are formed through extrusion granulation, pan granulation, fluid bed granulation, spray drying granulation, or high shear granulation.

In some embodiments, the granules disperse in solution in 30 seconds or less. In some case the WG formulation has low friability. In some embodiments, the WG formulation has low dustiness. In some embodiments, when the WG formulation is dispersed in water, the dispersion results in particles with an average size within about 100 to about 200 nm, or in some cases, within about 100 to about 150 nm. In some embodiments, a dispersion of the WG formulation in water creates minimal foam. In some embodiments, the WG formulation containing lambda cyhalothrin has minimal skin irritating effects. In some embodiments, the WG formulation is stable after 1-2 months of continuous temperature cycling between −5° C. and 45° C.

In some embodiments, the current disclosure provides methods of producing WGs comprising low melting-point actives via extrusion of the granules. In some embodiments, the active has a melting point of less than about 100° C., less than about 90° C., less than about 80° C., less than about 70° C., less than about 60° C., less than about 50° C. or less than about 40° C. It is surprising that wettable granules of low-melting point actives can be prepared via extrusion of the granules. As discussed above, the heat produced during extrusion generally leads to complications, such as separation of the active ingredient. In some embodiments, the active ingredient of the wettable granules of the current disclosure is bifenthrin, cyhalothrin (including all isomeric compositions and ratios), gamma-cyhalothrin, lambda-cyhalothrin, cypermethrin (including all isomeric compositions and ratios), alpha-cypermethrin, beta-cypermethrin, theta-cypermethrin, zeta-cypermethrin, deltamethrin, esfenvalerate, fenvalerate permethrin, and acrinathrin or resmethrin.

Wettable Powder (WP)

In some embodiments, the dried solid can be made into a formulation that is a wettable powder (WP). In some embodiments, a WP formulation comprising nanoparticles of polymer-associated active ingredients (optionally in aggregate form) can be made from a dried (e.g., spray dried, freeze dried, etc.) dispersion of polymer nanoparticles and active ingredient. In some embodiments, a WP formulation comprising nanoparticles of polymer-associated active ingredients (optionally in aggregate form) can be made from a milled solid comprising polymer nanoparticles of active ingredient. In some embodiments, a WP is made by mixing the dried or milled solid with a dispersant and a wetting agent. In some embodiments, a WP is made by mixing the dried solid with a dispersant and a wetting agent. In some embodiments, the formulation of the final WP can be (by weight): up to about 98% nanoparticles of polymer-associated active ingredients (including both the active ingredient and the polymer, optionally in aggregate form). In some embodiments, the WP formulation includes (by weight): 0-5% dispersant, 0-5% wetting agent, 5-98% nanoparticles of polymer-associated active ingredients (optionally in aggregate form), and inert filler to 100%. In some embodiments, the formulation of the final WP can be (by weight): 0.5-5% dispersant, 0.5%-5% wetting agent, 5-98% nanoparticles of polymer-associated active ingredients (optionally in aggregate form). As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g. wettable powders.

In some embodiments, the formulation of the final WP can be (by weight): 0.5-5% dispersant, 0.5%-5% wetting agent, 0.1-10% thickener (e.g., fumed silica which, as noted above may serve multiple functions, and/or xanthan gum), 5-98% nanoparticles of polymer-associated active ingredients (optionally in aggregate form). As described above in the Formulating Agents section, a wide variety of formulating agent(s) and various concentrations of wetting agents, dispersants, fillers and other formulating agents can be used to prepare exemplary formulations, e.g. wettable powders.

In some embodiments, a WP formulation comprising nanoparticles of polymer-associated active ingredients (optionally in aggregate form) may be made from a dispersion of polymer nanoparticles and active ingredient in a common solvent, preferably methanol. In some embodiments, a WP formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and optionally an inert filler (e.g., lactose), and then drying (e.g., freeze drying, spray drying, etc.) the resulting mixture to from a solid powder. In some embodiments a WP can be made using a wetting agent (e.g., a surfactant such as sodium dodecylbenzene sulfonate) and a dispersant (e.g., a lignosulfonate such as Reax 88B, etc.).

In some exemplary embodiments, described in more detail below, the polymer nanoparticles are made from a co-polymer of methacrylic acid and ethyl acrylate at about a 90:10 mass ratio. In some embodiments, the polymer nanoparticles are dispersed in a common solvent, preferably at a concentration of 20 mg/mL. In some embodiments, the polymer nanoparticles are made from a co-polymer of methacrylic acid and styrene at about at a mass ratio of 75:25. In some embodiments, the polymer nanoparticles are made from a co-polymer of acrylic acid and styrene at about a 75:25 mass ratio. In some embodiments, the polymer nanoparticles are made from a co-polymer of acrylic acid and styrene at about a 90:10 mass ratio. As described above in the Nanoparticles of polymer-associated active ingredient section, many ratios of co-polymer constituents can be used.

In some exemplary embodiments, the active ingredient is cypermethrin. In some exemplary embodiments, the active ingredient is deltamethrin. In some exemplary embodiments, the active ingredient is bifenthrin. In some exemplary embodiments, the ratio of active ingredient to polymer nanoparticle is 1:1, 2:1, 3:1, 4:1 or 5:1, a range between these values or another range as listed above. As described above in the Nanoparticles of polymer-associated active ingredient section, many ratios of pyrethroid to polymer can be used.

In some embodiments, the dispersion of polymer nanoparticles and active ingredient is then slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a WP can be made using a wetting agent (e.g., a surfactant such as sodium dodecylbenzene sulfonate) and a dispersant (e.g., a lignosulfonate such as Reax 88B, etc.).

In some embodiments, after the dispersion of polymer nanoparticles and active ingredient in a common solvent is mixed with a second solvent containing dispersant and/or wetting agent, the final mixture is dried (e.g., freeze dried) to obtain a solid powdered formulation containing nanoparticles of polymer-associated active ingredients (optionally in aggregate form).

High Solids Liquid Suspension (HSLS)

One type of formulation that can be utilized according to the disclosure is a high solids liquid suspension. As described, such a formulation is generally characterized in that it is a liquid formulation that contains at least nanoparticles of polymer nanoparticles associated with active ingredient (includes potentially aggregates of the same).

In some embodiments, the formulation of the HSLS can be (by weight): between about 5 and about 80% nanoparticles of polymer-associated active ingredients (including both polymer and active ingredient, optionally in aggregate form), 0.5 and about 5% wetting agent and/or dispersant, between about 1 and about 10% anti-freezing agent, between about 0.2 and about 10% anti-settling agent or thickener, between about 0.1 and about 10% anti-foaming agent, between about 0.01 and about 0.1% preservative and water up to 100% As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g., a HSLS.

In some exemplary embodiments, the polymer nanoparticles are made from a co-polymer of methyl methacrylic acid and ethyl acrylate at a 90:10 mass ratio. In some embodiments, the polymer nanoparticles are dispersed in the common solvent, preferably at a concentration of 20 mg/mL. In some embodiments, the active ingredient is either lambda cyhalothrin, cypermethrin, or bifenthrin and is mixed into the nanoparticle dispersion at a concentration of 20 mg/mL. As described above in the Nanoparticles of polymer-associated active ingredient section, many ratios of co-polymer constituents can be used. As described above in the Nanoparticles of polymer-associated active ingredient section, many ratios of co-polymer constituents can be used.

In some exemplary embodiments, the dispersion of polymer nanoparticles and active ingredient in a common solvent is slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a HSLS can be made using a wetting agent (e.g., a surfactant such as sodium dodecylbenzene sulfonate) and a dispersant (e.g., a lignosulfonate such as Reax 88B, etc.).

In some embodiments the HSLS formulations of current disclosure have an active ingredient content of about 5 to about 40% by weight, e.g., about 5-about 40%, about 5-about 35%, about 5-about 30%, about 5-about 25%, about 5-about 20%, about 5-about 15%, about 5-about 10%, about 10-about 40%, about 10-about 35%, about 10-about 30%, about 10-about 25%, about 10-about 20%, about 10-about 15%, about 15-about 40%, about 15-about 35%, about 15-about 30%, about 15-about 25%, about 15-about 20%, about 20-about 40%, about 20-about 35%, about 20-about 30%, about 20-about 25%, about 25-about 40%, about 25-about 35%, about 25-about 30%, about 30-about 40% or about 35-about 40%. As described above in the Nanoparticles of polymer-associated active ingredient section, many ratios of pyrethroid to polymer can be used.

In some embodiments the HSLS formulations of current disclosure have an active ingredient content of about 5%, about 10%, about 15%, about 20%, about 25%, about 30%, about 35% or about 40% by weight.

Methods of Making HSLS—Generally

In some embodiments, a HSLS comprising nanoparticles of polymer-associated active ingredient (optionally in aggregate form) can be made from a dispersion of polymer nanoparticles and active ingredient in a common solvent or from a dried form of the dispersion (e.g., spray dried). In some embodiments, a HSLS formulation comprising nanoparticles of polymer-associated active ingredients (optionally in aggregate form) can be made from a milled solid comprising polymer nanoparticles of active ingredient.

Methods of Making HSLS—Milling Methods

In some embodiments, a HSLS formulation comprising nanoparticles of polymer-associated active ingredients (optionally in aggregate form) can be prepared via milling. Several exemplary methods and the resulting HSLS formulations are described below and in the Examples. In some embodiments, a solid formulation of nanoparticles of polymer-associate active ingredient (optionally in aggregate form), prepared as described in this disclosure (e.g., via milling, spray drying etc.) may be further milled in the presence of one or more formulating agents and water. In some embodiments a HSLS can be made by milling a solid formulation nanoparticles of polymer-associated active ingredients in the presence water and one more of an anti-freezing agent, (optionally more than one of) a wetter and/or dispersant, an antifoaming agent, a preservative, and a thickening agent. Further, in some embodiments, the active ingredient and polymer nanoparticles are milled, either just these two components of the formulation or with one or more additional formulating agents, to produce comprising nanoparticles of polymer-associated active ingredients, which may then be further milled according to the processes described below.

In some embodiments, the milling process is performed in separate phases (i.e., periods of time), with the optional addition of one or more formulating agent between each milling phase. One of ordinary skill in the art can adjust the length of each phase as is appropriate for a particular instance. In some embodiments, the contents of the milling vessel are cooled between one or more of milling phases (e.g., via placement of the milling jar in an ice bath). One of ordinary skill in the art can adjust the length of cooling period as is appropriate for a particular instance.

In some embodiments a HSLS can be made by first milling a solid formulation of nanoparticles of polymer-associated active ingredients in the presence of one or more of water, a wetter and/or dispersant, an anti-freezing agent, an antifoaming agent, a preservative, a thickener and, and/or an anti-caking agent. In some embodiments, after milling these components together, a thickener is added to the formulation. In some embodiments, after addition of the thickening agent, the milling process is continued.

In some embodiments, a HSLS formulation comprising nanoparticles of polymer-associated active ingredients (optionally in aggregate form) can be prepared by milling pre-formed polymer nanoparticles and active ingredient in a milling vessel (e.g. milling jar). In some embodiments, after the pre-formed nanoparticles and active ingredient are milled, water, an anti-freezing agent, (optionally more than one of) a wetter and/or dispersant, an antifoaming agent, a preservative, (optionally more than one of) a thickener, and an anti-caking agent are added to the milling vessel and the milling process is continued. In some embodiments, after milling these components together, a thickener is added to the formulation. In some embodiments, after addition of the thickener, the milling process is continued.

In some embodiments, a HSLS can be made by first milling a solid formulation of nanoparticles of polymer-associated active ingredients in the presence of (optionally more than one of) a wetter and/or dispersant in one milling vessel for a certain amount of time (e.g., about 30 minutes-about 1 day), then this mixture is transferred to another milling vessel containing water and optionally one or more of an anti-freezing agent, additional wetter and/or dispersant, an anti-freezing agent, an antifoaming agent, a preservative, a thickening agent, and milling the components together. As described above in the Formulating Agents section, a wide variety of additional formulating agent(s) and various concentrations of wetting agents, dispersants, fillers and other formulating agents can be used in preparation of exemplary formulations.

In some embodiments, a HSLS formulation comprising nanoparticles of polymer-associated active ingredients (optionally in aggregate form) can be prepared via milling pre-formed polymer nanoparticles and active ingredient in the presence of one or more formulating agents and water. In some embodiments, a HSLS can be made by milling preformed polymer nanoparticles and active ingredient in the presence of water and optionally one more of an anti-freezing agent, additional wetter and/or dispersant, an anti-freezing agent, an antifoaming agent, a preservative, and a thickening agent. Again, as described above in the Formulating Agents section, a wide variety of additional formulating agent(s) and various concentrations of wetting agents, dispersants, fillers and other formulating agents can be used in preparation of exemplary formulations.

And as in the embodiment described above in which nanoparticles of polymer-associated active ingredients are milled in a two milling vessel procedure, such a procedure can be used in preparing a HSLS from pre-formed polymer nanoparticles. In some embodiments such an HSLS can be made by first milling a solid formulation nanoparticles of polymer-associated active ingredients in the presence of (optionally more than one of) a wetter and/or dispersant in one milling vessel for a certain amount of time (e.g., about 30 minutes-about 1 day), transferring the milled components to another milling vessel containing water and optionally one or more of an anti-freezing agent, additional wetter and/or dispersant, an anti-freezing agent, an antifoaming agent, a preservative and a thickening agent.

Milling methods to produce HSLS formulations as described above may include any of those referred to in any other portion of the specification including the Examples below. Any type of mill noted in any portion of the specification may also be used to prepare HSLS formulations via milling.

Methods of Making HSLS—Mixing & Drying Methods

In some embodiments, a HSLS formulation is prepared without milling, but instead by mixing the components of the formulation. These methods may also include drying the formulations to increase the solids content of the formulation so that it is suitable as a HSLS. All of these methods are described in more detail below and exemplary methods are shown in the Examples.

In some embodiments, a HSLS formulation comprising nanoparticles of polymer-associated active ingredients (optionally in aggregate form) can be made from the dispersion of polymer nanoparticles and active ingredient in a common solvent (e.g., methanol). In some embodiments, the dispersion is added to an aqueous solution containing a wetting agent and a dispersant, an anti-freezing agent (and optionally an anti-settling agent or thickener and a preservative). The mixture is then concentrated by removing solvent, e.g., by drying, until the desired high solids formulation is attained.

In some embodiments, after the dispersion of polymer nanoparticles and active ingredient in a common solvent is mixed with a second solvent containing a wetting agent and/or dispersant and an anti-freezing agent (optionally with an anti-settling agent or thickener and a preservative), the final mixture is concentrated by removing most of the common solvent and second solvent until a final formulation with a target solids content (e.g., at least 60% solids) is obtained. In some embodiments, the method used to concentrate the solution is vacuum evaporation. In some embodiments, a second solvent containing a wetting agent and/or dispersant and an anti-freezing agent (optionally with an anti-Page settling agent or thickener and a preservative) are added after the mixture has already been concentrated.

In some embodiments, a HSLS is made by mixing the dried dispersion (e.g., spray dried) with a wetting agent, preferably a surfactant such as sodium dodecylbenzene sulfonate, a solvent, preferably but not limited to water, and/or a dispersant, preferably, but not limited to a lignosulfonate such as Reax 88B, and an anti-freezing agent, preferably but not limited to ethylene glycol, in a high sheer mixer until a stable HSLS is obtained. In some embodiments a wetting agent, preferably a surfactant such as sodium dodecylbenzene sulfonate, a solvent, preferably but not limited to water, and a dispersant, preferably, but not limited to a lignosulfonate such as Reax 88B are included. In some embodiments, a preservative, preferably propionic acid and an anti-settling agent or thickener, preferably but not limited to fumed silica and/or a water dispersible agent like xanthan gum are also included.

In some embodiments, a HSLS is made by reconstituting the dried dispersion (e.g., freeze dried) of nanoparticles of polymer-associated active ingredients in water to obtain a formulation with a target solids content (e.g., at least 60% solids) is obtained and then adding an anti-freezing agent (and optionally a thickening agent and a preservative) to the final mixture. In some embodiments, a HSLS is made by reconstituting the milled (as described above) solid of nanoparticles of polymer-associated active ingredients in water to obtain a formulation with a target solids content (e.g., at least 60% solids) is obtained and then adding an anti-freezing agent (and optionally at least one thickening agent (e.g., fumed silica and/or xanthan gum), an antifoaming agent and a preservative) to the final mixture. In some embodiments, the HSLS is made by homogenizing all the components together.

In some embodiments, the dispersion of polymer nanoparticles and active ingredient in a common solvent is added to a second solvent to form a solution of nanoparticles of polymer-associated active ingredients (optionally in aggregate form). The second solvent is typically miscible with the common solvent and is usually water, but in some embodiments, the second solvent can also be a mixture of water with a third solvent, usually an alcohol, preferably methanol or ethanol. In some embodiments, the second solvent or mixture of solvents is only partially miscible with the common solvent. In some embodiments, the second solvent or mixture of solvents is not miscible with the common solvent.

Use of Low Melting Point Actives in HSLS Formulations

In some embodiments, the current disclosure provides methods of producing HSLS formulations comprising low melting-point actives. In some embodiments, the active has a melting point of less than about 100° C., less than about 90° C., less than about 80° C., less than about 70° C., less than about 60° C., less than about 50° C. or less than about 40° C. The preparation of traditional suspension concentrates of low melting-point actives is a non-trivial process. As discussed previously, typical suspension concentrate formulation involves milling the active ingredient to generate particles of about 1 to about 10 microns followed by dispersion of these particles in an aqueous phase in presence of surfactants. The use of standard milling equipment melts low-melting point actives, complicating or precluding the size reduction process. It is thus useful that HSLS formulations of low-melting point actives may be prepared according to the current disclosure. It is also surprising that, in some embodiments, HSLS formulations can be prepared according to the present disclosure via milling of the active ingredient in the presence of pre-formed polymer nanoparticles. In some embodiments, the active ingredient of HSLS formulations of the current disclosure is bifenthrin, cyhalothrin (including all isomeric compositions and ratios), gamma-cyhalothrin, lambda-cyhalothrin, cypermethrin (including all isomeric compositions and ratios), alpha-cypermethrin, beta-cypermethrin, theta-cypermethrin, zeta-cypermethrin, deltamethrin, esfenvalerate, fenvalerate permethrin, acrinathrin, and resmethrin.

Efficacy and Application

General Application & Efficacy

The formulations of the current disclosure, described in detail above, are applicable to a wide variety of uses (e.g., application to specific plants, specific pets, in combination with other agro-chemicals) and demonstrate a number of surprising properties. For instance, among other functions, some of the formulations disclosed herein show remarkable stability in solution with high ionic strength, some formulations demonstrate a surprising ability to translocate within a plant, leading to systemic effects and higher residual activity. These particular feature are generally in comparison to commercially available formulations of the same active compounds. Thus, due to the surprising functionalities of the disclosed formulations, lower doses of active ingredient are required as compared to the current state of the art. The sections below describe some basis application principles applicable to the formulations of this disclosure, describe the surprising results obtained and detail some specific applications.

In the following discussion, inoculation of a target organism with a formulation of the present disclosure may, in some embodiments, refer to inoculation of a plant or insect with a dispersion (e.g. in water or an aqueous medium optionally comprising other components such as surfactants etc.) prepared from a formulation of the present disclosure as described in any portion of the specification. It is to be understood that the term formulation may also encompass dispersions for application as described. As used anywhere in the specification, inoculation of a target organism with a formulation of the current disclosure may, in some embodiments, refer to inoculation of a plant with a dispersion (e.g., in water or an aqueous medium optionally further comprising other additives such as adjuvants, surfactants etc.) prepared from a formulation of the present disclosure as described above.

It should also be understood that methods that describe the use of pyrethroid formulations of the present disclosure e.g. "use of formulations of the present disclosure to inoculate a target organism or plant," "use of the formulations of the present disclosure to control pests" and the like, encompass the preparation and use of a dispersion of the active ingredient in a water or an aqueous medium (optionally comprising other components such as surfactants etc.) from formulations of the present disclosure, and use of the dispersion in the intended application (e.g. inoculation of a target or pest control application).

In some embodiments, a formulation comprising nanoparticles of polymer-associated active ingredients and other formulating agents is added to water (e.g., in a spray tank) to make a dispersion that is about 10 to about 2,000 ppm in active ingredient. In some embodiments, the dispersion is about 10 to about 1,000 ppm, about 10 to about 500 ppm, about 10 to about 300 ppm, about 10 to about 200 ppm, about 10 to about 100 ppm, about 10 to about 50 ppm, about 10 to about 20 ppm, about 20 to about 2,000 ppm, about 20 to about 1,000 ppm, about 20 to about 500 ppm, about 20 to about 300 ppm, about 20 to about 200 ppm, about 20 to about 100 ppm, about 20 to about 50 ppm, about 50 to about 2,000 ppm, about 50 to about 1,000 ppm, about 50 to about 500 ppm, about 50 to about 300 ppm, about 50 to about 200 ppm, about 50 to about 100 ppm, about 100 to about 2,000 ppm, about 100 to about 1,000 ppm, about 100 to about 500 ppm, about 100 to about 300 ppm, about 100 to about 200 ppm, about 200 to about 2,000 ppm, about 200 to about 1,000 ppm, about 200 to about 500 ppm, about 200 to about 300 ppm, about 300 to about 2,000 ppm, about 300 to about 1,000 ppm, about 300 to about 500 ppm, about 500 to about 2,000 ppm, about 500 to about 1,000 ppm, about 1000 to about 2,000 ppm.

In general, different pyrethroids are typically applied at different effective rates between 10-400 g/hectare depending on the efficacy of the pyrethroid (e.g., absolute potency of the active and retention at the site of activity), as well as conditions related to the crop being treated, leaf type, environmental conditions, the species infesting the crop, infestation levels, and other factors. Improvements in the formulation according to this disclosure, such as increased UV stability, physical retention at the site of action, residual activity, and systemic absorption can reduce the user rates. Some embodiments of the disclosure demonstrate improvements over typical commercial formulation and therefore suggest that lower rates of effective application could be used. In some embodiments, concentrations according to the disclosure may range from 0.1-400 g/hectare, preferably 0.1-200 g/hectare, more preferably 0.1-100 g/hectare, more preferably 0.1-10 g/hectare or more preferably 0.1-1 g/hectare. In some embodiments, rates according to the disclosure may range from 1 g-400 g/hectare, preferably 1-200 g/hectare, more preferably 1-100 g/hectare, or more preferably 1-10 g/hectare. In some embodiments, rates according to the disclosure may be any of the rates or ranges of rates noted in any other portion of the specification.

General Application & Comparison to Current Commercial Formulations

In some embodiments, the current disclosure provides formulations of pyrethroid compounds that result in decreased leaf damage, e.g., as compared to an emulsion concentrate (EC) formulation with the same active ingredient (e.g., MATADOR 120EC in the case of lambda cyhalothrin). In some embodiments, there is decreased leaf damage to leaves of a cole crop (e.g., cabbage) inoculated with a formulation containing nanoparticles of polymer-associated active ingredients via dipping or spraying. In some exemplary embodiments, there is decreased leaf damage to leaves of a cole crop (e.g., cabbage) inoculated with a formulation containing nanoparticles of polymer-associated active ingredients via dipping or spraying with pyrethroid concentration in the 0.1 to 0.5 parts per million range.

In some embodiments, the current disclosure provides formulations of pyrethroid compounds that are more stable to photolysis, e.g., as compared to neat pyrethroid alone or formulation that include a UV-blocker (e.g., MATADOR 120EC in the case of lambda cyhalothrin). In some exemplary embodiments, described in more details in the Examples below, thin films of the formulation of pyrethroid compounds cast on a substrate and exposed under a solar simulator for a set period of time (e.g., 4 hours) were far more resistant to photolysis (e.g., 28 times more resistant) as compared to the neat pyrethroid alone. In another exemplary embodiment, thin films of the formulation of pyrethroid compounds without UV-blocker cast on a substrate and exposed under a solar simulator for a set period of time (e.g., 4 hours) were more resistant to photolysis than a commercial formulation containing a UV-blocker.

Labels of commercially available pyrethroid products often provide ranges of active ingredient use rates to control pests in certain applications (e.g., control of a certain pest of a soybean). In some embodiments, the pyrethroid formulations of the current disclosure are used to control pests at an active ingredient use rate that is lower than the minimum use rate of a range of use rates listed on the label of a commercially available pyrethroid product. In some embodiments a pyrethroid formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

In some embodiments, a dispersion is produced according to the current disclosure to inoculate a plant with active ingredient at a use rate that is lower than a use rate listed on the label of a currently available pyrethroid product. In some embodiments, a dispersion is produced to inoculate a plant with active ingredient at a use rate that is less than about 75% of a use rate listed on the label of a currently available pyrethroid product of the same active ingredient. In some embodiments, a dispersion is produced to inoculate a plant with active ingredient at a use rate that is less than about 50% of a use rate listed on the label of a currently available pyrethroid product of the same active ingredient. In some embodiments, a dispersion is produced to inoculate a plant with active ingredient at a use rate that is less than about 40% of a use rate listed on the label of a currently available pyrethroid product of the same active ingredient. In some embodiments, a dispersion is produced to inoculate a plant with active ingredient at a use rate that is less than about 30% of a use rate listed on the label of a currently available pyrethroid product of the same active ingredient. In some embodiments, a dispersion is produced to inoculate a plant with active ingredient at a use rate that is less than about 25% of a use rate listed on the label of a currently available pyrethroid product of the same active ingredient. In some embodiments, a dispersion is produced to inoculate a plant with active ingredient at a use rate that is less than about 20% of a use rate listed on the label of a currently available pyrethroid product of the same active ingredient. In some embodiments, a dispersion is produced to inoculate a plant with active ingredient at a use rate that is less than about 10% of a use rate listed on the label of a currently available pyrethroid product of the same active ingredient.

Pesticide labels are readily accessible from manufacturers' websites, or via centralized internet databases such as Greenbook (http://www.greenbook.net/) or the Crop Data Management Systems website (www.cdms.net). In some embodiments, the formulations of the current disclosure may be used to control pests at a range of active ingredient dose rates whose high and low values are about 75%, about 60%, about 50%, about 40%, about 30%, about 20% or about 10% of the high and low dose rates of a range of dose rates listed on the label of a commercially available product of the same active ingredient. In some embodiments, the high and low dose rates of formulations of the current disclosure are both lower than the high and low dose rates of the commercial product by the same percentage.

In some embodiments, the formulations of the current disclosure may be used to control pests at an active ingredient use rate that is lower than the minimum rate of a range of rates listed on the label of a commercially available pyrethroid product of the same active ingredient. In some embodiments, the formulations of the current disclosure may be used to control pests at an active ingredient use rate that is less than about 75%, less than about 60%, less than about 50%, less than about 40%, less than about 30%, less than about 20% or less than about 10% of the minimum use rate of a range of rates listed on the label of a commercially available product.

In some embodiments, the formulations of the current disclosure may be used to control pests at an active ingredient use rate that corresponds to any value that falls within any disclosed range of values in any portion of the specification, including a value corresponding to the endpoints of the range. In some embodiments, the formulations of the current disclosure may be used to control pests at an active ingredient use rate that corresponds to a range of values that falls within any disclosed range of values in any portion of the specification, including a range of values whose highest or lowest values corresponds to the endpoints of a disclosed range.

In some embodiments, the plant (e.g., crop) on which pests can be controlled by formulations of the present disclosure may depend on, among other variables, the active ingredient, inclusion of other components into the formulation, and the particular application. Common commercial formulations frequently include labels and instructions describing the compatibility of other agricultural products, tank-mix instructions, labeled pests, instructions and restrictions for particular applications and uses, as well as other information. Such labels and instructions pertinent to the formulations of the current disclosure and to their application are also contemplated as part of the current disclosure. Labels are readily accessible from manufacturers' websites, or via centralized internet databases such as Greenbook (http://www.greenbook.net/) or the Crop Data Management Systems website (www.cdms.net).

Improved Efficacy of Formulations

As noted previously and described in the Examples, in some embodiments, the current disclosure provides formulations of pyrethroid compounds that have improved insect mortality. In some embodiments, there is increased mortality in lepidopteran species (e.g., cabbage looper) that have been exposed to leaves of a cole crop (e.g., cabbage) inoculated with a formulation containing nanoparticles of polymer-associated active ingredients via dipping or spraying. In some exemplary embodiments, described in more details in the Examples below, the increased mortality corresponds to a decrease in the LC50 of the formulation by between 1.25 times and 5 times, e.g., as compared to an emulsion concentrate (EC) formulation with the same active ingredient (e.g., MATADOR 120EC in the case of lambda cyhalothrin and Brigade® 2EC in the case of bifenthrin). In some embodiments, the increased mortality corresponds to a decrease in the LC50 of the formulation by between 1.5 times and 5 times. In some embodiments, the increased mortality corresponds to a decrease in the LC50 of the formulation by between 2.5 times and 5 times. In some embodiments, the increased mortality corresponds to a decrease in the LC50 of the formulation by between 3 times and 5 times. In some embodiments, the increased mortality corresponds to a decrease in the LC50 of the formulation by more than 5 times. In some embodiments, the increased mortality corresponds to a decrease in the LC50 of the formulation by between 2 times and 3 times.

In some embodiments, there is increased mortality in lepidopteran species (e.g., cabbage looper) that have been exposed to leaves of a cole crop (e.g., cabbage) inoculated with a formulation containing nanoparticles of polymer-associated active ingredients via dipping or spraying with pyrethroid concentrations as low as about 0.1 parts per million. In some embodiments, there is increased mortality in lepidopteran species (e.g., cabbage looper) that have been exposed to leaves of a cole crop (e.g., cabbage) inoculated with a formulation containing nanoparticles of polymer-associated active ingredients via dipping or spraying with pyrethroid concentrations in the range of about 0.1 to about 1.0 parts per million. In some embodiments, the pyrethroid of is lambda-cyhalothrin. In some embodiments, the pyrethroid of is bifenthrin.

Increased Residual & Systemic Activity & Rainfast Applications

In some embodiments, the current disclosure provides formulations of pyrethroid compounds that have increased residual activity and rainfastness, e.g., as compared to an emulsion concentrate (EC) formulation with the same active ingredient (e.g., MATADOR 120EC in the case of lambda cyhalothrin and TALSTAR in the case of Bifenthrin). As the examples below demonstrate, formulations of the current disclosure demonstrated increased activity when applied at the same rate as compared to commercial formulations (e.g., knock down rates, as well as residual and systemic activity).

The following summarize experiments detailed below in the Examples section. In some exemplary embodiments, broadcast application of a formulation of pyrethroid according to the current disclosure to a cole crop (cabbage) in the field at 18 g/hectare (36 g/hectare of formulated nanoparticle associated pyrethroid with a formulation 1 part active per 1 part polymer nanoparticles) showed increased residual activity towards lepidopteran species (cabbage looper) in lab bioassays. Additionally, broadcast application of the formulation of pyrethroid compound to a cole crop (cabbage) in the field at 18 g active/hectare showed increased knockdown rate. Further, broadcast application of the formulation of pyrethroid compound to a leafy green crop (lettuce) in the field at 18 g active/hectare showed increased systemic activity of the pyrethroid.

Additionally, the application of a formulation of Bifenthrin according to the current disclosure to a cole crop (cabbage) via a leaf dip assay showed superior rainfast properties compared to a commercial EC formulation. Though the specifics of a comparison test are described in an Example below, generally, the exemplary procedure is as follows: A 4 cm cut disk of a cole plant leaf (cabbage) was inoculated with a pyrethroid by dipping the disk into a solution containing either a commercial pyrethroid formulation or a pyrethroid formulation according to the current disclosure at a specific use rate (e.g. 1 ppm pyrethroid) along with 0.5 wt % non-ionic surfactant (Induce) for 5 seconds and was allowed to air dry for 2 hours. Rainfastness was evaluated by dipping inoculated leaf disks (as described below) into deionized water for 5 seconds, allowing the leaf to air dry for 2 hours. This is followed by the addition of four 2nd to 3rd instar cabbage looper larvae onto each disk. In some exemplary embodiments, the lepidopteran larvae mortality was assessed after 48 hours. In some exemplary embodiments, leaf disks that have been inoculated with formulations of pyrethroid according to the current disclosure show improved rainfast properties compared to leaves inoculated with commercial formulations. In some embodiments, the pyrethroid formulated according to the current disclosure is bifenthrin. In some embodiments, the formulation is in the form of a wettable powder.

Improved Translocation of Active

In some embodiments, the current disclosure provides formulations of pyrethroid compounds that have increased root uptake, e.g., as compared to an emulsion concentrate (EC) formulation with the same active ingredient (e.g., MATADOR 120EC in the case of lambda cyhalothrin). In some exemplary embodiments, there is increased uptake of the pyrethroid compound after the formulation has been inoculated (e.g., 48 hours after) to the root zone of a cole crop (e.g., cabbage).

In some embodiments, the current disclosure provides formulations of pyrethroid compounds that have increased leaf mobility or translocation, e.g., as compared to an emulsion concentrate (EC) formulation with the same active ingredient (e.g., MATADOR 120EC in the case of lambda cyhalothrin). As detailed above, pyrethroids are not normally leaf-mobile—they do not normally translocate. Surprisingly, in some exemplary embodiments, there is increased leaf mobility of the pyrethroid compound towards un-inoculated areas of a leafy green crop (e.g., lettuce) after inoculating other foliar surfaces (e.g., 10 days after). In some exemplary embodiments, there is increased leaf mobility or translocation of the pyrethroid in a leafy crop (e.g., lettuce) inoculated with a formulation containing nanoparticles of polymer-associated active ingredients via a 3 nozzle surround boom spray at a 15 GPA spray volume and a rate of 18 g/ha.

Hard Water/Fertilizer Applications

As described below, most traditional formulations produce solid particles (floc) or a precipitate when mixed in with high salt, hard water or fertilizer solutions. Surprisingly, a dispersed solid formulation of a pyrethroid (e.g., bifenthrin) of the present disclosure was stable (e.g. components, bifenthrin and the salt, remained dissolved, i.e., no visible precipitate or floc) when mixed with a concentrated/high salt solution (e.g. hard water, buffer, concentrated fertilizer formulation) for at least 3 hours. This was true even for waters with ionic strength as high as 8000 ppm $Mg^{2+}$ (a.k.a. CIPAC "G" hard water). For comparison, a commercially available solid formulation was also re-dispersed in the same manner but started to form flocs when mixed with the high salt solution within ten minutes. It is important to note that for such a mixture to be useful for the end user, the mixture should remain stable (i.e. no formation of sediments and/or flocs) within at least about 30-40 minutes—which is the time it takes for the mixture to be applied to the plant. It is surprising that the formulations of the present disclosure are stable in such high-salt conditions. Because the polymers that are used in the nanoparticles of the present disclosure are negatively charged, a practitioner of the art would expect the formulations of the present disclosure to flocculate when mixed with such a high amount of divalent salt. Without being limited by theory, it is believed that the increased stability of the formulations of the present disclosure arises from the use of nanoparticulate polymers as the delivery system and that if standard non-nanoparticle polymers were used then flocculation would occur.

Traditional solid or liquid formulations are not stable under conditions of high ionic (i.e., a high salt solution) strength. Sources of increased ionic strength can include, for example, mineral ions that are present in the water that a formulation is dispersed in. For example, in many cases the water that is available to a farmer is taken from a high-salt ("hard water") source such as a well or aquifer. Water that a grower uses can be variably hard and is normally measured as $Ca^{2+}$ equivalents. Ranges of water salinity can be from ~0 ppm $Ca^{2+}$ equivalent (deionized water) to 8000 ppm $Ca^{2+}$ or more.

Other sources of increased ionic strength can include, for example, other chemicals or materials that dispersed in the spray tank water before or after the addition of the pesticide formulation. Examples of this include mineral additives such as micronutrients (which can include e.g. B, Cu, Mn, Fe, Cl, Mo, Zn, S) or traditional N—P—K fertilizers where the nitrogen, phosphorus, or potassium source is in an ionic form as well as other agro-chemicals (e.g., pesticides, herbicides, etc.,). In some embodiments, the fertilizer can be 10-34-0 (N—P—K), optionally including one or more of sulfur, boron and another micronutrient. In some cases, the nitrogen source is in the form of urea or an agriculturally acceptable urea salt. The fertilizer can include e.g. ammonium phosphate or ammonium thiosulphate.

In some cases, the formulations of the present disclosure can be applied simultaneously with a high-salt solution or suspension such as a micronutrient solution or a fertilizer, pesticide, fungicide or herbicide solution or suspension (e.g. in furrow application). The ability to mix and apply pyrethroids with other agricultural ingredients such as liquid fertilizers is very useful to growers, as it reduces the number of required trips across crop fields and the expenditure of resources for application. In some cases, the formulations of the present disclosure may be mixed with liquid fertilizers of high ionic strength. In some cases the fertilizer is a 10-34-0 fertilizer, optionally including one or more of sulfur, boron and another micronutrient. In some cases, the nitrogen source is in the form of urea or an agriculturally acceptable urea salt. In some embodiments, the liquid fertilizer comprises a glyphosate or an agriculturally acceptable salt of glyphosate (e.g., ammonium, isopropylamine, dimethylamine or potassium salt). In some embodiments, the liquid fertilizer may be in the form of a solution or a suspension. In some embodiments, formulations of the present disclosure are stable when mixed with liquid fertilizers of increased or high ionic strength (e.g., at any of the ionic strengths described below). In some embodiments, when mixed with liquid fertilizers, formulations of the current disclosure show no signs of sedimentation or flocculation.

Other potential additives that might be added into a spray tank that are charged and can decrease the stability of an agrochemical formulation include charged surfactants or polymers, inert ingredients such as urea, or other similar ingredients.

In some embodiments, the present disclosure provides compositions of a formulation of nanoparticles of polymer-associated active ingredients that are redispersible in solutions with high ionic strength. In some embodiments, the present disclosure also provides formulations of nanoparticles of polymer-associated active ingredients that maintain their stability after being redispersed in water to which a high salt solution or solid salt is then added. In some embodiments, the formulations of the present disclosure are stable when dispersed in or dispersed in water and then mixed with solutions with ionic strength corresponding to $Ca^{2+}$ equivalents of about 0 to about 1 ppm, about 0 to about 10 ppm, about 0 to about 100 ppm, about 0 to about 342 ppm, about 0 to about 500 ppm, about 0 to about 1000 ppm, about 0 to about 5000 ppm, about 0 to about 8000 ppm, about 0 to about 10000 ppm, about 1 to about 10 ppm, about 1 to about 100 ppm, about 1 to about 342 ppm, about 1 to about 500 ppm, about 1 to about 1000 ppm, about 1 to about 5000 ppm, about 1 to about 8000 ppm, about 1 to about 10000 ppm, about 10 to about 100 ppm, about 10 to about 342 ppm, about 10 to about 500 ppm, about 10 to about 1000 ppm, about 10 to about 5000 ppm, about 10 to about 8000 ppm, about 10 to about 10000 ppm, about 100 to about 342 ppm, about 100 to about 500 ppm, about 100 to about 1000 ppm, about 100 to about 5000 ppm, about 100 to about 8000 ppm, about 100 to about 10000 ppm, about 342 to about 500 ppm, about 342 to about 1000 ppm, about 342 to about 5000 ppm, about 342 to about 8000 ppm, about 342 to about 10000 ppm, about 500 to about 1000 ppm, about 500 to about 5000 ppm, about 500 to about 8000 ppm, about 500 to about 10000 ppm, about 1000 to about 5000 ppm, about 1000 to about 8000 ppm, about 1000 to about 10000 ppm, about 5000 to about 8000 ppm, about 5000 to about 10000 ppm, about 8000 to about 10000 ppm.

Plant Health Applications

In some embodiments, application of formulations of the present disclosure (e.g., inoculation of crop plants or application to soil, as described in the specification) results in a yield increase (e.g., increased crop yield). In some embodiments, there is a yield increase compared to untreated plants (e.g., untreated crops). In some embodiments, there is an increase compared to plants that have been treated with a commercial formulation of the same active ingredient. In some embodiments, there is yield increase of about 2 to about 100%, e.g. 2-3%, 2-5%, 2-10%, 2-30%, 2-50%, 2-100%, 5-7%, 5-10%, 5-20%, 5-30%, 5-40%, 5-50%, 5-60%, 5-70%, 5-80%, 5-90%, 5-100%, 10-20%, 10- 30%, 10-40%, 10-50%, 10-60%, 10-70%, 10-80%, 10-90%, 20-40%, 20-60%, 20-80%, 20-100%, 30-50%, 30-60%, 30-80%, 30-100%, 40-60%, 40-80%, 40-100%, 50-80%, 50-100%, 60-80%, 60-100%, 70-90%, 70-100% or 80-100%. In some embodiments, the use of the pyrethroid formulations of the current results in a yield increase of greater than about 2%, greater than about 3%, greater than about 4%, greater than about 5%, greater than about 6%, greater than about 7%, greater than about 10%, greater than about 20%, greater than about 30%, greater than about 40%, greater than about 50%, greater than about 60%, greater than about 70%, greater than about 80%, greater than about 90% or greater than about 100%.

In some embodiments, inoculation of plants with formulations of the present disclosure provides an increased yield (e.g., increased crop yield) at active ingredient use rates that are lower than the use rates listed on the labels of commercially available pyrethroid products of the same active ingredient. In some embodiments, the increased yield can correspond to any of the values or ranges of values noted above. In some embodiments, the increased yield is obtained at an active ingredient use rate that is less about than 75%, less than about 60%, less than about 50%, less than about 40%, less than about 30%, less than about 20% or less than about 10% of a use rate listed on the label of a commercially available product of the same active ingredient. In some embodiments, the increased yield is obtained at an active ingredient use rate that is less about than 75%, less than about 60%, less than about 50%, less than about 40%, less than about 30%, less than about 20% or less than about 10% the minimum use rate of a range of use rates listed on the label of a commercially available product of the same active ingredient.

Direct Soil & Seed Applications

In some embodiments, formulations of the current disclosure may be used to control pests of plants via application to soil (inoculation of soil). In some embodiments, the formulations of the current disclosure may be used to control pests via application to the soil in which a plant is to be planted prior to planting (i.e., as pre-plant incorporated application). In some embodiments, the formulations of the current disclosure may be used to control pests via inoculation of the seed and soil at the time of seed planting (e.g., via an in-furrow application or T-banded application). In some embodiments, the formulations of the current disclosure may applied to the soil after planting but prior to emergence of the plant (i.e., as a pre-emergence application). In some embodiments, soil is inoculated with a formulation of the current disclosure via an aerosol spray or pouring. In some embodiments, the pyrethroid formulations of the current disclosure may be used to control pests in the aforementioned applications at an active ingredient use rate that is lower than a use rate listed on the label of a commercially available formulation of the same active ingredient. In some embodiments, a formulation of the current disclosure is used to control pests at an active ingredient use rate that is less than about 75%, less than about 60%, less than about 50%, less than about 40%, less than about 30%, less than about 20% or less than about 10% of the use rate listed on the label of a commercially available pyrethroid product of the same active ingredient. In some embodiments, a formulation of the current disclosure is used to control pests at an active ingredient use rate that is less than about 75%, less than about 60%, less than about 50%, less than about 40%, less than about 30%, less than about 20% or less than about 10% of the minimum use rate of a range of use rates listed on the label of a commercially available pyrethroid product of the same active ingredient.

In some embodiments, the pyrethroid formulations of the current disclosure can be used to control pests when applied to seeds. In some embodiments, the formulations of the current disclosure can be used to control pests when applied to seeds at active ingredient use rates that are less than the use rates of commercially available formulations of the same active ingredient. In some embodiments, a formulation of the current disclosure can be used to control pests when applied to seeds at an active ingredient use rate that is less than about 75%, less than about 60%, less than about 50%, less than about 40%, less than about 30%, less than about 20% or less than about 10% of a use rate listed on the label of a currently available commercial pyrethroid product of the same active ingredient. In some embodiments, a formulation of the current disclosure can be used to control pests when applied to seeds at an active ingredient use rate that is less than about 75%, less than about 60%, less than about 50%, less than about 40%, less than about 30%, less than about 20% or less than about 10% of the minimum use rate of a range of use rates listed on the label of a currently available commercial pyrethroid product of the same active ingredient.

Increased Re-Application Interval

Due to their enhanced efficacy and residual activity, in some embodiments, the formulations of the present disclosure can be used to control pests applied at greater time intervals (i.e. the time between distinct inoculations) than currently available formulations of the same active ingredient. Inoculation intervals (also referred to as intervals of repeat application, re-treatment intervals and the like) can be found on the labels of currently available commercial formulations and are readily accessible and available. In some embodiments, the formulations of the present disclosure are applied at an interval that is 1 day, 2 days, 3 days, 4 days, 5 days, 6 days, 7 days, 8 days, 9 days, 10 days, 11 days, 12 days, 13 days, 14 days or 15 days longer than commercial formulations of the same active ingredient. In some cases, commercial formulations are applied at intervals that correspond to a range of intervals (e.g., 7-14 days). In such cases, it is contemplated that the formulations of the present disclosure can be applied at a range of intervals whose shortest endpoint, longest endpoint, or both shortest and longest endpoints are longer than the corresponding endpoints of currently available commercial formulations by any of the values noted above. In some embodiments, the pyrethroid formulations of the present disclosure can be applied at an intervals of 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days or 40 days. In some embodiments, the formulations of the present disclosure can be applied at a range whose shortest and longest intervals (endpoints) are taken from any of the aforementioned values.

Specific Application (Plant & Pest)

As described above, the current disclosure provides methods of using formulations of nanoparticles of polymer-associated active ingredients, which in turn relate to application to specific plants and/or pests. The formulations may used to inoculate a target area of a plant or insect. In some embodiments, the formulations are used to inoculate a part or several parts of the plant, e.g., the leaves, stem, roots, flowers, bark, buds, shoots, and/or sprouts. In some embodiments, the formulations are used to inoculate a part or several parts of an insect, e.g., the head, eyes, maxilla, mandible, antennae, thorax, leg, wings and/or abdomen.

Generally, any method of application may be used including, dipping, spraying (from the ground or air), application to the soil adjacent to a plant or in an application area. Application methods may include adding formulation of the current disclosure to irrigation water and then applying to the plant. In some embodiments, the target organism (plant or insect) is inoculated by a formulation of the current disclosure by means of dipping the target organism or part of the organism into the dispersion containing the formulation. In some embodiments, the target organism is inoculated by means of an aerosol spray. In some embodiments, the target plant is inoculated is inoculated to by spraying a dispersion directly onto the leaves, stem, bud, shoot or flowers of the plant. In some embodiments, the target organism is inoculated by pouring a dispersion directly onto the root zone of a plant.

As pyrethroids are broad-spectrum insecticides, the formulations of the present disclosure can be used to control pests such as Lepidoptera (butterflies and moths such as cabbage looper and armyworms), diptera (flies such as mosquitoes and horn flies), siphonaptera (fleas), ixodida (ticks), blattaria (cockroaches), isoptera (termites), hymenoptera (bees, wasps, ants), hemiptera (true bugs such as aphids, scale insects, mealy bug), or coleoptera (beetles such as the Colorado potato beetle, or boll weevil) in addition to other insects that current pyrethroid products are used to control (such as those listed on the labels of commercially available pyrethroid formulations). Furthermore, the formulation of the present disclosure may be used to control any of the above listed pests as any life stage (e.g., egg, embryo, larva, pupa, imago, nymph, adult, etc.). The specific life stage or stages of pests that can be targeted by the formulations of the present disclosure depend, amongst other things, on the nature of active ingredient and the pest. Instructions related to targeting specific life stages of certain pests can often be found on the labels of commercially available pyrethroid products.

In some embodiments, the sucking insect pests to be targeted by formulations of pyrethroids prepared according to the current disclosure are *thrips* (insects from the order Thysanoptera, for example, *Frankliniella occidentalis* (Western Flower *Thrips*), *Heliothrips haemorrhoidalis* (Greenhouse *thrip*), *Thrips imaginis* (Plague *thrips*).

As detailed in the Examples below formulations of the current disclosure demonstrate increased efficacy (in comparison to commercially available formulations or pyrethroid applied "neat") against sap-sucking insects (e.g., *Lygus* spp). In some embodiments, the current disclosure provides formulations of pyrethroid compounds (e.g. bifenthrin) that have improved insect mortality to sap-sucking insects compared to e.g. commercially available formulations. In some embodiments, the sap-sucking insects are from the hemiptera family. In some embodiments, the sap-sucking insects are of the *Lygus* genus. In some embodiments, there is increased mortality in *hemipteran* species (e.g., *Lygus* species) that have been exposed to a formulation of nanoparticles of polymer associated active ingredients by a substrate (e.g. floral foam) inoculated with the formulation.

Similar to the improved efficacy generally described above, the formulations of the current disclosure also demonstrate increased efficacy against sap-sucking insects (e.g., *Lygus* species, *hemipteran* species) In some embodiments, the mortality is evaluated after 24, 48 or 72 hours. In some embodiments, the mortality corresponds to a decrease in the LC50 of the formulation by between 1.25 times and 5 times, e.g. as compared to a commercial available emulsion concentration formulation of the same active ingredient. In some embodiments, the increased mortality corresponds to a decrease in the LC50 of the formulation by between 1.5 times and 5 times. In some embodiments, the increased mortality corresponds to a decrease in the LC50 of the formulation by between 2.5 times and 5 times. In some embodiments, the increased mortality corresponds to a decrease in the LC50 of the formulation by between 3 times and 5 times. In some embodiments, the increased mortality corresponds to a decrease in the LC50 of the formulation by more than 5 times. In some embodiments, the increased mortality corresponds to a decrease in the LC50 of the formulation by between 2 times and 3 times.

In some embodiments, the current disclosure provides solid powder formulations that have increased efficacy against *hemipteran* species (e.g., *Lygus* species) as compared to, e.g. to neat pyrethroid alone or commercial formulations (e.g. Brigade® 2EC in the case of bifenthrin). In some embodiments, the current disclosure provides HSLS formulations that have increased efficacy against *hemipteran* species (e.g., *Lygus* species) as compared to, e.g. to neat pyrethroid alone or commercial formulations.

In some embodiments, the pests to be targeted by formulations of pyrethroids prepared according to the current disclosures are members of the subclass Acari. In some embodiments, the pests to be targeted by formulations of pyrethroids prepared according to the current disclosure are mites, such as those belonging to the suborder prostigmata, for example, *Bryobia rubrioculus* (Brown mite), *Polyphagotarsonemus latus* (Broad mite), *Brevipalpus lewisi* (Citrus Flat mite), *Eotetranychus sexmaculatus* (Six-spotted mite), *Penthaleus major* (Winter grain mite), *Petrobia latens* (Brown wheat mite), *Phytonemus pallidus* (Cyclamen Mite), *Tetranychus pacificus* (Pacific spider mite), *Tetranychus turkestani* (Strawberry spider mite), and those belonging to the genus *Rhizoglyphus*.

In some embodiments, there is increased mortality in mite species (e.g. two-spotted spider mites) that have been exposed to a portion of a plant (e.g. bean leaf) that has been inoculated with a formulation of nanoparticles of polymer-associated active ingredients via dipping, spraying or dripping.

In some embodiments, the current disclosure provides solid powder formulations that have increased efficacy against mite species (e.g. two-spotted spider mites) as compared to, e.g. to neat pyrethroid alone or commercial formulations (e.g. Brigade® 2EC in the case of bifenthrin). In some embodiments, the current disclosure provides HSLS formulations that have increased efficacy against mite species (e.g. two-spotted spider mites) as compared to, e.g. to neat pyrethroid alone or commercial formulations.

With respect to the plants to which formulations of the current disclosure can be applied, the formulations are generally applicable to any plant which pyrethroids are currently application. This may include agricultural and non-agricultural plants. In some agricultural embodiments, the plant is selected from the families fabaceaae, brassicaceae, rosaceae, solanaceae, convolvulaceae, poaceae, amaranthaceae, laminaceae and apiaceae.

In some embodiments, the plant is selected from plants that are grown for turf, sod, turf grasses grown for seed, pasture or ornamentals. In some embodiments, the plant is a crop, including but not limited to cereals (e.g. wheat, maize (including but not limited to field corn sweet corn, pop corn etc.) rice, barley, oats etc.), soybean, cole crops, tobacco, oil crops, cotton, fruit (e.g. pome fruits such as but not limited to apples and pears), vine crops (e.g. cucurbits), legume vegetables, bulb vegetables, rapeseed, potatoes, greenhouse crops and all other crops on which pyrethroids are known to control insects. In some embodiments, the plant is grown for seed (e.g., corn grown for seed). Lists of plants on which fungal diseases are controlled by specific commercially available pyrethroid formulations can be found on their labels, which are readily accessible and available via numerous sources, as described above. The formulations can also be used to protect trees in silviculture or horticulture. Examples of pests controlled by commercially available pyrethroid formulations are provided in other sections of the specification.

In some embodiments, the formulations of the present disclosure can be used to protect agricultural crops as well as non-agricultural plants. For example, pests can be controlled on crops such as those described above, pasture, turf, ornamentals, and other plants that current pyrethroid products are used to control pests on.

In some embodiments, the formulations of the current disclosure are used to control pests in turf, ornamental and non-crop applications (uses). Examples of these applications can be found on the labels of currently available pyrethroid formulations, such as the labels referenced in other portions of the specification. Non-limiting examples of pasture, turf, ornamental and non-crop applications in which the formulations of the present disclosure can be used include pest control in buildings and structures (including indoor, perimeter, structural and subterranean pest control) and aircraft.

Other examples include the control of pests of turf (e.g. lawns and sod) in residential areas, athletic fields, parks, and recreational areas such as golf courses. Formulations of the current disclosure may also be used to control pests of ornamentals (e.g. shrubs, ornamental trees, foliage plants etc.), including ornamentals in or around any of the aforementioned areas, as well as in greenhouses (e.g. those used for growth of ornamentals). Examples of pests that can be controlled in turf, ornamental and non-crop applications, include those listed as pests turf, ornamental and non-crop applications in any other portion of the specification or in any of the labels of currently available pyrethroid products used to control pests in turf, ornamental and non-crop applications (such as the those referenced in other portions of the specification). In some embodiments, the formulations of the current disclosure may be use to control public health pests such as fleas, ticks and mosquitoes.

Specific Commercial Applications (Crop, Active, dose, Application & Formulation)

As used herein, "a range of rates" listed on the label of a commercially available product refers to a rate range listed for the control of a pest or pests in a certain application (e.g. on a crop). For example, the labeled use rate for the control of *Spodoptera frugiperda* on cotton by Talstar® 100 EC is 50-60 g/ha, which is a "range of rates."

Bifenthrin

In various embodiments, the bifenthrin formulations of the current disclosure may be used to control pests at active ingredient use rates that are lower than the use rates listed on the labels of commercially available bifenthrin products. In some embodiments, a bifenthrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available bifenthrin product.

Labels of commercially available bifenthrin products often provide ranges of active ingredient use rates to control pests. In some embodiments, the bifenthrin formulations of the current disclosure may be used to control pests at an active ingredient use rate that is lower than the minimum use rate of a range of use rates listed on the label of a commercially available bifenthrin product. In some embodiments a bifenthrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Bifenthrin—Soybean

Labeled use rates for the control of various pests of soybean by Brigade®2EC and Talstar®100EC, two commercially available bifenthrin emulsion concentrates, are provided in Table 5.

TABLE 5

Active ingredient use rates for the control of pests by commercially available bifenthrin products.

| Product | Target Pests | Use Rate (g ai/ha) | Re-Application interval |
|---------|--------------|--------------------|--------------------------|
| Brigade ® 2EC | Alfalfa Caterpillar, Aphids, Aster Leafhopper, Bean Leaf Beetle, Beet Armyworm, Cloverworm, Corn Earworm, Corn Rootworm (adult), Cucumber Beetles, Cutworms, European Corn Borer, Fall Armyworm, | 37-112 | N/A |

TABLE 5-continued

Active ingredient use rates for the control of pests by commercially available bifenthrin products.

| Product | Target Pests | Use Rate (g ai/ha) | Re-Application interval |
|---|---|---|---|
| | Flea Beetle, Grasshoppers, Imported Cabbageworm, Japanese Beetle (Adult), Leafhoppers, Leafminer, Loopers, Mexican Bean Beetle (adult), Pea Leaf Weevil, Pea Weevil, Plant Bug, Saltmarsh Caterpillar, Sap Beetle, Southern Armyworm, Stink Bugs, Tarnished Plant Bug, Thrips, Tobacco budworm, Webworms, Western Bean Cutworm, Whitefly, Yellowstriped armyworm | | |
| | *Lygus* species, Whitefly, Two Spotted Spider Mite | 90-112 | |
| Talstar ® 100EC | *Anticarsia gemmatalis* (Defoliating caterpillar, soybean caterpillar) | 2-5 | |
| | *Nezara viridula* (Soybean stink bug, Green stink bug) | 10-16 | |

In some embodiments, the bifenthrin formulations of the current disclosure may be used to control pests of soybean at active ingredient use rates that are lower than use rates listed on the labels of commercially available bifenthrin pesticides. In some embodiments, a bifenthrin formulation of the current disclosure may be used to control pests of soybean at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests of soybean at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

In some embodiments, the bifenthrin formulations of the current disclosure may be used to control pests of soybean at an active ingredient use rate of about 28-about 84 g/ha, about 22-about 67 g/ha, about 18-about 56 g/ha, about 15-about 45 g/ha, about 11-about 34 g/ha, about 7-about 22 g/ha or about 4-about 11 g/ha.

In some embodiments, the bifenthrin formulations of the current disclosure may be used to control pests of soybean at an active ingredient use rate of less than about 28 g/ha, less than about 22 g/ha, less than about 18 g/ha, less than about 15 g/ha, less than about 11 g/ha, less than about 7 g/ha or less than about 4 g/ha.

In some embodiments, the bifenthrin formulations of the current disclosure may be used to control pests of soybean at an active ingredient use rate of about 67-about 84 g/ha, about 54-about 67 g/ha, about 45-about 56 g/ha, about 36-about 45 g/ha, about 27-about 34 g/ha, about 18-about 22 g/ha or about 9-about 11 g/ha.

In some embodiments, the bifenthrin formulations of the current disclosure may be used to control pests of soybean at an active ingredient use rate of less than about 67 g/ha, less than about 54 g/ha, less than about 45 g/ha, less than about 36 g/ha, less than about 27 g/ha, less than about 18 g/ha or less than about 9 g/ha.

In some embodiments, the bifenthrin formulations of the current disclosure may be used to control pests of soybean at an active ingredient use rate of about 1.5-about 3.8 g/ha, about 1.2-about 3.0 g/ha, about 1.0-about 2.5 g/ha, about 0.8-about 2.0 g/ha, about 0.6-about 1.5 g/ha, about 0.4-about 1.0 g/ha or about 0.2-about 0.5 g/ha.

In some embodiments, the bifenthrin formulations of the current disclosure may be used to control pests of soybean at an active ingredient use rate of less than about 1.5 g/ha, less than about 1.2 g/ha, less than about 1.0 g/ha, less than about 0.8 g/ha, less than about 0.6 g/ha, less than about 0.4 g/ha or less than about 0.2 g/ha.

In some embodiments, the bifenthrin formulations of the current disclosure may be used to control pests of soybean at an active ingredient use rate of about 7.5-about 12 g/ha, about 6-about 9.6 g/ha, about 5-about 8 g/ha, about 4-about 6.4 g/ha, about 3-about 4.8 g/ha, about 2-about 3.2 g/ha or about 1-about 1.6 g/ha.

In some embodiments, the bifenthrin formulations of the current disclosure may be used to control pests of soybean at an active ingredient use rate of less than about 7.5 g/ha, less than about 6 g/ha, less than about 5 g/ha, less than about 4 g/ha, less than about 3 g/ha, less than about 2 g/ha or less than about 1 g/ha.

Non-limiting examples of pests of soybeans that may be controlled with bifenthrin formulations of the current disclosure include those listed in Table 5, above, and pests of soybeans listed on the labels of currently available bifenthrin products.

Bifenthrin—Cotton

Labeled use rates for the control of various pests of cotton by Brigade®2EC and Talstar®100EC, two commercially available bifenthrin emulsion concentrates, are provided in Table 6.

TABLE 6

Active ingredient use rates for the control of pests of cotton by bifenthrin products.

| Product | Target Pests | Use Rate (g ai/ha) | Re-Application interval |
|---|---|---|---|
| Brigade ® 2EC | European Corn Borer, Soybean (Banded) Thrips, Tobacco Thrips | 22-112 | |
| | Boll Weevil, Bollworm, Cabbage Looper, Cotton Aphid, Cotton Fleahopper, Cotton Leaf perforator, Cutworms, Fall Armyworm, Plant Bug, Saltmarsh Caterpillar, Southern Garden Leafhopper, Stink Bugs, Tobacco Budworm, Whitefly, Yellow Striped Armyworm | 45-112 | Control of boll weevil: 3-4 days "until [pests] are reduced to acceptable levels." To control mites and aphids: repeat as necessary |
| | Beet Armyworm, Carmine Spider Mite, Western Plant Bug, Pink Bollworm, Two-spotted Spider Mite | 67-112 | Mites (see above) |
| Talstar ® 100EC | *Alabama argillacea* (leafworm, cotton leafworm), | 30 | |
| | *Anthonomus grandis* (Boll Weevil) | 50 | For control of Boll Weevil: Not more than 5 days |
| | *Bemisia tabaci* strain B (whitefly) | 50-100 | |
| | *Spodoptera frugiperda* (fall armyworm) | 50-60 | |
| | *Tetranychus urticae* (spider mite) | 55-60 | |

In some embodiments, the bifenthrin formulations of the current disclosure may be used to control pests of cotton at active ingredient use rates that are lower than use rates listed on the labels of commercially available bifenthrin pesticides. In some embodiments, a bifenthrin formulation of the current disclosure may be used to control pests of cotton at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests of cotton at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

In some embodiments, the bifenthrin formulations of the current disclosure may be used to control pests of cotton at an active ingredient use rate of about 17-about 84 g/ha, about 13-about 67 g/ha, about 11-about 56 g/ha, about 9-about 45 g/ha, about 7-about 34 g/ha, about 4.5-about 22 g/ha or about 2-about 11 g/ha.

In some embodiments, the bifenthrin formulations of the current disclosure may be used to control pests of cotton at an active ingredient use rate of less than about 17 g/ha, less than about 13 g/ha, less than about 11 g/ha, less than about 9 g/ha, less than about 7 g/ha, less than about 4.5 g/ha or less than about 2 g/ha.

In some embodiments, the bifenthrin formulations of the current disclosure may be used to control pests of cotton at an active ingredient use rate of about 34-about 84 g/ha, about 27-about 67 g/ha, about 22-about 56 g/ha, about 18-about 45 g/ha, about 13.5-about 34 g/ha, about 9-about 22 g/ha or about 4.5-about 11 g/ha.

In some embodiments, the bifenthrin formulations of the current disclosure may be used to control pests of cotton at an active ingredient use rate of less than about 34 g/ha, less than about 27 g/ha, less than about 22 g/ha, less than about 18 g/ha, less than about 13.5 g/ha, less than about 9 g/ha or less than about 4.5 g/ha.

In some embodiments, the bifenthrin formulations of the current disclosure may be used to control pests of cotton at an active ingredient use rate of about 50-about 84 g/ha, about 40-about 67 g/ha, about 34-about 56 g/ha, about 27-about 45 g/ha, about 20-about 34 g/ha, about 13-about 22 g/ha or about 7-about 11 g/ha.

In some embodiments, the bifenthrin formulations of the current disclosure may be used to control pests of cotton at an active ingredient use rate of less than about 50 g/ha, less than about 40 g/ha, less than about 34 g/ha, less than about 27 g/ha, less than about 20 g/ha, less than about 13 g/ha or less than about 7 g/ha.

In some embodiments, the bifenthrin formulations of the current disclosure may be used to control pests of cotton at an active ingredient use rate of about 37.5-about 75 g/ha, about 30-about 60 g/ha, about 25-about 50 g/ha, about 20-about 40 g/ha, about 15-about 30 g/ha, about 10-about 20 g/ha or about 5-about 10 g/ha.

In some embodiments, the bifenthrin formulations of the current disclosure may be used to control pests of cotton at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

In some embodiments, the bifenthrin formulations of the current disclosure may be used to control pests of cotton at an active ingredient use rate of about 37.5-about 45 g/ha, about 30-about 36 g/ha, about 25-about 30 g/ha, about 20-about 24 g/ha, about 15-about 18 g/ha, about 10-about 12 g/ha or about 5-about 6 g/ha.

In some embodiments, the bifenthrin formulations of the current disclosure may be used to control pests of cotton at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

In some embodiments, the bifenthrin formulations of the current disclosure may be used to control pests of cotton at an active ingredient use rate of about 41-about 45 g/ha, about 33-about 36 g/ha, about 27.5-about 30 g/ha, about 22-about 24 g/ha, about 16.5-about 18 g/ha, about 11-about 12 g/ha or about 5.5-about 6 g/ha.

In some embodiments, the bifenthrin formulations of the current disclosure may be used to control pests of cotton at an active ingredient use rate of less than about 41 g/ha, less than about 33 g/ha, less than about 27.5 g/ha, less than about 22 g/ha, less than about 16.5 g/ha, less than about 11 g/ha or less than about 5.5 g/ha.

In some embodiments, the bifenthrin formulations of the current disclosure may be used to control pests of cotton at an active ingredient use rate of less than about 22.5 g/ha, less than about 18 g/ha, less than about 15 g/ha, less than about 12 g/ha, less than about 9 g/ha, less than about 6 g/ha or less than about 3 g/ha.

In some embodiments, the bifenthrin formulations of the current disclosure may be used to control pests of cotton at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

Non-limiting examples of pests of cotton that can be controlled with bifenthrin formulations of the current disclosure include those listed in Table 6, above, and pests of cotton listed on the labels of currently available bifenthrin products.

Bifenthrin—Turf, Ornamental and Non-Crop Applications

In some embodiments, the bifenthrin formulations of the current disclosure may be used in turf, ornamental and non-crop pest control applications. Examples of such applications are found on the label of Talstar® P Professional Insecticide, a commercially available bifenthrin product, and include but are not limited to the control of pests of turf (e.g., lawn), ornamentals (shrubs, ornamental trees, foliage plants etc.), buildings (indoor and perimeter pest control), parks and athletic fields. Other examples of turf, ornamental and non-crop pest control applications in which the bifenthrin formulations of the current disclosure may be used include those found on the labels of other commercially available bifenthrin products, as well as applications noted in any portion of the specification.

In some embodiments, the bifenthrin formulations of the current disclosure may be used to control pests in turf, ornamental and non-crop applications at active ingredient use rates that are lower than use rates listed on the labels of commercially available bifenthrin pesticides. In some embodiments, a bifenthrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests in turf, ornamental and non-crop applications at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

Bifenthrin—Turf, Ornamental and Non-Crop Applications—Lawn Care

Labeled use rates for the control of various pests of lawns by Talstar® P Professional Insecticide, a commercially available bifenthrin suspension concentrate, are provided below.

TABLE 7

Active ingredient use rates for the control of lawn pests by Talstar® P Professional Insecticide

| Product | Target Pests | Use Rate (g ai/ha) | Re-application Interval |
|---|---|---|---|
| Talstar® P Professional Insecticide | Armyworms, Cutworms, Sod Webworm | 46-64 | |
| | Annual Bluegrass Weevil (Hyperodes) (Adult), Banks Grass Mite, Billbugs (Adult), Black Turfgrass *Ataenius* (Adult), Centipedes, Crickets, Earwigs, Fleas (Adult), Grasshoppers, Leafhoppers, Mealybugs, Millipedes, Mites, Pillbugs, Sowbugs | 64-127 | Mites: 5-7 days if necessary |
| | Crane Flies | 127 | |
| | Ants, Fleas (Larvae), Chinch Bugs, Imported Fire Ants, Japanese Beetle (Adult), Mole Cricket (Adult), Mole Cricket (Nymph), Ticks | 127-254 | Ticks: Not more than once every 7 days |

In some embodiments, the bifenthrin formulations of the current disclosure may be used to control lawn pests at active ingredient use rates that are lower than use rates listed on the labels of commercially available bifenthrin pesticides. In some embodiments, a bifenthrin formulation of the current disclosure may be used to control lawn pests at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control lawn pests at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

In some embodiments, the bifenthrin formulations of the current disclosure may be used to control lawn pests at an active ingredient use rate of about 34-about 48 g/ha, about 27-about 38 g/ha, about 22-about 32 g/ha, about 18-about 25 g/ha, about 14-about 19 g/ha, about 9-about 12 g/ha or about 4-about 6 g/ha.

In some embodiments, the bifenthrin formulations of the current disclosure may be used to control lawn pests at an active ingredient use rate of less than about 34 g/ha, less than about 27 g/ha, less than about 22 g/ha, less than about 18 g/ha, less than about 14 g/ha, less than about 9 g/ha or less than about 4 g/ha.

In some embodiments, the bifenthrin formulations of the current disclosure may be used to control lawn pests at an active ingredient use rate of about 47-about 95 g/ha, about 38-about 76 g/ha, about 32-about 64 g/ha, about 25-about 51 g/ha, about 19-about 38 g/ha, about 12-about 25 g/ha or about 6-about 13 g/ha.

In some embodiments, the bifenthrin formulations of the current disclosure may be used to control lawn pests at an active ingredient use rate of less than about 47 g/ha, less than about 38 g/ha, less than about 32 g/ha, less than about 25 51 g/ha, less than about 19 g/ha, less than about 12 g/ha or less than about 6 g/ha.

In some embodiments, the bifenthrin formulations of the current disclosure may be used to control lawn pests at an active ingredient use rate of about 95-about 190 g/ha, about 76-about 153 g/ha, about 64-about 127 g/ha, about 51-about 102 g/ha, about 38-about 76 g/ha, about 25-about 51 g/ha or about 13-about 25 g/ha.

In some embodiments, the bifenthrin formulations of the current disclosure may be used to control lawn pests at an active ingredient use rate of less than about 95 g/ha, less than about 76 g/ha, less than about 64 g/ha, less than about 51 g/ha, less than about 38 g/ha, less than about 25 g/ha or less than about 13 g/ha.

Non-limiting examples of pests of lawns that can be controlled with bifenthrin formulations of the current disclosure include those listed in Table 7, above, and pests of lawns listed on the labels of other currently available bifenthrin products.

The aforementioned rates can be converted to alternative units suited to applications on smaller areas (e.g. g ai per 100 m², g ai per 1000 m² etc.) via standard conversion factors.

Bifenthrin—Turf and Ornamental and Non-Crop Applications—Ornamental and Greenhouse Labeled use rates for the control of various pests of ornamentals and greenhouses by Talstar® P Professional Insecticide, a commercially available bifenthrin suspension concentrate, are provided below.

TABLE 8

Active ingredient use rates for the control of ornamental and greenhouse pests by Talstar ® P Professional Insecticide

| Product | Target Pests | Use Rate (g ai/ha) | Re-application interval |
|---|---|---|---|
| by Talstar ® P Professional Insecticide | Bagworms, Cutworms, Elm Leaf Beetles, Fall Webworms, gypsy moth caterpillars, Lace Bugs, Leaf Feeding, Plant Bugs, Tent Caterpillars | 32-64 | As necessary |
| | Adelgids, Aphids, Bees, Beet Armyworm, Black Vine Weevil (Adults), Brown Soft Scales, Broad Mites, Budworms, California Red Scale (Crawlers), Centipedes, Cicadas, Citrus Thrips, Clover Mites, Crickets, Diaprepes (adults), Earwigs, European Red Mite, Flea Beetles, Fungus Gnats (adults), Grasshoppers, Japanese Beetle (adults), Leafhoppers, Leafrollers, Mealybugs, Millipedes, Mites, Orchid Weevil, Pillbugs, Plant Bugs (including *Lygus* spp.), Psyllids, Scale crawlers, such as California scale, San Jose Scale, etc., Scorpions, Sowbugs, Spider Mites, Spiders, Thrips, Tip Moths, Treehoppers, Twig Borers, Wasps, Weevils, Whiteflies | 64-127 | As necessary |

TABLE 8-continued

Active ingredient use rates for the control of ornamental and greenhouse pests by Talstar ® P Professional Insecticide

| Product | Target Pests | Use Rate (g ai/ha) | Re-application interval |
|---|---|---|---|
| | Ants, Imported Fire Ants, Leafminers, Pecan Leaf Scorch Mite, Pine Shoot Beetle (adults), Sawfly larvae, Spider Mites, Stink Bugs | 127-254 | As necessary |
| | Mosquitoes | 84-254 | Mosquitoes: For lower use rates: Not more than once per seven days For highest use rate: not more than once per four weeks |

In some embodiments, the bifenthrin formulations of the current disclosure may be used to control lawn pests of ornamentals and greenhouses at active ingredient use rates that are lower than use rates listed on the labels of commercially available bifenthrin pesticides. In some embodiments, a bifenthrin formulation of the current disclosure may be used to control pests of ornamentals and greenhouses at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests of ornamentals and greenhouses at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

In some embodiments, the bifenthrin formulations of the current disclosure may be used to control ornamental and greenhouse pests at an active ingredient use rate of about 24-about 48 g/ha, about 19-about 38 g/ha, about 16-about 32 g/ha, about 12-about 25 g/ha, about 10-about 19 g/ha, about 6-about 12 g/ha or about 3-about 6 g/ha.

In some embodiments, the bifenthrin formulations of the current disclosure may be used to control ornamental and greenhouse pests at an active ingredient use rate of less than about 24 g/ha, less than about 19 g/ha, less than about 16 g/ha, less than about 12 g/ha, less than about 10 g/ha, less than about 6 g/ha or less than about 3 g/ha.

In some embodiments, the bifenthrin formulations of the current disclosure may be used to control ornamental and greenhouse pests at an active ingredient use rate of about 48-about 95 g/ha, about 38-about 76 g/ha, about 32-about 64 g/ha, about 25-about 51 g/ha, about 19-about 38 g/ha, about 13-about 25 g/ha or about 6-about 13 g/ha.

In some embodiments, the bifenthrin formulations of the current disclosure may be used to control ornamental and greenhouse pests at an active ingredient use rate of less than about 48 g/ha, less than about 38 g/ha, less than about 32 g/ha, less than about 25 g/ha, less than about 19 g/ha, less than about 13 g/ha or less than about 6 g/ha.

In some embodiments, the bifenthrin formulations of the current disclosure may be used to control ornamental and greenhouse pests at an active ingredient use rate of about 95-about 191 g/ha, about 76-about 153 g/ha, about 64-about 127 g/ha, about 51-about 102 g/ha, about 38-about 76 g/ha, about 25-about 51 g/ha or about 13-about 25 g/ha.

In some embodiments, the bifenthrin formulations of the current disclosure may be used to control ornamental and greenhouse pests at an active ingredient use rate of less than about 95 g/ha, less than about 76 g/ha, less than about 64 g/ha, less than about 51 g/ha, less than about 38 g/ha, less than about 25 g/ha or less than about 13 g/ha.

In some embodiments, the bifenthrin formulations of the current disclosure may be used to control ornamental and greenhouse pests at an active ingredient use rate of about 63-about 191 g/ha, about 50-about 153 g/ha, about 42-about 127 g/ha, about 34-about 102 g/ha, about 25-about 76 g/ha, about 16-about 51 g/ha or about 8-about 25 g/ha.

In some embodiments, the bifenthrin formulations of the current disclosure may be used to control ornamental and greenhouse pests at an active ingredient use rate of less than about 63 g/ha, less than about 50 g/ha, less than about 42 g/ha, about 34 g/ha, less than about 25 g/ha, less than about 16 g/ha or less than about 8 g/ha.

Non-limiting examples of ornamental and greenhouse pests that can be controlled with bifenthrin formulations of the current disclosure include those listed in Table 8, above, and ornamental and greenhouse pests listed on the labels of other currently available bifenthrin products.

The aforementioned rates can be converted to alternative units suited to applications on smaller areas (e.g. g ai per 100 $m^2$, g ai per 1000 $m^2$ etc.) via standard conversion factors.

Bifenthrin—Fruits and Vegetables

In some embodiments, the bifenthrin formulations of the current disclosure may be used to control pests of fruits and vegetables at active ingredient use rates that are lower than use rates listed on the labels of commercially available bifenthrin pesticides. In some embodiments, a bifenthrin formulation of the current disclosure may be used to control pests of fruits and vegetables at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests of fruits and vegetables at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

Examples of fruits and vegetables on which pests can be controlled by bifenthrin formulations of the current disclosure can be found on the labels of commercially available bifenthrin products (e.g. Brigade®2EC, Talstar®100EC). The fruits and vegetables on which pest may be controlled by formulations of the current disclosure include but are not limited to cole crops (Brassicas), Cucurbits, peas and beans, lettuce, berries, pears, potatoes, grapes and others. Examples of pests that may be controlled on a particular type of fruit or vegetable include pests controlled on that particular type of fruit or vegetable by commercially available bifenthrin formulations. Such information can also be found on the labels of commercially available bifenthrin formulations (e.g. Brigade®2EC, Talstar®100EC).

Bifenthrin—Corn

Labeled use rates for the control of various pests of field corn and popcorn via foliar application by Brigade®2EC, a commercially available bifenthrin emulsion concentrate, are provided in Table 9.

TABLE 9

Active ingredient use rates for the control of pests of field corn and popcorn via foliar application of Brigade ® 2EC

| Product | Target Pests | Use Rate (g ai/ha) | Re-Application Interval |
|---|---|---|---|
| Brigade ® 2EC | Aphids, Army Cutworm, Beet Armyworm, Cereal Leaf Beetle, Chinch Bug, Common Stalk Borer, Corn Earworm, Corn Rootworm (Adults), Cucumber Beetle (Adults), Cutworm Species, European Corn Borer, Fall Armyworm, Flea Beetle, Grasshoppers, Greenbug, Japanese Beetle (Adult), Sap Beetle, Southern Armyworm, Southern Corn Leaf Beetle, Southwestern Corn Borer, Stinkbugs, Tarnished Plant Bug, True Armyworm or Armyworm Species, Webworms, Western Bean Cutworm, Yellowstriped Armyworm, | 37-112 | Various insect pests: repeat as necessary |
| | Banks Grass Mite, Carmine Mite, Two Spotted Spider Mite | 90-112 | |

In some embodiments, the bifenthrin formulations of the current disclosure may be used to control pests of corn at active ingredient use rates that are lower than use rates listed on the labels of commercially available bifenthrin pesticides. In some embodiments, a bifenthrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available bifenthrin product.

In some embodiments, a bifenthrin formulation of the current disclosure may be used to control pests of corn at an active ingredient use rate that is lower than the minimum use rate of a range of use rates listed on the label of a commercially available bifenthrin product. In some embodiments a bifenthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available bifenthrin product.

In some embodiments, the bifenthrin formulations of the current disclosure may be used to control pests of corn at an active ingredient use rate of about 28-about 84 g/ha, about 22-about 67 g/ha, about 18-about 56 g/ha, about 14-about 45 g/ha, about 11-about 34 g/ha, about 7-about 22 g/ha or about 4-about 11 g/ha. In some embodiments, the bifenthrin formulations of the current disclosure may be used to control pests of corn at an active ingredient use rate of about 67-about 84 g/ha, about 53-about 67 g/ha, about 45-about 56 g/ha, about 36-about 45 g/ha, about 27-about 34 g/ha, about 18-about 22 g/ha or about 9-about 11 g/ha.

In some embodiments, the bifenthrin formulations of the current disclosure may be used to control pests of corn at an active ingredient use rate of less than about 28 g/ha, less than about 22 g/ha, less than about 18 g/ha, less than about 14 g/ha, less than about 11 g/ha, less than about 7 g/ha or less than about 4 11 g/ha. In some embodiments, the bifenthrin formulations of the current disclosure may be used to control pests of corn at an active ingredient use rate of less than about 67 g/ha, less than about 53 g/ha, less than about 45 g/ha, less than about 36 g/ha, less than about 27 g/ha, less than about 18 g/ha or less than about 9 g/ha.

Non-limiting examples of pests of soybeans that can be controlled with bifenthrin formulations of the current disclosure include those listed in Table 9, above, and pests of corn listed on the labels of currently available bifenthrin products.

Lambda-Cyhalothrin

In various embodiments, the lambda-cyhalothrin formulations of the current disclosure may be used to control pests at active ingredient use rates that are lower than the use rates listed on the labels of commercially available lambda-cyhalothrin products. In some embodiments, a lambda-cyhalothrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available lambda-cyhalothrin product.

Labels of commercially available lambda-cyhalothrin products often provide ranges of active ingredient use rates to control pests. In some embodiments, the lambda-cyhalothrin formulations of the current disclosure may be used to control pests at an active ingredient use rate that is lower than the minimum use rate of a range of use rates listed on the label of a commercially available lambda-cyhalothrin product. In some embodiments a lambda-cyhalothrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Lambda-Cyhalothrin—Soybean

Labeled use rates for the control of various pests of soybean by Karate® with Zeon Technology™ and Karate Zeon® 250 CS, two commercially available lambda-cyhalothrin capsule suspensions, are provided in Table 10.

In some embodiments, a lambda-cyhalothrin formulation of the current disclosure may be used to control pests of soybean at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of soybean at an active ingredient use rate of about 13-about 22 g/ha, about 10.5-about 17 g/ha, about 9-about 15 g/ha, about 7-about 12 g/ha, about 5-about 9 g/ha, about 3.5-about 6 g/ha or about 2-about 3 g/ha. In some embodiments, the lambda-cyhalothrin formulations of the current disclosure may be used to control pests of soybean at an active ingredient use rate of about 22-about 26 g/ha, about

TABLE 10

Active ingredient use rates for the control of soybean by Karate with Zeon Technology ® and Karate Zeon ® 250 CS.

| Product | Target Pests | Use Rate (g ai/ha) | Re-Application Interval |
|---|---|---|---|
| Karate ® with Zeon Technology ™ | Bean Leaf Beetle, Cabbage Looper Corn Earworm, Cutworm spp., Green Cloverworm, Mexican Bean Beetle, Mexican Corn Rootworm Beetle (Adult), Northern Corn Rootworm Beetle (Adult), Painted Lady (Thistle) Caterpillar, Potato Leafhopper, Saltmarsh Caterpillar, Southern Corn Rootworm Beetle (Adult), Soybean Aphids, Three-cornered Alfalfa Hopper, Thrips, Velvetbean Caterpillar, Western Corn Rootworm Beetle (Adult), Woollybear Caterpillar | 17-29 | As required (determined by scouting), usually 5 or more days |
| | Armyworm, Blister Beetle spp., European Corn Borer, Fall Armyworm, Grasshopper species, Japanese Beetle (Adult), Plant Bug species, Silver-spotted Skipper, Stink Bug species, Tobacco Budworm, Webworm species, Yellowstriped Armyworm | 29-35 | As required (determined by scouting), usually 5 or more days |
| | Beet Armyworm, Lesser Cornstalk Borer, Soybean Looper, Spider Mites | 35 | As required (determined by scouting), usually 5 or more days |
| Karate Zeon ® 250 CS | Soybean caterpillar (*Anticarsia gemmatalis*) | 3.75 | |
| | Cucurbit Beetle (*Diabrotica speciosa*), Soybean stink bug, Green stink bug (*Nezara viridula*) | 7.5 | |

In some embodiments, the lambda-cyhalothrin formulations of the current disclosure may be used to control pests of soybean at active ingredient use rates that are lower than use rates listed on the labels of commercially available lambda-cyhalothrin pesticides. In some embodiments, a lambda-cyhalothrin formulation of the current disclosure may be used to control pests of soybean at a use rate that is less than about 75%, less than about 60%, less than about 50%, less than about 40%, less than about 30%, less than about 20% or less than about 10% of a use rate listed on the label of a commercially available lambda-cyhalothrin product.

17-about 21 g/ha, about 15-about 17 g/ha, about 12-about 14 g/ha, about 9-about 10.5 g/ha, about 6-about 7 g/ha, or about 3-about 3.5 g/ha.

In some embodiments, the lambda-cyhalothrin formulations of the current disclosure may be used to control pests of soybean at an active ingredient use rate of less than about 13 g/ha, less than about 10.5 g/ha, less than about 9 g/ha, less than about 7 g/ha, less than about 5 g/ha, less than about 3.5 g/ha or less than about 2 g/ha. In some embodiments, the lambda-cyhalothrin formulations of the current disclosure may be used to control pests of soybean at an active ingredient use rate of less than about 22 g/ha, less than about 17 g/ha, less than about 15 g/ha, less than about 12 g/ha, less than about 9.5 g/ha, less than about 6 g/ha, or less than about 3 g/ha. In some embodiments, the lambda-cyhalothrin formulations of the current disclosure may be used to control pests of soybean at an active ingredient use rate of less than about 26 g/ha, less than about 21 g/ha, less than about 17 g/ha, less than about 14 g/ha, less than about 10.5 g/ha, less than about 7 g/ha or less than about 3.5 g/ha.

Non-limiting examples of pests of soybeans that can be controlled with lambda-cyhalothrin formulations of the current disclosure include those listed in Table 10, above, and other pests of soybeans listed on the labels of currently available lambda-cyhalothrin products.

Lambda-Cyhalothrin—Cereals

Labeled use rates for the control of various pests of various cereals by Karate® with Zeon Technology™ a commercially available lambda-cyhalothrin capsule suspension, are provided in Table 11.

TABLE 11

Active ingredient use rates for the control of pests of barley, buckwheat, oats, rye, triticale, wheat and wheat hay with Karate with Zeon Technology ®

| Product | Target Pests | Use Rate (g ai/ha) | Re-Application Interval |
| --- | --- | --- | --- |
| Karate ® with Zeon Technology ™ | Army Cutworm, Cutworm species | 17-29 | As required (determined by scouting), usually 5 or more days |
| | Armyworm, Bird Cherry-Oat Aphid, Cereal Leaf Beetle, English Grain Aphid, Fall Armyworm, Flea Beetle species, Grasshopper species, Hessian Fly, Orange Blossom Wheat Midge, Russian Wheat Aphid, Stink Bug species, Yellowstriped Armyworm | 23-35 | As required (determined by scouting), usually 5 or more days |
| | Grass Sawfly | 29-35 | |
| | Chinch Bug, Corn Leaf Aphid, Greenbug, Mite species | 35 | |

In some embodiments, the lambda-cyhalothrin formulations of the current disclosure may be used to control pests of cereals at active ingredient use rates that are lower than use rates listed on the labels of commercially available lambda-cyhalothrin pesticides. In some embodiments, a lambda-cyhalothrin formulation of the current disclosure may be used to control pests of cereals at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests of cereals at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of cereals at an active ingredient use rate of about 13-about 22 g/ha, about 10.5-about 17 g/ha, about 9-about 15 g/ha, about 7-about 12 g/ha, about 5-about 9 g/ha, about 3.5-about 6 g/ha or about 2-about 3 g/ha. In some embodiments, the lambda-cyhalothrin formulations of the current disclosure may be used to control pests of cereals at an active ingredient use rate of about 17-about 26 g/ha, about 14-about 21 g/ha, about 12-about 17 g/ha, about 9-about 14 g/ha, about 7-about 10.5 g/ha, about 5-about 7 g/ha or about 2-about 3.5 g/ha. In some embodiments, the lambda-cyhalothrin formulations of the current disclosure may be used to control pests of cereals at an active ingredient use rate of about 22-about 26 g/ha, about 17-about 21 g/ha, about 15-about 17 g/ha, about 12-about 14 g/ha, about 9-about 10.5 g/ha, about 6-about 7 g/ha or about 3-about 3.5 g/ha.

In some embodiments, the lambda-cyhalothrin formulations of the current disclosure may be used to control pests of cereals at an active ingredient use rate of less than about 13 g/ha, less than about 10.5 g/ha, less than about 9 g/ha, less than about 7 g/ha, less than about 5 g/ha, less than about 3.5 g/ha or less than about 2 g/ha. In some embodiments, the lambda-cyhalothrin formulations of the current disclosure may be used to control pests of cereals at an active ingredient use rate of less than about 17 g/ha, less than about 14 g/ha, less than about 12 g/ha, less than about 9 g/ha, less than about 7 g/ha, less than about 5 g/ha or less than about 2 g/ha. In some embodiments, the lambda-cyhalothrin formulations of the current disclosure may be used to control pests of cereals at an active ingredient use rate of less than about 22 g/ha, less than about 17 g/ha, less than about 15 g/ha, less than about 12 g/ha, less than about 9 g/ha, less than about 6 g/ha or less than about 3 g/ha. In some embodiments, the lambda-cyhalothrin formulations of the current disclosure may be used to control pests of cereals at an active ingredient use rate of less than about 26 g/ha, less than about 21 g/ha, about 17 g/ha, less than about 14 g/ha, less than about 10.5 g/ha, less than about 7 g/ha or less than about 3.5 g/ha.

Non-limiting examples of pests of cereals that can be controlled with lambda-cyhalothrin formulations of the current disclosure include those listed in Table 11, above, and other pests of cereals listed on the labels of currently available lambda-cyhalothrin products.

Lambda-Cyhalothrin—Cereals—Corn

Labeled use rates for the control of various pests of corn by Karate® with Zeon Technology™ and Karate Zeon® 250

CS, two commercially available lambda-cyhalothrin capsule suspensions, are provided in Table 12.

TABLE 12

Active ingredient use rates for the control of pests of corn via foliar application of Karate with Zeon Technology ® and Karate Zeon ® 250 CS.

| Product | Target Pests | Use Rate (g ai/ha) | Re-Application Interval |
|---|---|---|---|
| Karate ® with Zeon Technology ™ | Corn Earworm, Cutworm species, Green Cloverworm, Meadow Spittlebug, Western Bean Cutworm | 17-29 | As required (determined by scouting) or by locally prescribed growth stages; usually 7 or more days |
| control of pests on field corn, seed corn and popcorn | Armyworm, Bean Leaf Beetle, Bird Cherry-Oat Aphid, Cereal Leaf Beetle, Corn Leaf Aphid, English Grain Aphid, European Corn Borer, Fall Armyworm, Flea Beetle species, Grasshopper species, Hop Vine Borer, Japanese Beetle (Adult), Lesser Cornstalk Borer, Mexican Corn Rootworm Beetle (Adult), Northern Corn Rootworm Beetle (Adult), Sap Beetle (Adult), Seedcorn Beetle, Southern Corn Rootworm Beetle (Adult), Southwestern Corn Borer, Stalk Borer, Stink Bug species, Tobacco Budworm, Webworm species, Western Corn Rootworm Beetle (Adult), Yellowstriped Armyworm | 23-35 | As above |
|  | Beet Armyworm, Chinch Bug, Greenbug, Mexican, Rice Borer, Rice Stalk Borer, Southern Corn Leaf Beetle, Sugarcane Borer | 35 | As above |
| Karate Zeon ® 250 CS | Fall Armyworm (*Spodoptera frugiperda*) | 7.5 | |
|  | Black Cutworm (*Agrotis ipsilon*) | 25 | |

In some embodiments, the lambda-cyhalothrin formulations of the current disclosure may be used to control pests of corn at an active ingredient use rate that is lower than the use rate listed on the label of commercially available lambda-cyhalothrin products. In some embodiments, the corn on which the formulations of the current disclosure may be used to control pests is selected from field corn, sweet corn and popcorn (including corn grown for seed). In some embodiments, the formulations of the current disclosure are used to protect corn via application to the soil in which the corn is to be planted prior to seed planting (i.e. as pre-plant incorporated application). In some embodiments, the formulations of the current disclosure may be used to protect corn via application at the time of seed planting (e.g. via an in-furrow or T-banded application), or after planting but prior to emergence of the corn plant (i.e. a pre-emergence application).

In some embodiments, a lambda-cyhalothrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests of corn at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of corn at an active ingredient use rate of about 13-about 22 g/ha, about 10.5-about 17 g/ha, about 9-about 15 g/ha, about 7-about 12 g/ha, about 5-about 9 g/ha, about 3.5-about 6 g/ha or about 2-about 3 g/ha. In some embodiments, the lambda-cyhalothrin formulations of the current disclosure may be used to control pests of corn at an active ingredient use rate of less than about 13-g/ha, less than about 10.5 g/ha, less than about 9 g/ha, less than about 7 g/ha, less than about 5 g/ha, less than about 3.5 g/ha or less than about 2 g/ha. In some embodiments, the lambda-cyhalothrin formulations of the current disclosure may be used to control pests of corn at an active ingredient use rate of about 17-about 26 g/ha, about 14-about 21 g/ha, about 12-about 17 g/ha, about 9-about 14 g/ha, about 7-about 10.5 g/ha, about 5-about 7 g/ha or about 2-about 3.5 g/ha.

In some embodiments, the lambda-cyhalothrin formulations of the current disclosure may be used to control pests of corn at an active ingredient use rate of less than about 17 g/ha, less than about 14 g/ha, less than about 12 g/ha, less than about 9 g/ha, less than about 7 g/ha, less than about 5 g/ha or less than about 2 g/ha. In some embodiments, the lambda-cyhalothrin formulations of the current disclosure may be used to control pests of corn at an active ingredient use rate of less than about 26 g/ha, less than about 21 g/ha, less than about 10.5 g/ha, or less than about 3.5 g/ha.

Non-limiting examples of pests of corn that can be controlled with lambda-cyhalothrin formulations of the current disclosure include those listed in Table 12, above, and other pests of corn listed on the labels of currently available lambda-cyhalothrin products Lambda-Cyhalothrin—Canola Labeled use rates for the control of various pests of canola by Karate® with Zeon Technology™, a commercially available lambda-cyhalothrin capsule suspension, are provided in Table 13.

TABLE 13

Active ingredient use rates for the control of pests of canola with Karate with Zeon Technology ®

| Product | Target Pests | Use Rate (g ai/ha) | Re-Application Interval |
|---|---|---|---|
| Karate ® with Zeon Technology ™ | Armyworm species, Cabbage Seedpod Weevil, Cutworm species, Diamondback Moth, Flea Beetle, Grasshoppers, Looper species, *Lygus* Bug | 17.5-35 | As required (determined by scouting), usually 5 or more days |
| | Cabbage Aphid | 35 | |

In some embodiments, the lambda-cyhalothrin formulations of the current disclosure may be used to control pests of canola at active ingredient use rates that are lower than use rates listed on the labels of commercially available lambda-cyhalothrin pesticides. In some embodiments, a lambda-cyhalothrin formulation of the current disclosure may be used to control pests of canola at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests of canola at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of canola at an active ingredient use rate of about 13-about 26 g/ha, about 10.5-about 21 g/ha, about 9-about 17.5 g/ha, about 7-about 14 g/ha, about 5-about 10.5 g/ha, about 3.5-about 7 g/ha or about 2-about 3.5 g/ha.

In some embodiments, the lambda-cyhalothrin formulations of the current disclosure may be used to control pests of canola at an active ingredient use rate of less than about 13 g/ha, less than about 10. g/ha, less than about 9 g/ha, less than about 7 g/ha, less than about 5 g/ha, less than about 3.5 g/ha or less than about 2 g/ha. In some embodiments, the lambda-cyhalothrin formulations of the current disclosure may be used to control pests of canola at an active ingredient use rate of less than about 26 g/ha, less than about 21 g/ha, less than about 17.5 g/ha, less than about 14 g/ha, less than about 10.5 g/ha, less than about 7 g/ha or less than about 3.5 g/ha.

Non-limiting examples of pests of canola that can be controlled with lambda-cyhalothrin formulations of the current disclosure include those listed in Table 13, above, and other pests of canola listed on the labels of currently available lambda-cyhalothrin products.

Lambda-Cyhalothrin—Potatoes

Labeled use rates for the control of various pests of potatoes by Karate® with Zeon Technology™, a commercially available lambda-cyhalothrin capsule suspension, are provided below.

TABLE 14

Active ingredient use rates for the control of pests of potatoes with Karate with Zeon Technology ®

| Product | Target Pests | Use Rate (g ai/ha) | Re-Application Interval |
|---|---|---|---|
| Karate ® with Zeon Technology ™ | Various pests including Cutworms species, Leafhopper species, Caterpillar species, and Hornworm species | 17.5-35 | As required (determined by scouting), usually 7 or more days |
| | Various pests including Aphid species, Armyworm species, Beetle Species, Earworm species, Cricket species, Borers, Grasshopper species, Looper species, *Lygus* and Plant Bug Species, Potato Psyllids, Tubeworms, Stink Bug Species, Thrips species, Webworm species, Weevil species | 23.3-35 | |
| | Leafminer species, Spider Mite species, Whitefly species | 35 | |

In some embodiments, the lambda-cyhalothrin formulations of the current disclosure may be used to control pests of potatoes at active ingredient use rates that are lower than use rates listed on the labels of commercially available lambda-cyhalothrin pesticides. In some embodiments, a lambda-cyhalothrin formulation of the current disclosure may be used to control pests of potatoes at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests of potatoes at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of potatoes at an active ingredient use rate of about 13-about 26 g/ha, about 10.5-about 21 g/ha, about 9-about 17.5 g/ha, about 7-about 14 g/ha, about 5-about 10.5 g/ha, about 3.5-about 7 g/ha or about 2-about 3.5 g/ha. In some embodiments, the lambda-cyhalothrin formulations of the current disclosure may be used to control pests of potatoes at an active ingredient use rate of about 17.5-about 26 g/ha, about 14-about 21 g/ha, about 12-about 17.5 g/ha, about 9-about 14 g/ha, about 7-about 10.5 g/ha, about 5-about 7 g/ha or about 2-about 3.5 g/ha.

In some embodiments, the lambda-cyhalothrin formulations of the current disclosure may be used to control pests of potatoes at an active ingredient use rate of less than about 13 g/ha, less than about 10.5 g/ha, less than about 9 g/ha, less than about 7 g/ha, less than about 5 g/ha, less than about 3.5 g/ha or less than about 2 g/ha. In some embodiments, the lambda-cyhalothrin formulations of the current disclosure may be used to control pests of potatoes at an active ingredient use rate of less than about 17.5 g/ha, less than about 14 g/ha, less than about 12 g/ha, less than about 9 g/ha, or less than about 2 g/ha. In some embodiments, the lambda-cyhalothrin formulations of the current disclosure may be used to control pests of potatoes at an active ingredient use rate of less than about 26 g/ha, less than about 21 g/ha, or less than about 10.5 g/ha.

Non-limiting examples of pests of potatoes that can be controlled with lambda-cyhalothrin formulations of the current disclosure include those listed in Table 14, above, and other pests of potatoes listed on the labels of currently available lambda-cyhalothrin products Lambda-Cyhalothrin—Turf, Ornamental and Non-Crop Application In some embodiments, the lambda-cyhalothrin formulations of the current disclosure may be used in turf, ornamental and non-crop pest control applications. Examples of such applications include those noted in any portion of the specification, those found on the labels of commercially available lambda-cyhalothrin products and all other turf, ornamental and non-crop applications in which current lambda-cyhalothrin products are used to control pests. Examples of turf, ornamental and non-crop pest control applications in which commercially available lambda-cyhalothrin products such Demand® CS Insecticide are used include but are not limited to the control of pests of turf (e.g., lawn, sod), ornamentals (shrubs, ornamental trees, foliage plants etc.), buildings (indoor and perimeter pest control), and recreational areas such as parks and athletic fields.

In some embodiments, the lambda-cyhalothrin formulations of the current disclosure may be used to control pests in turf, ornamental and non-crop applications at active ingredient use rates that are lower than use rates listed on the labels of commercially available lambda-cyhalothrin pesticides. In some embodiments, a lambda-cyhalothrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests in turf, ornamental and non-crop applications at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

Lambda-Cyhalothrin—Turf, Ornamental and Non-Crop Applications—Lawn and Turfgrass Labeled use rates for the control of various pests of lawn and turfgrass by Demand® CS Insecticide, a commercially available lambda-cyhalothrin capsule suspension, are provided in Table 15.

TABLE 15

Active ingredient use rates for the control of pests of Lawn and Turfgrass with Demand ® CS Insecticide

| Product | Target Pests | Use Rate (g ai/ha) | Re-Application Interval |
|---|---|---|---|
| Demand ® CS Insecticide | Ants (Including Imported fire ants), Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species that transmit Lyme disease) | 29-58 (based on 1 gram of product per ml of product) and 9.7% w/w of active | 7 day intervals if necessary |

TABLE 15-continued

Active ingredient use rates for the control of pests of Lawn and Turfgrass with Demand ® CS Insecticide

| Product | Target Pests | Use Rate (g ai/ha) | Re-Application Interval |
|---------|--------------|--------------------|-----------------------|
|  | Bluegrass billbugs (adult), Black turfgrass *ataenius* (adult), Chiggers, Fleas (adult), Grubs (suppression), weevils (Hyperodes) (adult), Mole crickets (nymphs and young adults) | 58 (based on 1 gram of product per ml of product) and 9.7% w/w of active |  |

In some embodiments, the lambda-cyhalothrin formulations of the current disclosure may be used to control pests of lawn and turfgrass at active ingredient use rates that are lower than use rates listed on the labels of commercially available lambda-cyhalothrin pesticides. In some embodiments, a lambda-cyhalothrin formulation of the current disclosure may be used to control pests of lawn and turfgrass at a use rate that is less than about 75%, less than about 60%, less than about 50%, less than about 40%, less than about 30%, less than about 20% or less than about 10% of a use rate listed on the label of a commercially available lambda-cyhalothrin product.

In some embodiments, a lambda-cyhalothrin formulation of the current disclosure may be used to control pests of lawn and turfgrass at an active ingredient use rate that is lower than the minimum use rate of a range of use rates listed on the label of a commercially available lambda-cyhalothrin product. In some embodiments a lambda-cyhalothrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available lambda-cyhalothrin product.

In some embodiments, the lambda-cyhalothrin formulations of the current disclosure may be used to control pests of lawn and turfgrass at an active ingredient use rate of about 22-about 43 g/ha, about 17-about 35 g/ha, about 14-about 29 g/ha, about 12-about 23 g/ha, about 9-about 17 g/ha, about 6-about 12 g/ha or about 3-about 6 g/ha.

In some embodiments, the lambda-cyhalothrin formulations of the current disclosure may be used to control pests of lawn and turfgrass at an active ingredient use rate of less than about 43 g/ha, less than about 35 g/ha, less than about 29 g/ha, less than about 23 g/ha, less than about 22 g/ha, less than about 17 g/ha, less than about 14 g/ha, less than about 12 g/ha, less than about 9 g/ha, less than about 6 g/ha or less than about 3 g/ha.

Non-limiting examples of pests of pests of lawn and turfgrass that can be controlled with lambda-cyhalothrin formulations of the current disclosure include those listed in Table 15, above, and other pests of pests of lawn and turfgrass listed on the labels of currently available lambda-cyhalothrin products.

Cypermethrin

In various embodiments, the cypermethrin formulations of the current disclosure may be used to control pests at active ingredient use rates that are lower than the use rates listed on the labels of commercially available cypermethrin products. In some embodiments, a cypermethrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available cypermethrin product.

Labels of commercially available cypermethrin products often provide ranges of active ingredient use rates to control pests. In some embodiments, the cypermethrin formulations of the current disclosure may be used to control pests at an active ingredient use rate that is lower than the minimum use rate of a range of use rates listed on the label of a commercially available cypermethrin product. In some embodiments a cypermethrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Cypermethrin—Soybean

Labeled use rates for the control of various pests of soybean by Cipermetrina Nortox 250 EC, a commercially available cypermethrin emulsion concentrate, are provided in Table 16.

TABLE 16

Active ingredient use rates for the control of pests of soybean with Cipermetrina Nortox 250 EC

| Product | Target Pests | Use Rate (g ai/ha) |
|---------|--------------|--------------------|
| Cipermetrina Nortox 250 EC | Green stink bug (*Piezodorus guildini*), Soybean caterpillar, velvetbean caterpillar (*Anticarsia gemmatalis*), Soybean Looper (*Pseudoplusia includens*) | 50 |

In some embodiments, the cypermethrin formulations of the current disclosure may be used to control pests of soybean at active ingredient use rates that are lower than use rates listed on the labels of commercially available cypermethrin pesticides. In some embodiments, a cypermethrin formulation of the current disclosure may be used to control pests of soybean at a use rate that is less than about 75%, less than about 60%, less than about 50%, less than about 40%, less than about 30%, less than about 20% or less than about 10% of a use rate listed on the label of a commercially available cypermethrin product.

In some embodiments, a cypermethrin formulation of the current disclosure may be used to control pests of soybean at an active ingredient use rate that is lower than the minimum use rate of a range of use rates listed on the label of a commercially available cypermethrin product. In some embodiments a cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cypermethrin product.

In some embodiments, the cypermethrin formulations of the current disclosure may be used to control pests of soybean at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

Non-limiting examples of pests of pests of cotton that can be controlled with cypermethrin formulations of the current disclosure include those listed in Table 16, above, and other pests of pests of soybean listed on the labels of currently available cypermethrin products.

Cypermethrin—Cotton

Labeled use rates for the control of various pests of cotton by Cipermetrina Nortox 250 EC and Ammo® 2.5 EC, two commercially available cypermethrin emulsion concentrates, are provided in Table 17.

TABLE 17

Active ingredient use rates for the control of pests of cotton with Cipermetrina Nortox 250 EC

| Product | Target Pests | Use Rate (g ai/ha) | Re-Application Interval |
|---|---|---|---|
| Cipermetrina Nortox 250 EC | Boll Weevil (*Anthonomus grandis*), Tobacco Budworm (*Heliothis virescens*) | 50-62.5 | Boll Weevil: 5 days |
|  | Pink Bollworm (*Pectinophora gossypiella*) | 56.25-62.5 |  |
|  | Leafworm (*Alabama argillacea*) | 10-12.5 |  |
| Ammo ® 2.5 EC Insecticide | Pre-planting, at planting and pre-emergence use: Cutworms | 28-112 |  |
|  | Tobacco Thrips, Cutworms, Soybean (banded) Thrips, | 28-112 |  |
|  | Various pests including Loopers, Corn Borers, Plant Bugs and *Lygus* Bugs, Bollworms, Boll Weevil and others- abbreviated example | 45-112 | Boll Weevil: 3-4 days |
|  | Beet Armyworm | 67-112 |  |

In some embodiments, the cypermethrin formulations of the current disclosure may be used to control pests of cotton at an active ingredient use rate that is lower than the use rate listed on the label of commercially available cypermethrin products. In some embodiments, the formulations of the current disclosure are used to protect cotton via application to the soil in which the cotton is to be planted prior to seed planting (i.e. as pre-plant incorporated application). In some embodiments, the formulations of the current disclosure may be used to protect cotton via application at the time of seed planting (e.g. via an in-furrow or T-banded application), or after planting but prior to emergence of the cotton plant (i.e. a pre-emergence application).

In some embodiments, a cypermethrin formulation of the current disclosure may be used to control pests of cotton at a use rate that is less than about 75%, less than about 60%, less than about 50%, less than about 40%, less than about 30%, less than about 20% or less than about 10% of a use rate listed on the label of a commercially available cypermethrin product.

In some embodiments, a cypermethrin formulation of the current disclosure may be used to control pests of cotton at an active ingredient use rate that is lower than the minimum use rate of a range of use rates listed on the label of a commercially available cypermethrin product. In some embodiments a cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cypermethrin product.

In some embodiments, the cypermethrin formulations of the current disclosure may be used to control pests of cotton at an active ingredient use rate of about 37.5-about 49 g/ha, about 30-about 37.5 g/ha, about 25-about 31 g/ha, about 20-about 25 g/ha, about 15-about 19 g/ha, about 10-about 12.5 g/ha or about 5-about 6 g/ha. In some embodiments, the cypermethrin formulations of the current disclosure may be used to control pests of cotton at an active ingredient use rate of about 7.5-about 9.4 g/ha, about 6-about 7.5 g/ha, about 5-about 6.3 g/ha, about 4-about 5 g/ha, about 3-about 3.8 g/ha, about 2-about 2.5 g/ha or about 1-about 1.3 g/ha. In some embodiments, the cypermethrin formulations of the current disclosure may be used to control pests of cotton at an active ingredient use rate of about 42-about 47 g/ha, about 34-about 37.5 g/ha, about 28-about 31 g/ha, about 22.5-about 25 g/ha, about 17-about 19 g/ha, about 11-about 12.5 g/ha or about 5.6-about 6.3 g/ha. In some embodiments, the cypermethrin formulations of the current disclosure may be used to control pests of cotton at an active ingredient use rate of about 21-about 84 g/ha, about 17-about 67 g/ha, about 14-about 56 g/ha, about 11-about 45 g/ha, about 8-about 34 g/ha, about 6-about 22 g/ha or about 3-about 11 g/ha. In some embodiments, the cypermethrin formulations of the current disclosure may be used to control pests of cotton at an active ingredient use rate of about 50-about 84 g/ha, about 40-about 67 g/ha, about 34-about 56 g/ha, about 27-about 45 g/ha, about 20-about 34 g/ha, about 13-about 22 g/ha or about 7-about 11 g/ha. In some embodiments, the cypermethrin formulations of the current disclosure may be used to control pests of cotton at an active ingredient use rate of about 34-about 84 g/ha, about 27-about 67 g/ha, about 22-about 56 g/ha, about 18-about 45 g/ha, about 13-about 34 g/ha, about 9-about 22 g/ha or about 4-about 11 g/ha.

In some embodiments, the cypermethrin formulations of the current disclosure may be used to control pests of cotton at an active ingredient use rate of less than about 37.5 g/ha, less than about 30 g/ha, less than about 25 g/ha, less than about 20 g/ha, less than about 15 g/ha, less than about 10 g/ha or less than about 5 g/ha. In some embodiments, the cypermethrin formulations of the current disclosure may be used to control pests of cotton at an active ingredient use rate of less than about 7.5 g/ha, less than about 6 g/ha, less than about 4 g/ha, less than about 3 8 g/ha, less than about 2 g/ha or less than about 1 g/ha. In some embodiments, the cypermethrin formulations of the current disclosure may be used to control pests of cotton at an active ingredient use rate of less than about 42 g/ha, less than about 34 g/ha, less than about 28 g/ha, less than about 22.5 g/ha, less than about 17 g/ha, less than about 11 g/ha or less than about 5.6 g/ha. In some embodiments, the cypermethrin formulations of the current disclosure may be used to control pests of cotton at an active ingredient use rate of less than about 21 g/ha, less than about 14 g/ha, less than about 8 g/ha, less than about 6 g/ha or less than about 3 g/ha. In some embodiments, the cypermethrin formulations of the current disclosure may be used to control pests of cotton at an active ingredient use rate of less than about 34 g/ha, less than about 27 g/ha, less than about 22 g/ha, less than about 18 g/ha, less than about 13 g/ha, less than about 9 g/ha or less than about 4 g/ha.

Non-limiting examples of pests of pests of cotton that can be controlled with cypermethrin formulations of the current disclosure include those listed in Table 17, above, and other pests of cotton listed on the labels of currently available cypermethrin products.

Cypermethrin—Rice

Labeled use rates for the control of various pests of rice by Cipermetrina Nortox 250 EC, a commercially available cypermethrin emulsion concentrate, are provided Table 18.

TABLE 18

Active ingredient use rates for the control of pests of rice with Cipermetrina Nortox 250 EC

| Product | Target Pests | Use Rate (g ai/ha) | Re-application Interval |
| --- | --- | --- | --- |
| Cipermetrina Nortox 250 EC | Fall Armyworm (*Spodoptera frugiperda*) | 10-16.25 | Repeat if necessary after 10 day interval |

In some embodiments, the cypermethrin formulations of the current disclosure may be used to control pests of rice at active ingredient use rates that are lower than use rates listed on the labels of commercially available cypermethrin pesticides. In some embodiments, a cypermethrin formulation of the current disclosure may be used to control pests of rice at a use rate that is less than about 75%, less than about 60%, less than about 50%, less than about 40%, less than about 30%, less than about 20% or less than about 10% of a use rate listed on the label of a commercially available cypermethrin product.

In some embodiments, a cypermethrin formulation of the current disclosure may be used to control pests of rice at an active ingredient use rate that is lower than the minimum use rate of a range of use rates listed on the label of a commercially available cypermethrin product. In some embodiments a cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cypermethrin product.

In some embodiments, the cypermethrin formulations of the current disclosure may be used to control pests of rice at an active ingredient use rate of about 11 g/ha, about 9 g/ha, about 7.5 g/ha, about 6 g/ha, about 4.5 g/ha, about 3 g/ha or about 1.5 g/ha.

In some embodiments, the cypermethrin formulations of the current disclosure may be used to control pests of rice at an active ingredient use rate of less than about 11 g/ha, less than about 9 g/ha, less than about 7.5 g/ha, less than about 6 g/ha, less than about 4.5 g/ha, less than about 3 g/ha or less than about 1.5 g/ha.

Non-limiting examples of pests of rice that can be controlled with cypermethrin formulations of the current disclosure include those listed in Table 18, above, and other pests of pests of rice listed on the labels of currently available cypermethrin products.

Cypermethrin—Corn

Labeled use rates for the control of various pests of corn by Cipermetrina Nortox 250 EC, a commercially available cypermethrin emulsion concentrate, are provided Table 19

TABLE 19

Active ingredient use rates for the control of pests of corn with Cipermetrina Nortox 250 EC

| Product | Target Pests | Use Rate (g ai/ha) | Re-application Interval |
| --- | --- | --- | --- |
| Cipermetrina Nortox 250 EC | Fall Armyworm (*Spodoptera frugiperda*) | 10-16.25 | Make no more than one application |

In some embodiments, the cypermethrin formulations of the current disclosure may be used to control pests of corn at active ingredient use rates that are lower than use rates listed on the labels of commercially available cypermethrin pesticides. In some embodiments, a cypermethrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available cypermethrin product.

In some embodiments, a cypermethrin formulation of the current disclosure may be used to control pests of corn at an active ingredient use rate that is lower than the minimum use rate of a range of use rates listed on the label of a commercially available cypermethrin product. In some embodiments a cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cypermethrin product.

In some embodiments, the cypermethrin formulations of the current disclosure may be used to control pests of corn at an active ingredient use rate of about 7.5-about 12 g/ha, about 6-about 10 g/ha, about 5-about 8 g/ha, about 4-about 6.5 g/ha, about 3-about 5 g/ha, about 2-about 3.3 g/ha or about 1-about 1.6 g/ha.

In some embodiments, the cypermethrin formulations of the current disclosure may be used to control pests of corn at an active ingredient use rate of less than about 7.5 g/ha, less than about 6 g/ha, less than about 5 g/ha, less than about 4 g/ha, less than about 3 g/ha, less than about 2 g/ha or less than about 1 g/ha.

Non-limiting examples of pests of corn that can be controlled with cypermethrin formulations of the current disclosure include those listed in Table 19, above, and other pests of corn listed on the labels of currently available cypermethrin products.

Cypermethrin—Turf, Ornamental and Non-Crop Applications

In some embodiments, the cypermethrin formulations of the current disclosure may be used in turf, ornamental and non-crop pest control applications. Examples of turf, ornamental and non-crop pest control applications include those found on the labels of commercially available pyrethroid products and all other turf, ornamental and non-crop applications noted in the Efficacy and Application section or any other part of the specification.

In some embodiments, the cypermethrin formulations of the current disclosure are used to control pests in the applications listed in the label of Cynoff® EC Insecticide, a commercially available cypermethrin product. All of the uses listed on the label of Cynoff® EC Insecticide are considered to be examples of Turf, Ornamental and Non-Crop Applications for the purpose of the current disclosure.

In some embodiments, the cypermethrin formulations of the current disclosure may be used to control pests in turf, ornamental and non-crop applications at active ingredient use rates that are lower than use rates listed on the labels of commercially available cypermethrin pesticides. In some embodiments, a cypermethrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available cypermethrin product.

In some embodiments, a cypermethrin formulation of the current disclosure may be used to control pests in turf, ornamental and non-crop applications at an active ingredient use rate that is lower than the minimum use rate of a range of use rates listed on the label of a commercially available cypermethrin product. In some embodiments a cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cypermethrin product.

Alpha-Cypermethrin

In various embodiments, the alpha-cypermethrin formulations of the current disclosure may be used to control pests at active ingredient use rates that are lower than the use rates listed on the labels of commercially available alpha-cypermethrin products. In some embodiments, an alpha-cypermethrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available alpha-cypermethrin product.

Labels of commercially available alpha-cypermethrin products often provide ranges of active ingredient use rates to control pests. In some embodiments, the alpha-cypermethrin formulations of the current disclosure may be used to control pests at an active ingredient use rate that is lower than the minimum use rate of a range of use rates listed on the label of a commercially available alpha-cypermethrin product. In some embodiments a alpha-cypermethrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Alpha-Cypermethrin—Cereals

In some embodiments, the alpha-cypermethrin formulations of the current disclosure may be used to control pests of cereals at active ingredient use rates that are lower than use rates listed on the labels of commercially available alpha-cypermethrin pesticides. In some embodiments, an alpha-cypermethrin formulation of the current disclosure may be used to control pests of cereals at a use rate that is less than about 75%, less than about 60%, less than about 50%, less than about 40%, less than about 30%, less than about 20% or less than about 10% of a use rate listed on the label of a commercially available alpha-cypermethrin product.

In some embodiments, a alpha-cypermethrin formulation of the current disclosure may be used to control pests of cereals at an active ingredient use rate that is lower than the minimum use rate of a range of use rates listed on the label of a commercially available alpha-cypermethrin product. In some embodiments a alpha-cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available alpha-cypermethrin product.

Alpha-Cypermethrin—Corn

Labeled use rates for the control of various pests of corn by Fastac®100 SC, a commercially alpha-cypermethrin suspension concentrate, are provided in Table 20.

TABLE 20

Active ingredient use rates for the control of pests of corn with by Fastac ® 100 SC

| Product | Target Pests | Use Rate (g ai/ha) | Re-application Interval |
| --- | --- | --- | --- |
| Fastac ® 100 SC | Fall Armyworm (*Spodoptera frugiperda*) | 5 | As necessary |

In some embodiments, the alpha-cypermethrin formulations of the current disclosure may be used to control pests of corn at active ingredient use rates that are lower than use rates listed on the labels of commercially available alpha-cypermethrin pesticides. In some embodiments, an alpha-cypermethrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available alpha-cypermethrin product.

In some embodiments, an alpha-cypermethrin formulation of the current disclosure may be used to control pests of corn at an active ingredient use rate that is lower than the minimum use rate of a range of use rates listed on the label of a commercially available alpha-cypermethrin product. In some embodiments a alpha-cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available alpha-cypermethrin product.

In some embodiments, the cypermethrin formulations of the current disclosure may be used to control pests of corn at an active ingredient use rate of less than about 3.8 g/ha, less than about 3 g/ha, less than about 2.5 g/ha, less than about 2 g/ha, less than about 1.5 g/ha, less than about 1 g/ha or less than about 0.5 g/ha.

Non-limiting examples of pests of corn that can be controlled with cypermethrin formulations of the current disclosure include those listed in Table 20, above, and other pests of corn listed on the labels of currently available cypermethrin products.

Alpha-Cypermethrin—Turf, Ornamental and Non-Crop Applications

In some embodiments, the alpha-cypermethrin formulations of the current disclosure may be used in turf, ornamental and non-crop pest control applications. Examples of turf, ornamental and non-crop pest control applications include those found on the labels of commercially available pyrethroid products and all other turf, ornamental and non-crop applications noted in the Efficacy and Application section or any other portion of the specification.

In some embodiments, the alpha-cypermethrin formulations of the current disclosure may be used to control pests in turf, ornamental and non-crop applications at active ingredient use rates that are lower than use rates listed on the labels of commercially available alpha-cypermethrin pesticides. In some embodiments, an alpha-cypermethrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available alpha-cypermethrin product.

In some embodiments, a alpha-cypermethrin formulation of the current disclosure may be used to control pests in turf, ornamental and non-crop applications at an active ingredient use rate that is lower than the minimum use rate of a range of use rates listed on the label of a commercially available alpha-cypermethrin product. In some embodiments a alpha-cypermethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available alpha-cypermethrin product.

Tefluthrin

In various embodiments, the tefluthrin formulations of the current disclosure may be used to control pests at active ingredient use rates that are lower than the use rates listed on the labels of commercially available tefluthrin products. In some embodiments, an tefluthrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available tefluthrin product.

Labels of commercially available tefluthrin products often provide ranges of active ingredient use rates to control pests. In some embodiments, the tefluthrin formulations of the current disclosure may be used to control pests at an active ingredient use rate that is lower than the minimum use rate of a range of use rates listed on the label of a commercially available tefluthrin product. In some embodiments a tefluthrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Tefluthrin—Corn

In some embodiments, the tefluthrin formulations of the current disclosure may be used to control pests of corn at an active ingredient use rate that is lower than the use rate listed on the label of commercially available bifenthrin products. In some embodiments, the corn on which the formulations of the current disclosure may be used to control pests is selected from field corn, sweet corn and popcorn (including corn grown for seed). In some embodiments, the formulations of the current disclosure are used to protect corn via application to the soil in which the corn is to be planted prior to seed planting (i.e. as pre-plant incorporated application). In some embodiments, the formulations of the current disclosure may be used to protect corn via application at the time of seed planting (e.g. via an in-furrow application or T-banded application), or after planting but prior to emergence of the corn plant (i.e. as a pre-emergence application).

In some embodiments, an tefluthrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available tefluthrin product.

In some embodiments, a tefluthrin formulation of the current disclosure may be used to control pests of corn at an active ingredient use rate that is lower than the minimum use rate of a range of use rates listed on the label of a commercially available tefluthrin product. In some embodiments a tefluthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available tefluthrin product.

Labeled use rates for the control of various pests of corn at planting by Force® CS, a commercially tefluthrin concentrate, are provided in Table 21.

TABLE 21

Active ingredient use rates for the control of pests of corn with Force CS

| Product | Target Pests | Use Rate (g ai/1000 m row crop) |
|---|---|---|
| Force ® CS | Billbug, Chinch Bug, Cutworm, Lesser Cornstalk Borer, Mexican Corn Rootworm, Northern Corn Rootworm, Seedcorn Beetle, Seedcorn Maggot Southern Corn Rootworm, Western Corn, Red Imported Fire Ant, Rootworm, White Grub, Wireworm | 11.2-13.9 |

In some embodiments, the tefluthrin formulations of the current disclosure may be used to control pests of corn at an active ingredient use rate that is lower than the use rate listed on the label of commercially available tefluthrin products. In some embodiments, the formulations of the current disclosure may be used to control pests of corn at a use rate that is about 75%, about 60%, about 50%, about 40%, about 30%, about 20% or about 10% of the use rate listed on commercially available tefluthrin products In some embodiments, the tefluthrin formulations of the current disclosure may be used to control pests of corn at an active ingredient use rate of about 8.4-about 10.4 g/1000 m of corn crop, about 6.7-about 8.3 g/1000 m, about 5.6-about 7.0 g/1000 m, about 4.5-about 5.6 g/1000 m, about 3.4-about 4.2 g/1000 m, about 2.2-about 2.8 g/1000 m or about 1.1-about 1.4 g/1000 m.

In some embodiments, the tefluthrin formulations of the current disclosure may be used to control pests of corn at an active ingredient use rate of less than about 8.4 g/1000 m of corn crop, less than about 6.7 g/1000 m, less than about 5.6 g/1000 m, less than about 5.6 g/1000 m, less than about 3.4 g/1000 m, less than about 2.2 g/1000 m or less than about 1.1 g/1000 m.

Non-limiting examples of pests of corn that can be controlled with tefluthrin formulations of the current disclosure include those listed in Table 21, above, and other pests of corn listed on the labels of currently available tefluthrin products.

Tefluthrin—Turf, Ornamental and Non-Crop Applications

In some embodiments, the tefluthrin formulations of the current disclosure may be used in turf, ornamental and non-crop pest control applications. Examples of turf, ornamental and non-crop pest control applications include those found on the labels of commercially available pyrethroid products and all other turf, ornamental and non-crop applications noted in the Efficacy and Application section or any other portion of the specification.

In some embodiments, the tefluthrin formulations of the current disclosure may be used to control pests in turf, ornamental and non-crop applications at active ingredient use rates that are lower than use rates listed on the labels of commercially available tefluthrin pesticides. In some embodiments, an tefluthrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available tefluthrin product.

In some embodiments, a tefluthrin formulation of the current disclosure may be used to control pests in turf, ornamental and non-crop applications at an active ingredient use rate that is lower than the minimum use rate of a range of use rates listed on the label of a commercially available tefluthrin product. In some embodiments a tefluthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available tefluthrin product.

Cyfluthrin—(Includes all Isomers and Mixtures of Isomers Unless Stated Otherwise)

In various embodiments, the cyfluthrin (including all isomers and mixtures of isomers) formulations of the current disclosure may be used to control pests at active ingredient use rates that are lower than the use rates listed on the labels of commercially available cyfluthrin products. In some embodiments, an cyfluthrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available cyfluthrin product.

Labels of commercially available cyfluthrin products often provide ranges of active ingredient use rates to control pests. In some embodiments, the cyfluthrin formulations of the current disclosure may be used to control pests at an active ingredient use rate that is lower than the minimum use rate of a range of use rates listed on the label of a commercially available cyfluthrin product. In some embodiments a cyfluthrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Cyfluthrin—Corn (β-Cyfluthrin)

Labeled use rates for the control of various pests of corn (field corn, popcorn, seed corn, and teosinte) by foliar application of Baythroid® XL, a commercially available β-cyfluthrin concentrate, are provided in Table 22.

TABLE 22

Active ingredient use rates for the control of pests of corn with Baythroid ® XL

| Product | Target Pests | Use Rate (g ai/ha) |
|---|---|---|
| Baythroid ® XL | Cutworms: Black Cutworm, Granulate Cutworm, Sand Hill Cutworm; Flea beetles | 8-15 |
| | Armyworm (1st and 2nd instar), Bean leaf beetle. Cereal leaf beetle, Chinch bug, Click beetle (adult), Corn earworm, Corn rootworms (adult), European corn borer, Grape colaspis (adult), Japanese beetle (adult), June beetle (adult), Leafhoppers, Masked chafer (adult), Southern armyworm (1st and 2nd instar), Southern corn lea fbeetle, Southwestern corn borer, Stalk borer, Stink bugs, Webworm, Western beancutworm, Yellowstriped armyworm (1st and 2nd instar) | 15-25 |
| | Grasshoppers | 19-25 |
| | Fall armyworm (1st and 2nd instar) | 25 |

In some embodiments, the β-cyfluthrin formulations of the current disclosure may be used to control pests of corn at active ingredient use rates that are lower than use rates listed on the labels of commercially available β-cyfluthrin pesticides. In some embodiments, an β-cyfluthrin formulation of the current disclosure may be used to control pests of corn at a use rate that is less than about 75%, less than about 60%, less than about 50%, less than about 40%, less than about 30%, less than about 20% or less than about 10% of a use rate listed on the label of a commercially available β-cyfluthrin product.

In some embodiments, a β-cyfluthrin formulation of the current disclosure may be used to control pests of corn at an active ingredient use rate that is lower than the minimum use rate of a range of use rates listed on the label of a commercially available β-cyfluthrin product. In some embodiments a β-cyfluthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available β-cyfluthrin product.

In some embodiments, the β-cyfluthrin formulations of the current disclosure may be used to control pests of corn at an active ingredient use rate of about 6-about 11 g/ha, about 5-about 9 g/ha, about 4-about 7 g/ha, about 3-about 6 g/ha, about 2-about 4 g/ha, about 1.6-about 2.9 g/ha or about 0.8-about 1.5 g/ha. In some embodiments, the β-cyfluthrin formulations of the current disclosure may be used to control pests of corn at an active ingredient use rate of about 11-about 18 g/ha, about 9-about 15 g/ha, about 7-about 12 g/ha, about 6-about 10 g/ha, about 4-about 7 g/ha, about 3-about 5 g/ha or about 1.5-about 2.5 g/ha.

In some embodiments, the β-cyfluthrin formulations of the current disclosure may be used to control pests of corn at an active ingredient use rate of less than about 6 g/ha, less than about 5 g/ha, less than about 4 g/ha, less than about 3 g/ha, less than about 2 g/ha, less than about 1.6 g/ha or less than about 0.8 g/ha. In some embodiments, the β-cyfluthrin formulations of the current disclosure may be used to control pests of corn at an active ingredient use rate of less than about 11 g/ha, less than about 9 g/ha, less than about 7 g/ha, less than about 6 g/ha, less than about 4 g/ha, less than about 3 g/ha or less than about 1.5 g/ha. In some embodiments, the β-cyfluthrin formulations of the current disclosure may be used to control pests of corn at an active ingredient use rate of less than about 14 g/ha, less than about 8 g/ha, less than about 5.7 g/ha, less than about 3.8 g/ha or less than about 1.9 g/ha. In some embodiments, the β-cyfluthrin formulations of the current disclosure may be used to control pests of corn at an active ingredient use rate of less than about 18 g/ha, less than about 15 g/ha, less than about 12 g/ha, less than about 10 g/ha, less than about 7 g/ha, less than about 5 g/ha or less than about 2.5 g/ha.

Non-limiting examples of pests of corn that can be controlled with β-cyfluthrin formulations of the current disclosure include those listed in Table 22, above, and other pests of pests of corn listed on the labels of currently available β-cyfluthrin products.

Cyfluthrin—Soybean (β-Cyfluthrin)

Labeled use rates for the control of various pests of soybean by Baythroid® XL, a commercially available 3-cyfluthrin concentrate, are provided Table 23.

TABLE 23

Active ingredient use rates for the control of pests of corn with Baythroid ® XL

| Product | Target Pests | Use Rate (g ai/ha) |
|---|---|---|
| Baythroid ® XL | Bean leaf beetle (growth stage VC-V2), Cutworms, Potato leafhopper, Thrips, Green cloverworm | 8-15 |
| | Armyworm (1st and 2nd instar), Bean leaf beetle, Bean leaf webber, Beet armyworm (1st and 2nd instar), Blister beetle, Cabbage looper, Click beetle (adult), Corn earworm, Corn rootworms (adult), Cucumber beetle, European corn borer, Fall armyworm (1st and 2nd instar), Grape colaspis (adult), Japanese beetle (adult), June beetle (adult), Lygus bug, Masked chafer (adult), Mexican bean beetle, Saltmarsh caterpillar, Silver-spotted skipper, Southern armyworm (1st and 2nd instar), Stink bugs, Tarnished plant bug, Three-cornered alfalfa hopper, Tobacco budworm, Velvetbean caterpillar, | 15-25 |

TABLE 23-continued

Active ingredient use rates for the control of pests of corn with Baythroid ® XL

| Product | Target Pests | Use Rate (g ai/ha) |
|---|---|---|
| | Webworm, Wooly bear caterpillar, Yellowstriped armyworm (1st and 2nd instar) | |
| | Grasshoppers, Soybean aphid | 17-25 |

In some embodiments, the β-cyfluthrin formulations of the current disclosure may be used to control pests of soybean at active ingredient use rates that are lower than use rates listed on the labels of commercially available β-cyfluthrin pesticides. In some embodiments, an β-cyfluthrin formulation of the current disclosure may be used to control pests of soybean at a use rate that is less than about 75%, less than about 60%, less than about 50%, less than about 40%, less than about 30%, less than about 20% or less than about 10% of a use rate listed on the label of a commercially available β-cyfluthrin product.

In some embodiments, a β-cyfluthrin formulation of the current disclosure may be used to control pests of soybean at an active ingredient use rate that is lower than the minimum use rate of a range of use rates listed on the label of a commercially available β-cyfluthrin product. In some embodiments a β-cyfluthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available β-cyfluthrin product.

In some embodiments, the β-cyfluthrin formulations of the current disclosure may be used to control pests of soybean at an active ingredient use rate of about 6-about 11 g/ha, about 5-about 9 g/ha, about 4-about 7 g/ha, about 3-about 6 g/ha, about 2-about 4 g/ha, about 1.6-about 2.9 g/ha or about 0.8-about 1.5 g/ha. In some embodiments, the β-cyfluthrin formulations of the current disclosure may be used to control pests of soybean at an active ingredient use rate of about 11-about 18 g/ha, about 9-about 15 g/ha, about 7-about 12 g/ha, about 6-about 10 g/ha, about 4-about 7 g/ha, about 3-about 5 g/ha or about 1.5-about 2.5 g/ha. In some embodiments, the β-cyfluthrin formulations of the current disclosure may be used to control pests of soybean at an active ingredient use rate of about 13-about 18 g/ha, about 11-about 15 g/ha, about 9-about 12 g/ha, about 7-about 10 g/ha, about 5-about 7 g/ha, about 3.6-about 4.9 g/ha or about 1.8-about 2.5 g/ha.

In some embodiments, the β-cyfluthrin formulations of the current disclosure may be used to control pests of soybean at an active ingredient use rate of less than about 6 g/ha, less than about 5 g/ha, less than about 4 g/ha, less than about 3 g/ha, less than about 2 g/ha, less than about 1.6 g/ha or less than about 0.8 g/ha. In some embodiments, the β-cyfluthrin formulations of the current disclosure may be used to control pests of soybean at an active ingredient use rate of less than about 11 g/ha, less than about 9 g/ha, less than about 7 g/ha, less than about 6 g/ha, less than about 4 g/ha, less than about 3 g/ha or less than about 1.5 g/ha. In some embodiments, the β-cyfluthrin formulations of the current disclosure may be used to control pests of soybean at an active ingredient use rate of less than about 13 g/ha, less than about 11 g/ha, less than about 9 g/ha, less than about 7 10 g/ha, less than about 5 g/ha, less than about 3.6 g/ha or less than about 1.8 g/ha.

Non-limiting examples of pests of soybean that can be controlled with β-cyfluthrin formulations of the current disclosure include those listed in Table 23 above, and other pests of soybean listed on the labels of currently available β-cyfluthrin products.

Cyfluthrin—Turf, Ornamental and Non-Crop Applications

In some embodiments, the cyfluthrin formulations of the current disclosure may be used in turf, ornamental and non-crop pest control applications. Examples of turf, ornamental and non-crop pest control applications include those found on the labels of commercially available pyrethroid products and all other turf, ornamental and non-crop applications noted in the Efficacy and Application section or any other part of the specification.

In some embodiments, the cyfluthrin formulations of the current disclosure are used to control pests in the applications listed in the label of Tempo® SC Ultra, a commercially available β-cyfluthrin product. All of the listed uses in the label of Tempo® SC Ultra are considered to be examples of Turf, Ornamental and Non-Crop Applications for the purpose of the current disclosure.

In some embodiments, the cyfluthrin formulations of the current disclosure may be used to control pests in turf, ornamental and non-crop applications at active ingredient use rates that are lower than use rates listed on the labels of commercially available cyfluthrin pesticides. In some embodiments, a cyfluthrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available cyfluthrin product.

In some embodiments, a cyfluthrin formulation of the current disclosure may be used to control pests in turf, ornamental and non-crop applications at an active ingredient use rate that is lower than the minimum use rate of a range of use rates listed on the label of a commercially available cyfluthrin product. In some embodiments a cyfluthrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available cyfluthrin product.

Deltamethrin

In various embodiments, the deltamethrin formulations of the current disclosure may be used to control pests at active ingredient use rates that are lower than the use rates listed on the labels of commercially available deltamethrin products. In some embodiments, an deltamethrin formulation of the current disclosure may be used to control pests at a use rate that is less than about 75%, less than about 60%, less than about 50%, less than about 40%, less than about 30%, less than about 20% or less than about 10% of a use rate listed on the label of a commercially available deltamethrin product.

Labels of commercially available deltamethrin products often provide ranges of active ingredient use rates to control pests. In some embodiments, the deltamethrin formulations of the current disclosure may be used to control pests at an active ingredient use rate that is lower than the minimum use rate of a range of use rates listed on the label of a commercially available deltamethrin product. In some embodiments a deltamethrin formulation of the current disclosure is used to control pests at a use rate that is less than about 75%, less than about 60%, less than about 50%, less than about 40%, less than about 30%, less than about 20% or less than about 10% of the minimum use rate of a range of use rates listed on the label of a commercially available product.

Deltamethrin—Cereals

In some embodiments, the deltamethrin formulations of the current disclosure may be used to control pests of cereals at active ingredient use rates that are lower than use rates listed on the labels of commercially available deltamethrin pesticides. In some embodiments, an deltamethrin formulation of the current disclosure may be used to control pests of cereals at a use rate that is less than about 75%, less than about 60%, less than about 50%, less than about 40%, less than about 30%, less than about 20% or less than about 10% of a use rate listed on the label of a commercially available deltamethrin product.

In some embodiments, an deltamethrin formulation of the current disclosure may be used to control pests of cereals at an active ingredient use rate that is lower than the minimum use rate of a range of use rates listed on the label of a commercially available deltamethrin product. In some embodiments a deltamethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available deltamethrin product.

Deltamethrin—Cotton

In some embodiments, the deltamethrin formulations of the current disclosure may be used to control pests of cotton at active ingredient use rates that are lower than use rates listed on the labels of commercially available deltamethrin pesticides. In some embodiments, an deltamethrin formulation of the current disclosure may be used to control pests of cotton at a use rate that is less than about 75%, less than about 60%, less than about 50%, less than about 40%, less than about 30%, less than about 20% or less than about 10% of a use rate listed on the label of a commercially available deltamethrin product.

In some embodiments, an deltamethrin formulation of the current disclosure may be used to control pests of cotton at an active ingredient use rate that is lower than the minimum use rate of a range of use rates listed on the label of a commercially available deltamethrin product. In some embodiments a deltamethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available deltamethrin product.

Deltamethrin—Turf, Ornamental and Non-Crop Applications

In some embodiments, the deltamethrin formulations of the current disclosure may be used in turf, ornamental and non-crop pest control applications. Examples of turf, ornamental and non-crop pest control applications include those found on the labels of commercially available pyrethroid products and all other turf, ornamental and non-crop applications noted in the Efficacy and Application section or any other part of the specification.

In some embodiments, the deltamethrin formulations of the current disclosure are used to control pests in the applications listed on the label of Suspend® SC, a commercially deltamethrin product. All of the used listed on the label of Suspend® SC Ultra are considered to be examples of Turf, Ornamental and Non-Crop Applications for the purpose of the current disclosure.

In some embodiments, the deltamethrin formulations of the current disclosure may be used to control pests in turf, ornamental and non-crop applications at active ingredient use rates that are lower than use rates listed on the labels of commercially available deltamethrin pesticides. In some embodiments, a deltamethrin formulation of the current disclosure may be used to control pests in turf, ornamental and non-crop applications at a use rate that is less than about 75%, less than about 60%, less than about 50%, less than about 40%, less than about 30%, less than about 20% or less than about 10% of a use rate listed on the label of a commercially available deltamethrin product.

In some embodiments, a deltamethrin formulation of the current disclosure may be used to control pests in turf, ornamental and non-crop applications at an active ingredient use rate that is lower than the minimum use rate of a range of use rates listed on the label of a commercially available deltamethrin product. In some embodiments a deltamethrin formulation of the current disclosure may be used to control pests at a use rate that is less than about 75%, less than about 60%, less than about 50%, less than about 40%, less than about 30%, less than about 20% or less than about 10% of the minimum use rate of a range of use rates listed on the label of a commercially available deltamethrin product.

EXAMPLES

I: Preparation and Solid Formation of Nanoparticles of Polymer-Associated Active Ingredients Example 1: Preparation of 1 g of Polymer Nanoparticles from poly (methacrylic acid-co-ethyl acrylate) (p(MAA-co-EA))

1 g of polymer nanoparticles derived from p(MAA-co-EA) was made as follows. Briefly, 1 g solid p(MAA-co-EA) (MAA:EA=90:10 or 80:20, MW 450K-800K) was dissolved in 500 mL of deionized water in a 3 L beaker using an overhead stirrer, and pH was maintained at ~7 with 1M NaOH. The solution was stirred overnight to fully dissolve the solid. The next day, 500 mL of 3M NaCl was added to the solution under vigorous stirring. After addition, the solution was left to stir at 500 rpm for another hour. At this stage, the solution viscosity drops indicating the formation of collapsed polymers. The solution was then transferred to a 3 L recrystallization dish equipped with a magnetic stir bar. This solution was exposed to 4-254 nm UV germicidal lamps (G25T8) for 2 hours under constant stirring. After 2 hours, the solution was removed from the UV source and the ions were removed using diafiltration. The resulting retentate was then freeze dried to obtain a powder of the polymer nanoparticles. Alternatively, the retentate could also be spray dried to obtain a powder of the polymer nanoparticles. A particle size of 20-50 nm was measured via dynamic light scattering of a solution of either the collected freeze-dried or spray dried solid re-dispersed in 0.1M NaCl solution, pH adjusted to ~6.8 and stirred overnight.

The polarity of the microenvironment of the nanoparticles was investigated according to the method outlined in *Photochem. Photobiol.* 1982, 35:17. Briefly, 10 uL of a 0.1 mg/mL solution of pyrene in $CH_2Cl_2$ was placed in a 20 ml scintillation vial and the liquid was swirled around to coat the bottom of the vial. The solvent was allowed to evaporate under a fume hood. 10 ml of a 1 mg/mL dispersion of polymer nanoparticles in deionized water (pH adjusted to ~4.5) was added in to the vial with the dried out pyrene solution and was stirred for 48 hours in the dark. Emission spectra were then measured on a Perkin Elmer LS 55 Luminescence Spectrometer using an excitation wavelength of 340 nm, having slit widths for both excitation and emission at 2.5 nm. The emission intensity of the first ($I_1$,~373 nm) and third ($I_3$,~384 nm) vibronic bands were recorded and the ratio ($I_1/I_3$) calculated giving a ratio of ~1.18 indicating that the polymer nanoparticles prepared according to Example 1 has a microenvironment similar to the polarity/hydrophobicity of methanol (see table in *Photochem. Photobiol.* 1982, 35:17 for a complete tabulation of the ratios of $I_1/I_3$ and the corresponding microenvironment polarity.)

The same procedure was used to make polymer nanoparticles from different polyelectrolyte copolymers and polyelectrolyte homopolymers. Examples of other polyelectrolyte copolymers: poly(methacrylic acid (MAA)-co-styrene (S)) (MAA:S=90:10, MW 450K-800K), poly(methacrylic acid (MAA)-co-butylmethacrylate (BUMA)) (MAA:BUMA=75:25, MW 450K-800K).

Example 2: Formation of a Solid Formulation of Nanoparticles or Aggregates of Nanoparticles of Polymer-Associated Lambda Cyhalothrin Via Spray Drying Directly from Common Solvent 5 g of polymer nanoparticles derived from p(MAA-co-EA) were made according the procedure outlined in Example 1. The 5 g of polymer powder was dispersed in 250 mL technical grade methanol in a 500 mL glass beaker until a clear solution was formed, and was then filtered through coarse filter paper to remove any undispersed solids. 5 g of technical grade lambda cyhalothrin (Pacific Agrosciences) was added to the filtered dispersion. The resulting solution was clear, and was stirred at 500 rpm using a magnetic stir bar on a stirrer hot plate for one hour. This solution was then spray dried on a Buchi mini Spray dryer B290 with inlet temperature set at 170° C., aspirator gas flow rate of approximately 35 $m^3/h$, feed rate of approximately 7 mL/min and air flow 601 L/hr. The solid was collected from the collector receptacle of the spray dryer. A volume average dynamic light scattering (DLS) particle size of ~300 nm was measured for the solid re-dispersed either in deionized water or CIPAC D hard water at 400 ppm (solids). DLS particle size was measured using a Malvern Zetasizer ZS.

Example 3: Formation of a Solid Formulation of Nanoparticles or Aggregates of Nanoparticles of Polymer-Associated Cypermethrin Via Spray Drying Directly from Common Solvent 5 g of polymer nanoparticles derived from p(MAA-co-EA) were made according the procedure outlined in Example 1. The 5 g of polymer powder was dispersed in 250 mL technical grade methanol in a 500 mL glass beaker until a clear solution was formed, and was then filtered through coarse filter paper to remove any undispersed solids. 5 g of technical grade cypermethrin (Pacific Agrosciences) was added to the filtered dispersion. The resulting solution was clear, and was stirred at 500 rpm using a magnetic stir bar on a stirrer hot plate for one hour. This solution was then spray dried on a Buchi mini Spray dryer B290 with inlet temperature set at 170° C., aspirator gas flow rate of approximately 35 $m^3/h$, feed rate of approximately 7 mL/min and air flow 601 L/hr. The solid was collected from the collector receptacle of the spray dryer. A volume average DLS particles size of ~400 nm was measured for the solid re-dispersed in either deionized water or CIPAC D hard water at 400 ppm (solids). DLS particle size was measured using a Malvern Zetasizer ZS.

Example 4: Formation of a Solid Formulation of Nanoparticles or Aggregates of Nanoparticles of Polymer-Associated Bifenthrin Via Spray Drying Directly from Common Solvent 5 g of polymer nanoparticles derived from p(MAA-co-EA) were made according the procedure outlined in Example 1. The 5 g of polymer powder was dispersed in 250 mL technical grade methanol in a 500 mL glass beaker until a clear solution was formed, and was then filtered through coarse filter paper to remove any undispersed solids. 5 g of technical grade bifenthrin (Pacific Agrosciences) was added to the filtered dispersion. The resulting solution was clear, and was stirred at 500 rpm using a magnetic stir bar on a stirrer hot plate for one hour. This solution was then spray dried on a Buchi mini Spray dryer B290 with inlet temperature set at 170° C., aspirator gas flow rate of approximately 35 m³/h, feed rate of approximately 7 mL/min and air flow 601 L/hr. The solid was collected from the collector receptacle of the spray dryer. A volume average DLS particles size of ~500 nm was measured for the solid re-dispersed in deionized water at 400 ppm (solids). DLS particle size was measured using a Malvern Zetasizer ZS.

Example 5: Formation of a Solid Formulation of Nanoparticles or Aggregates of Nanoparticles of Polymer-Associated Bifenthrin Via Spray-Drying Directly from a Common Solvent (Second Example)

14.0 g of polymer nanoparticles derived from p(MAA-co-EA) [MAA:EA=90:10 by mass] were made according to the procedure outlined Example 1. The 14.0 g of polymer powder was dispersed in ~100 mL technical grade methanol in a flask equipped with a stir bar. After stirring, the dispersion was centrifuged at 3000 rpm for 30 minutes, and the supernatant was decanted to remove any insoluble fractions. In a separate flask 14.6 g of bifenthrin was dissolved in 600 mL of technical grade methanol. The liquids were combined and stirred at room temperature in the dark overnight. This solution was then spray dried on a Buchi mini Spray dryer B290 with inlet temperature set at 220° C., aspirator gas flow rate of approximately 35 m³/h, feed rate of approximately 7 mL/min and air flow 601 L/hr.

Example 6: Formation of a Solid Formulation of Nanoparticles or Aggregates of Nanoparticles of Polymer-Associated Cypermethrin with 20% Polymer Nanoparticle Content Via Spray Drying Directly from Common Solvent 2 g of polymer nanoparticles derived from p(MAA-co-EA) were made according the procedure outlined in Example 1. The 2 g of polymer powder was dispersed in 250 mL technical grade methanol in a 500 mL glass beaker until a clear solution was formed, and was then filtered through coarse filter paper to remove any undispersed solids. 8 g of technical grade cypermethrin (Pacific Agrosciences) was added to the filtered dispersion. The resulting solution was clear, and was stirred at 500 rpm using a magnetic stir bar on a stirrer hot plate for one hour. This solution was then spray dried on a Buchi mini Spray dryer B290 with inlet temperature set at 170° C., aspirator gas flow rate of approximately 35 m³/h, feed rate of approximately 7 mL/min and air flow 601 L/hr. The solid was collected from the collector receptacle of the spray dryer. A volume average DLS particles size of ~600 nm was measured for the solid re-dispersed in deionized water at 250 ppm (solids). DLS particle size was measured using a Malvern Zetasizer ZS.

Example 7: Formation of a Solid Formulation of Nanoparticles or Aggregates of Nanoparticles of Polymer-Associated Lambda Cyhalothrin from an Aqueous Dispersion 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade lambda cyhalothrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. The methanol solution containing the nanoparticles and lambda cyhalothrin was then slowly dripped into the stirred water at a rate of ~1-2 mL/min using a peristaltic pump. After all the methanol has been added, the resulting milky solution was then left to mix for another 20 minutes. The solution was then concentrated by removing water/solvent using a rotary evaporator to about ½ its initial volume. The concentrated solution was then freeze dried to obtain a solid formulation of lambda cyhalothrin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zetasizer ZS.

Example 8: Formation of a Solid Formulation of Nanoparticles or Aggregates of Nanoparticles of Polymer-Associated Cypermethrin from an Aqueous Dispersion 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. The methanol solution containing the nanoparticles and cypermethrin was then slowly dripped into the stirred water at a rate of ~1-2 mL/min using a peristaltic pump. After all the methanol has been added, the resulting milky solution was then left to mix for another 20 minutes. The solution was then concentrated by removing water/solvent using a rotary evaporator to about ½ its initial volume. The concentrated solution was then freeze dried to obtain a solid formulation of cypermethrin. The solid was fully redispersible in water at a concentration of ˜200 ppm active ingredient. A volume average DLS particles size of ˜500 nm was measured for the solid re-dispersed in deionized water at 400 ppm total solids in the measured dispersion. DLS particle size was measured using a Malvern Zetasizer ZS.

Example 9: Formation of a Solid Formulation of Nanoparticles or Aggregates of Nanoparticles of Polymer-Associated Bifenthrin from an Aqueous Dispersion 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade bifenthrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. The methanol solution containing the nanoparticles and bifenthrin was then slowly dripped into the stirred water at a rate of ~1-2 mL/min using a peristaltic pump. After all the methanol has been added, the resulting milky solution was then left to mix for another 20 minutes. The solution was then concentrated by removing water/solvent using a rotary evaporator to about ½ its initial volume. The concentrated solution was then freeze dried to obtain a solid formulation of bifenthrin. The solid was redispersible in water at a concentration of ~200 ppm active ingredient. A volume average DLS particles size of ~500 nm was measured for the solid re-dispersed in deionized water at 400 ppm total solids in the measured dispersion. DLS particle size was measured using a Malvern Zetasizer ZS.

Figure 2:
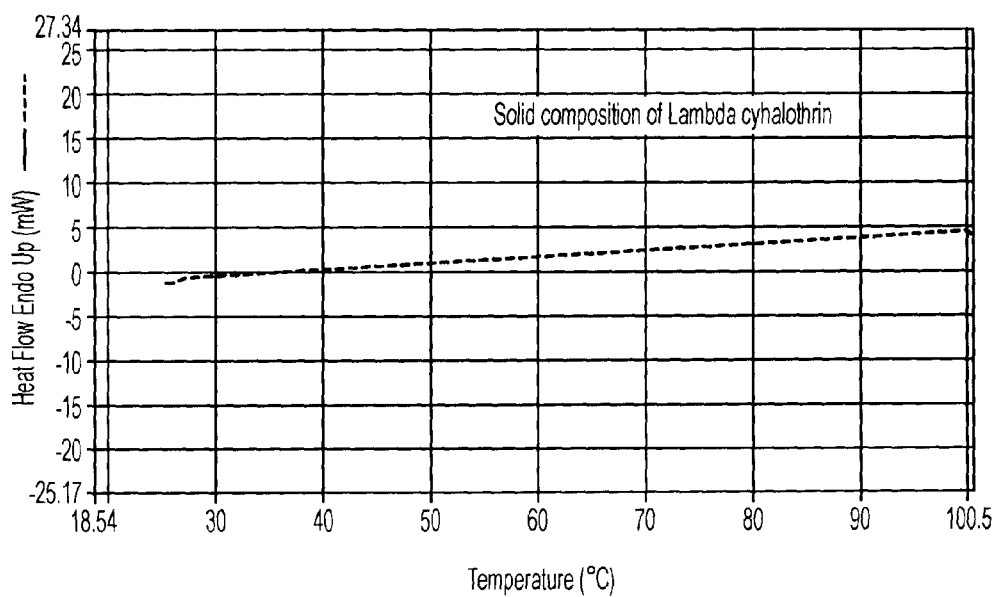

Example 10: Differential Scanning Calorimetry (DSC) Analysis of a Solid Formulation of Nanoparticles or Aggregates of Nanoparticles of Polymer-Associated Lambda Cyhalothrin Thermal analysis (DSC) was done using a Perkin Elmer Diamond Differential Scanning calorimeter under $N_2$ atmosphere. The thermal behavior of 6.05 mg of lambda cyhalothrin was analyzed in an Aluminum sample pan from 25° C. to 100° C. at a temperature ramp rate of 5° C./min. Similarly, the thermal behavior of 5.3 mg of a solid formulation prepared according to Example 7 was analyzed with in an Aluminum pan from 25° C. to 100° C. at a temperature ramp rate of 5° C./min. Heat flow (mW/° C.) for both samples is shown in FIG. 1 and FIG. 2. No melting point is observed for the solid formulation of lambda cyhalothrin prepared according to Example 7 compared to pure unformulated lambda cyhalothrin which has an endothermic (melting) peak at 51° C.

II: Formulations

Example 11: Formation of a High Solids Liquid Suspension (HSLS) Formulation of Lambda-Cyhalothrin from Nanoparticles or Aggregates of Nanoparticles of Polymer-Associated Lambda-Cyhalothrin in a Common Solvent Added into Water 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade lambda cyhalothrin (Pacific Agrosciences) was then added to the filtered dispersion. The resulting solution was clear, and was stirred at 500 rpm using a magnetic stir bar on a stirrer hot plate for one hour. 1 L of deionized water was then placed in a 3 L glass beaker and was stirred at 500 rpm using an overhead mixer. To this 165 mg of Reax88B dispersant was added and 33 mg sodium dodecylbenzene sulfonate was added. The methanol solution containing the nanoparticles and lambda cyhalothrin was then slowly dripped into the water at a rate of ~1-2 mL/min using a peristaltic pump. After all the methanol has been added, the resulting milky solution was then left to mix for another 20 minutes. The solution was then concentrated by removing solvent (both water and methanol) using a rotary evaporator until ~25-30% solids solution was left in the flask (~7-8 mL liquid was left). The mixture was transferred into a 20 mL glass vial. To this, 165 mg of glycerol, 3 mg of xanthan gum (from a 0.1 weight % solution in water) and 1.9 mg 1,2-benzisothiazalin-3-one preservative (Proxel GXL, Arch Chemicals, Inc.) were added. The mixture was mixed well with a stir bar. The HSLS formulation was stable over a period of 2 weeks at 55° C., showing no visible formation of crystallites or caking. If settling occurred, the solution was agitated to restore its initial consistency.

Example 12: Formation of a HSLS Formulation of Cypermethrin from Nanoparticles or Aggregates of Nanoparticles of Polymer-Associated Cypermethrin in a Common Solvent Added into Water 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade cypermethrin (Pacific Agrosciences) was then added to the filtered dispersion. The resulting solution was clear, and was stirred at 500 rpm using a magnetic stir bar on a stirrer hot plate for one hour. 1 L of deionized water was then placed in a 3 L glass beaker and was stirred at 500 rpm using an overhead mixer. To this 165 mg of Reax88B dispersant was added and 33 mg sodium dodecylbenzene sulfonate was added. The methanol solution containing the nanoparticles and cypermethrin was then slowly dripped into the water at a rate of ~1-2 mL/min using a peristaltic pump. After all the methanol has been added, the resulting milky solution was then left to mix for another 20 minutes. The solution was then concentrated by removing solvent (both water and methanol) using a rotary evaporator until a ~30-40% solids solution was left in the flask (~7 mL liquid was left). The mixture was transferred into a 20 mL glass vial. To this, 165 mg of glycerol, 3 mg of xanthan gum (from a 0.1 weight % solution in water) and 1.9 mg 1,2-benzisothiazalin-3-one preservative (Proxel GXL, Arch Chemicals, Inc.) were added. The mixture was mixed well with a stir bar. The HSLS formulation was stable over a period of 2 weeks at 55° C., showing no visible formation of crystallites or caking. If settling occurred, the solution was agitated to restore its initial consistency.

Example 13: Formation of a HSLS Formulation of Bifenthrin from Nanoparticles or Aggregates of Nanoparticles of Polymer-Associated Bifenthrin in a Common Solvent Added into Water 1 g of polymer nanoparticles derived from p(MAA-co-EA) was made according to the procedure outlined in Example 1. The solid was dispersed in 50 mL technical grade methanol in a 250 mL glass beaker until a clear solution was formed, and was then filtered through coarse filter paper to remove any undispersed solids. 1 g of technical grade bifenthrin (Pacific Agrosciences) was then added to the filtered dispersion. The resulting solution was clear, and was stirred at 500 rpm using a magnetic stir bar on a stirrer hot plate for one hour. 1 L of deionized water was then placed in a 3 L glass beaker and was stirred at 500 rpm using an overhead mixer. To this 165 mg of Reax88B dispersant, and 33 mg sodium dodecylbenzene sulfonate was added. The methanol solution containing the nanoparticles and bifenthrin was then slowly dripped into the water at a rate of ~1-2 mL/min using a peristaltic pump. After all the methanol has been added, the resulting milky solution was then left to mix for another 20 minutes. The solution was then concentrated by removing solvent (both water and methanol) using a rotary evaporator until a ~30-40% solids solution was left in the flask (~7 mL liquid was left). The mixture was transferred into a 20 mL glass vial. To this, 165 mg of glycerol, 3 mg of xanthan gum (from a 0.1 weight % solution in water) and 1.9 mg 1,2-benzisothiazalin-3-one preservative (Proxel GXL, Arch Chemicals, Inc.) were added. The mixture was mixed well with a stir bar. The HSLS formulation was stable over a period of 2 weeks at 55° C., showing no visible formation of crystallites or caking. If settling occurred, the solution was agitated to restore its initial consistency.

Example 14: Formation of a HSLS Formulation of Lambda Cyhalothrin from a Solid Formulation of Nanoparticles or Aggregates of Nanoparticles of Polymer-Associated Lambda Cyhalothrin 2 g of a solid formulation of lambda cyhalothrin was prepared according to the procedure outlined in Example 2. In a 20 mL vial, this solid was then dispersed in 7 mL water containing: 165 mg of Reax88B dispersant; 33 mg sodium dodecylbenzene sulfonate; 165 mg of glycerol, 3 mg of xanthan gum (from a 0.1 weight % solution in water) and 1.9 mg 1,2-benzisothiazalin-3-one preservative (Proxel GXL, Arch Chemicals, Inc.). The solution was mixed well with a stir bar. The HSLS formulation was stable over a period of 2 weeks at 55° C., showing no visible formation of crystallites or caking. If settling occurred, the solution was agitated to restore its initial consistency.

Example 15: Formation of a HSLS Formulation of Cypermethrin from a Solid Formulation of Nanoparticles or Aggregates of Nanoparticles of Polymer-Associated Cypermethrin 2 g of a solid formulation of cypermethrin was prepared according to the procedure outlined in Example 3. In a 20 mL vial, this solid was then dispersed in 7 mL water containing: 165 mg of Reax88B dispersant; 33 mg sodium dodecylbenzene sulfonate; 165 mg of glycerol, 3 mg of xanthan gum (from a 0.1 weight % solution in water) and 1.9 mg 1,2-benzisothiazalin-3-one preservative (Proxel GXL, Arch Chemicals, Inc.). The solution was mixed well with a stir bar. The HSLS formulation was stable over a period of 2 weeks at 55° C., showing no visible formation of crystallites or caking. If settling occurred, the solution was agitated to restore its initial consistency.

Example 16: Formation of a HSLS Formulation of Bifenthrin from a Solid Formulation of Nanoparticles or Aggregates of Nanoparticles of Polymer-Associated Bifenthrin (First Example)

3.2 g of a solid formulation of bifenthrin was prepared according to the procedure outlined in Example 5 and transferred to a 20 mL test tube. 6 mL of water, 0.16 mg of Gerapon T-77 (wetter) and 0.16 g of Gerapon TA/72 (dispersant) were added to the tube, and the suspension was allowed to sit at room temperature overnight. 0.64 g propylene glycol (antifreeze), 0.64 g Antifoam FG-10 (defoamer, Arch Chemicals, Inc.), 0.4 g Proxel BD-20 (Biocide) and 3.75 mL of water were then added to the tube. The suspension was then mixed with an overhead stirrer at 200 rpm for approximately 3.5 h, then 500 rpm for approximately 3 h, then 2200 rpm for a total of 4 h

Example 17: Formation of a HSLS Formulation of Bifenthrin from a Solid Formulation of Nanoparticles or Aggregates of Nanoparticles of Polymer-Associated Bifenthrin (Second Example)

2 g of a solid formulation of bifenthrin was prepared according to the procedure outlined in Example 4. In a 20 mL vial, this solid was then dispersed in 7 mL water containing: 165 mg of Reax88B dispersant; 33 mg sodium dodecylbenzene sulfonate; 165 mg of glycerol, 3 mg of xanthan gum (from a 0.1 weight % solution in water) and 1.9 mg 1,2-benzisothiazalin-3-one preservative (Proxel GXL, Arch Chemicals, Inc.). The solution was mixed well with a stir bar. The HSLS formulation was stable over a period of 2 weeks at 55° C., showing no visible formation of crystallites or caking. If settling occurred, the solution was agitated to restore its initial consistency.

Example 18: Formation of a Wettable Granule (WG) Formulation from a Solid Formulation of Nanoparticles or Aggregates of Nanoparticles of Polymer-Associated Lambda-Cyhalothrin 20 g of a solid formulation of lambda-cyhalothrin was prepared according to the procedure outlined in Example 2. In a beaker, 17.6 g of lactose, 2 g of Reax88B, and 400 mg of sodium dodecylbenzene sulfonate were added along with 10-12 g of water. The mixture was stirred very well and heated slightly (~60° C.) to fully disperse all the solids. Once the solids had been dispersed, the resulting solution was allowed to cool to room temperature. The solid formulation of lambda cyhalothrin was then immediately added to the cooled water solution containing the filler, dispersant and wetter. The resulting slurry was mixed very well with a spatula until the mixture had a dough-like consistency. The dough-like mixture was then extruded into 15 cm strips though the orifice of a 5 mL disposable hypodermic syringe. The strips were allowed to dry for 1 hour and were then cut into small 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 19: Formation of a Wettable Granule (WG) Formulation from a Solid Formulation of Nanoparticles or Aggregates of Nanoparticles of Polymer-Associated Cypermethrin 20 g of a solid formulation of cypermethrin was prepared according to the procedure outlined in Example 3. In a beaker, 17.6 g of lactose, 2 g of Reax88B, and 400 mg of sodium dodecylbenzene sulfonate were added along with 10-12 g of water. The mixture was stirred very well and heated slightly (~60° C.) to fully disperse all the solids. Once the solids had been dispersed, the resulting solution was allowed to cool to room temperature. The solid formulation of cypermethrin was then immediately added to the cooled water solution containing the filler, dispersant and wetter. The resulting slurry was mixed very well with a spatula until the mixture had a dough-like consistency. The dough-like mixture was then extruded into 15 cm strips though the orifice of a 5 mL disposable hypodermic syringe. The strips were allowed to dry for 1 hour and were then cut into small 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 20: Formation of a Wettable Granule (WG) Formulation from a Solid Formulation of Nanoparticles or Aggregates of Nanoparticles of Polymer-Associated Bifenthrin 20 g of a solid formulation of bifenthrin was prepared according to the procedure outlined in Example 4. In a beaker, 17.6 g of lactose, 2 g of Reax88B, and 400 mg of sodium dodecylbenzene sulfonate were added along with 10-12 g of water. The mixture was stirred very well and heated slightly (~60° C.) to fully disperse all the solids. Once the solids had been dispersed, the resulting solution was allowed to cool to room temperature. The solid formulation of bifenthrin was then immediately added to the cooled water solution containing the filler, dispersant and wetter. The resulting slurry was mixed very well with a spatula until the mixture had a dough-like consistency. The dough-like mixture was then extruded into 15 cm strips though the orifice of a 5 mL disposable hypodermic syringe. The strips were allowed to dry for 1 hour and were then cut into small 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 21: Formation of WG Formulation from a Liquid Dispersion of Nanoparticles or Aggregates of Nanoparticles of Polymer-Associated Lambda-Cyhalothrin 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade lambda-cyhalothrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer, and to this 17.6 g of lactose, 2 g of Reax88B, and 400 mg of sodium dodecylbenzene sulfonate were added. The methanol solution containing the polymer nanoparticles and lambda-cyhalothrin was then slowly dripped into the water at a rate of ~5-10 mL/min using a peristaltic pump. After all the methanol solution had been added, the resulting milky solution was left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. To this solid, about 10-12 g of water was slowly added under constant mixing until the resulting mixture had a dough-like consistency. The dough-like mixture was then extruded into 15 cm strips though the orifice of a 5 mL disposable hypodermic syringe. The extruded strips were allowed to dry for 1 hour and were then cut into 2-5 mm granules. The WG formulation had minimal dustiness, was stable to several freeze thaw cycles (~5° C. to 30° C.), and had a dispersed particle size of 300 nm at 200 ppm active concentration. No phase separation of the active ingredient occurred after several temperature cycles between 25° C. and 54° C.

Example 22 Formation of WG Formulation from a Liquid Dispersion of Nanoparticles or Aggregates of Nanoparticles of Polymer-Associated Cypermethrin 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this, 17.6 g of lactose, 2 g of Reax88B, and 400 mg of sodium dodecylbenzene sulfonate were added. The methanol solution containing the polymer nanoparticles and cypermethrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. To this solid, about 10-12 g of water was slowly added under constant mixing until the resulting mixture had a dough-like consistency. The dough-like mixture was then extruded into 15 cm strips though the orifice of a 5 mL disposable hypodermic syringe. The extruded strips were allowed to dry for 1 hour and were then cut into 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 23: Formation of WG Formulation from a Liquid Dispersion of Nanoparticles or Aggregates of Nanoparticles of Polymer-Associated Bifenthrin 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade bifenthrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this 17.6 g of lactose, 2 g of Reax88B, and 400 mg of sodium dodecylbenzene sulfonate were added. The methanol solution containing the polymer nanoparticles and bifenthrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. To this solid, about 10-12 g of water was slowly added under constant mixing until the resulting mixture had a dough-like consistency. The dough-like mixture was then extruded into 15 cm strips though the orifice of a 5 mL disposable hypodermic syringe. The extruded strips were allowed to dry for 1 hour and were then cut into 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 24: Formation of WG Formulation from an Aqueous Dispersion of Nanoparticles or Aggregates of Nanoparticles of Polymer-Associated Cypermethrin with Lower Polymer Content 5 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 15 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this 17.6 g of lactose, 2 g of Reax88B, and 400 mg of sodium dodecylbenzene sulfonate were added. The methanol solution containing the polymer nanoparticles and cypermethrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. To this solid, about 10-12 g of water was slowly added under constant mixing until the resulting mixture had a dough-like consistency. The dough-like mixture was then extruded into 15 cm strips though the orifice of a 5 mL disposable hypodermic syringe. The extruded strips were allowed to dry for 1 hour and were then cut into 2-5 mm granules. The WG formulation had minimal dustiness, was stable to several freeze thaw cycles (−5° C. to 30° C.), and had a dispersed particle size of 300 nm at 200 ppm active concentration. No phase separation of the active ingredient occurred after several temperature cycles between 25° C. and 54° C.

Example 25: Formation of a Quick Dissolving WG Formulation from an Aqueous Dispersion of Nanoparticles or Aggregates of Nanoparticles of Polymer-Associated Cypermethrin Using Ammonium Carbonate as a Pore Forming Agent 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this, 17.6 g of lactose, 2 g of Reax88B, and 400 mg of sodium dodecylbenzene sulfonate were added. The methanol solution containing the polymer nanoparticles and cypermethrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. In a separate beaker, 4 g of $(NH_4)_2CO_3$ was mixed with 10 mL deionized water. This solution was then slowly added to the freeze dried powder under constant mixing until the resulting mixture had a dough-like consistency. The dough-like mixture was then extruded into 15 cm strips though the orifice of a 5 mL disposable hypodermic syringe. The extruded strips were allowed to dry for 10 minutes and were then cut into 2-5 mm granules. The cut granules were heated on a Teflon pan to ~100° C. to allow the deformulation of the $(NH_4)_2CO_3$. Heating was stopped when the granules were roughly double in size. The cooled formulation had minimal dustiness, was stable to several freeze thaw cycles (−5° C. to 30° C.), and had a dispersed particle size of 300 nm at 200 ppm active concentration with native solution pH at 8.0. Granules dispersed in the solution in less than 40 seconds. No phase separation of the active ingredient occurred after the granules were subjected to several temperature cycles between 25° C. and 54° C.

Example 26: Formation of a Quick Dissolving WG Formulation from an Aqueous Dispersion of Nanoparticles or Aggregates of Nanoparticles of Polymer-Associated Cypermethrin Using Ammonium Oxalate and Ammonium Hydrogen Carbonate as Pore Forming Agents 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this, 17.6 g of lactose, 2 g of Reax88B, and 400 mg of sodium dodecylbenzene sulfonate were added. The methanol solution containing the polymer nanoparticles and cypermethrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. 40 g of the freeze-dried powder was then placed in a beaker. In a separate beaker, 0.689 g of $(NH_4)HCO3$ and 0.680 g of $(NH_4)_2C_2O_4$ was mixed with 10 mL deionized water. This solution was then slowly added to the freeze dried powder under constant mixing until the resulting mixture had a dough-like consistency. The dough-like mixture was then extruded into 15 cm strips though the orifice of a 5 mL disposable hypodermic syringe. The extruded strips were allowed to dry for 10 minutes and were then cut into 2-5 mm granules. The cut granules were heated on a Teflon pan to ~130° C. to allow the deformulation of the $(NH_4)_2CO_3$ and $(NH_4)_2C_2O_4$. Heating was stopped when the granules were roughly double in size (about 20 minutes). The cooled formulation had minimal dustiness, was stable to several freeze thaw cycles (−5° C. to 30° C.), and had a dispersed particle size of 300 nm at 200 ppm active concentration with native solution pH at 5.6. The granules dispersed in solution in less than 30 seconds. No phase separation of the active ingredient occurred after the granules were subjected to several temperature cycles between 25° C. and 54° C.

Example 27 Formation of a WP Formulation of Lambda-Cyhalothrin from a Solid Formulation of Nanoparticles or Aggregates of Nanoparticles of Polymer-Associated Lambda-Cyhalothrin [Nanoparticles Derived from p(MAA-co-EA); 1:1 Ratio of Lambda-Cyhalothrin:Nanoparticles]

1.70 g of a solid formulation of nanoparticles or aggregates of nanoparticles of polymer-associated lambda-cyhalothrin were prepared via spray drying according to Example 2 (nanoparticles derived from poly(MAA-co-EA), MAA:EA=90:10). 100 mg of Geropon TA-72 and 100 mg of Geropon T-77 were added to a vial and ground together. All of these components were then added to a vial along with 300 mg of Aerosil 380 (fumed silica), which was sealed, secured on a vortex, and shaken for approximately 20-30 minutes. The vortexed sample was sieved through a No. 18 mesh (1 mm) openings, and any residual clumps were gently broken-up with a mortar and pestle. The WP was stable to storage at 45° C. for two weeks and to temperature cycling (between −10° C. and 45° C.), being redispersible in water after both of these tests.

Example 28: Formation of a Quick Dissolving Wettable Powder (WP) Formulation from a Solid Formulation of Nanoparticles or Aggregates of Nanoparticles of Polymer-Associated Cypermethrin Encased in a Water Soluble Bag A solid formulation of cypermethrin was prepared by the following method. 10 g of polymer nanoparticles derived from p(MAA-co-EA) was made according to the procedure outlined in Example 1. The solid was dispersed in 250 mL technical grade methanol in a 500 mL glass beaker until a clear solution was formed, and was then filtered through coarse filter paper to remove any undispersed solids. 10 g of technical grade cypermethrin (Pacific Agrosciences) was then added to the filtered dispersion. The resulting solution was clear, and was stirred at 500 rpm using a magnetic stir bar on a stirrer hot plate for one hour. 2 L of deionized water was then placed in a 3 L glass beaker and was stirred at 500 rpm using an overhead mixer. To this, 17.6 g of lactose, 2 g of Reax88B, and 400 mg of sodium dodecylbenzene sulfonate were added. The methanol solution containing the polymer nanoparticles and cypermethrin was then slowly dripped into the water at a rate of ~5-10 mL/min using a peristaltic pump. After all the methanol solution had been added, the resulting milky solution was then left to mix for another 20 minutes. The solution was then concentrated by removing solvent (both water and methanol) using a rotary evaporator until ~30-40% of the original volume was left. The concentrated mixture was freeze dried to obtain a dry powder. About 25 mg of the powder was placed inside a 1"×1" polyvinyl alcohol (PVA) pouch (~125 mg) made using PVA sheets from Monosol (copolymer of vinyl alcohol/vinyl acetate, 88% hydrolyzed). The pouch was sealed with an iron set to medium temperature. The pouch was dispersed in 25 mL of tap water using a stir bar obtaining a dispersion of the formulation of cypermethrin in <1 min.

Example 29 Formation of a HSLS Formulation of Nanoparticles or Aggregates of Nanoparticles of Polymer-Associated Alpha-Cypermethrin by Ball-Milling Pre-Formed Nanoparticles and Active Ingredient Nanoparticles Prior to Milling with Formulating Agents [Nanoparticles Derived from p(MAA-co-EA); 4:1 Ratio of Alpha-Cypermethrin:Nanoparticles]

A HSLS formulation containing 20% alpha-cypermethrin by mass was prepared according to the following procedure. To an 80 mL stainless steel milling jar (EQ-MJ-3-80SS, MTI Corporation, Richmond Calif., USA) were added 100 g of stainless steel balls (2 mm diameter), 5.4 g of technical grade alpha-cypermethrin and 1.3 g polymer nanoparticles derived from poly(MAA-co-EA) [MAA:EA=75:25 by mass, prepared according to Example 1]. The jar was sealed and milled on a desk top high speed vibrating ball mill (MSK-SFM-3, MTI Corporation, Richmond Calif., USA) for 5 minutes, then cooled in an ice bath for 5 min. 0.750 g of Morwet D-425 (wetter, sodium salt of naphthalene sulfonate condensate), 0.250 g Rhodasurf BC720 (dispersant, ethoxylated tridecyl alcohol), 0.250 g Aerosil® 380 (fumed silica), 1.565 g of propylene glycol (anti-freeze), 0.250 g Trans10-A (Trans-Chemo, Inc., anti-foam agent, 10% Silicone antifoam; water-based; Ag-grade), 0.0658 g Proxel BD-20 (biocide, Industrial Microbiostat, 19.3% active biocide ingredient, Arch Chemicals Inc.) and 14.47 mL of RO water (de-ionized via reverse osmosis) were then added to the jar. The jar was sealed and milled for 5 minutes, then cooled in an ice bath for 5 minutes. Prior to milling for a third time, the jar was opened and 0.500 g of Xanthan gum solution (5% aqueous Xanthan gum prepared form Kelzan® M, CP Kelco U.S., Inc.) and 0.250 g Trans10-A (Trans-Chemo, Inc., anti-foam agent, 10% Silicone antifoam; water-based; Ag-grade) were added. The jar was re-sealed and then milled for another 5 minutes. After milling, the jar was cooled in an ice bath for 5 minutes and was then allowed to reach ambient temperature.

Example 30: Formation of a HSLS Formulation of Nanoparticles or Aggregates of Nanoparticles of Polymer-Associated Bifenthrin by Ball Milling in the Presence of Formulating Agents [Nanoparticles Derived from p(MAA-co-EA); 5:1 Ratio of Bifenthrin:Nanoparticles]

A HSLS formulation containing ~25% bifenthrin by mass was prepared according to the following procedure. The following were added to an 80 mL stainless steel milling jar (EQ-MJ-3-80SS, MTI Corporation, Richmond Calif., USA): 100 g of stainless steel balls (2 mm diameter), 6.4 g of technical grade Bifenthrin, 1.27 g polymer nanoparticles derived from poly(MAA-co-EA) [MAA:EA=75:25 by mass, prepared according to Example 1], 1.0 g of Morwet D-425 (wetter, sodium salt of naphthalene sulfonate condensate), 0.25 g Rhodasurf BC720 (dispersant, ethoxylated tridecyl alcohol), 0.250 g Aerosil 380 (fumed silica), 1.439 g of propylene glycol (anti-freeze), 0.250 g Trans10-A (Trans-Chemo, Inc., anti-foam agent, 10% Silicone antifoam; water-based; Ag-grade), 0.0658 g Proxel BD-20 (biocide, Industrial Microbiostat, 19.3% active biocide ingredient, Arch Chemicals Inc.), 0.25 g Xanthan gum solution (5% aqueous Xanthan gum prepared from Kelzan® M, CP Kelco U.S., Inc.), and 13.35 mL of RO (Reverse-osmosis purified) water. The jar was then sealed and milled on a desk top high speed vibrating ball mill (MSK-SFM-3, MTI Corporation, Richmond Calif., USA) for 5 minutes. The jar was then cooled in an ice bath for 5 minutes, milled for an additional 5 minutes, then cooled in an ice bath for an additional 5 minutes. Prior to milling for a third time, the jar was opened and 0.25 g Xanthan gum solution (5% aqueous Xanthan gum, prepared as above) and 0.250 g Trans10-A (anti-foam, as above) were added. The jar was then, re-sealed and milled for another 5 minutes. After milling, the jar was cooled in an ice bath for 5 minutes and was then allowed to reach ambient temperature. No separation of the aqueous and suspended phase was observed over a period of 1 week.

Example 31 Formation of a HSLS Formulation of Nanoparticles or Aggregates of Nanoparticles of Polymer-Associated Bifenthrin by Ball Milling in the Presence of Formulating Agents [Nanoparticles Derived from p(MAA-co-EA); 5:1 Ratio of Bifenthrin:Nanoparticles]

A HSLS formulation containing ~20% bifenthrin by mass was prepared according to the following procedure. To an 80 mL stainless steel milling jar (EQ-MJ-3-8055, MTI Corporation, Richmond Calif., USA) were added 44 g of stainless steel balls (½"-¼" diameter), 6.26 g of technical grade Bifenthrin, 1.2 g of polymer nanoparticles derived from poly(MAA-co-EA) [MAA:EA=90:10 by mass, prepared according to Example 1], 0.9 g of Geropon T-77, 1.5 g of Geropon TA/72, 0.150 g Aerosil 380 (fumed silica), 2.03 g of propylene glycol (anti-freeze), 3.00 g Trans10-A (Trans-Chemo, Inc., anti-foam agent, 10% Silicone antifoam; water-based; Ag-grade), 0.0789 g Proxel BD-20 (biocide, Industrial Microbiostat, 19.3% active biocide ingredient, Arch Chemicals Inc.), 1.2 g Xanthan gum solution (5% aqueous Xanthan gum prepared from Kelzan® M, CP Kelco U.S., Inc.), and 13.68 g of RO (Reverse-osmosis purified) water. The jar was then sealed and milled on a desk top high speed vibrating ball mill (MSK-SFM-3, MTI Corporation, Richmond Calif., USA) for 6 minutes, the cooled on an ice bath for approximately 10 minutes. Three additional milling & cooling cycles were performed as described for a total of 4 cycle. The isolated HSLS had a viscosity of 50 cps and a DLS particle size of ~500 nm at 200 ppm active concentration in CIPAC D water. The HSLS was stable, showing no separation or caking after being subjected to temperature cycling (between −10° C. and 45° C.).

Example 32 Formation of a HSLS Formulation of Nanoparticles or Aggregates of Nanoparticles of Polymer-Associated Bifenthrin by Ball Milling in the Presence of Formulating Agents [Nanoparticles Derived from p(MAA-co-EA); 5:1 Ratio of Bifenthrin:Nanoparticles]

A HSLS formulation containing ~20% bifenthrin by mass was prepared according to the following procedure. To an 80 mL stainless steel milling jar (EQ-MJ-3-8055, MTI Corporation, Richmond Calif., USA) were added 44 g of stainless steel balls (½"-¼" diameter), 6.26 g of technical grade Bifenthrin, 1.2 g of polymer nanoparticles derived from poly(MAA-co-EA) [MAA:EA=75:25 by mass, prepared according to Example 1], 0.9 g of Geropon T-77, 1.5 g of Geropon TA/72, 0.150 g Aerosil 380 (fumed silica), 2.03 g of propylene glycol (anti-freeze), 3.00 g Trans10-A (Trans-Chemo, Inc., anti-foam agent, 10% Silicone antifoam; water-based; Ag-grade), 0.0789 g Proxel BD-20 (biocide, Industrial Microbiostat, 19.3% active biocide ingredient, Arch Chemicals Inc.), 0.66 g Xanthan gum solution (5% aqueous Xanthan gum prepared from Kelzan® M, CP Kelco U.S., Inc.), and 14.277 g of RO (reverse osmosis purified) water. The jar was then sealed and milled on a desk top high speed vibrating ball mill (MSK-SFM-3, MTI Corporation, Richmond Calif., USA) for 6 minutes, then cooled on an ice bath for approximately 10 minutes. Three additional milling/cooling cycles were performed as described (total 4 cycles). The isolated HSLS had a viscosity of 50 cps and a DLS particle size of ~500 nm at 200 ppm active concentration in CIPAC D water. The HSLS was stable, showing no separation or caking after being subjected to temperature cycling (between −10° C. and 45° C.).

Example 33: Formation of a HSLS Formulation of Nanoparticles or Aggregates of Nanoparticles of Polymer-Associated Bifenthrin by Ball Milling in the Presence of Formulating Agents [Nanoparticles Derived from p(MAA-co-S); 3.5:1 Ratio of Bifenthrin:Nanoparticles]

A HSLS formulation containing 18% bifenthrin by mass was prepared by according to the following procedure. To a 100 mL glass beaker immersed in an ice water bath were added 8.35 g technical grade bifenthrin, 2.41 g polymer nanoparticles derived from poly(MAA-co-S) (MAA:S=75:25 by mass, prepared according to Example 1), 0.44 g Geropon T77 (wetter), 2.2 g Geropon TA/72 (dispersant), 2.95 g propylene glycol (anti-freeze), 0.18 g Trans10-A (Trans-Chemo, Inc., anti-foam agent, 10% Silicone anti-foam; water-based; Ag-grade), 0.12 g Proxel BD-20 (biocide, Industrial Microbiostat, 19.3% active biocide ingredient, Arch Chemicals Inc.), and 27.98 g RO (Reverse-osmosis purified) water. The mixture was stirred (in an ice water bath) for 3 hours. After stirring, the mixture was placed in a stainless steel milling jar (EQ-MJ-3-8055, MTI Corporation, Richmond Calif., USA) along with 54 g of stainless steel balls (½"-¼" diameter). The jar was then sealed and cooled in an ice bath for 10 minutes and then milled on a desk top high speed vibrating ball mill (MSK-SFM-3, MTI Corporation, Richmond Calif., USA) for 6 minutes. After milling, the jar was cooled in an ice bath for 5 minutes and milled for an additional 6 minutes. The cooling/milling cycle was repeated for a third time. After the final (third) milling step, the jar was cooled in an ice bath for 5 minutes and was then allowed to reach ambient temperature. The isolated HSLS had a viscosity of 50 cps and a DLS particle size of ~380 nm at 200 ppm active ingredient concentration in CIPAC D water. The HSLS was stable showing no separation or caking after being subjected to temperature cycling (between −10° C. and 45° C.) and 2 week storage at both 54° C. and 45° C.

Example 34: Formation of a HSLS Formulation of Nanoparticles or Aggregates of Nanoparticles of Polymer-Associated Bifenthrin by Ball Milling in the Presence of Formulating Agents [Nanoparticles Derived from p(MAA-co-BUMA); 3:1 Ratio of Bifenthrin:Nanoparticles]

A HSLS formulation containing ~21% bifenthrin by mass was prepared by according to the following procedure. To a 100 mL glass beaker immersed in an ice water bath were added 6.5 g technical grade bifenthrin; 2.21 g polymer nanoparticles derived from poly(MAA-co-BUMA) (MAA:BUMA=75:25 by mass, prepared according to Example 1), 0.9 g Geropon T77 (wetter); 0.9 g Geropon TA/72 (dispersant), 2.01 g propylene glycol (anti-freeze, 10% solution), 0.12 g Trans10-A (Trans-Chemo, Inc., anti-foam agent, 10% Silicone antifoam; water-based; Ag-grade), 0.078 g Proxel BD-20 (biocide, Industrial Microbiostat, 19.3% active biocide ingredient, Arch Chemicals Inc.), 0.6 mL (~0.6 g) Xanthan gum solution (5% aqueous Xanthan gum prepared from Kelzan® M, CP Kelco U.S., Inc.), and 15.74 g RO (reverse osmosis purified) water. The mixture was stirred (in an ice water bath) for 3 hours. After stirring, the mixture was placed in a stainless steel milling jar (EQ-MJ-3-8055, MTI Corporation, Richmond Calif., USA) along with 54 g of stainless steel balls (½"-¼" diameter). The jar was then sealed and cooled in an ice bath for 10 minutes and then milled on a desk top high speed vibrating ball mill (MSK-SFM-3, MTI Corporation, Richmond Calif., USA) for 6 minutes. After milling, the jar was cooled in an ice bath for 5 minutes and milled for an additional 6 minutes. The cooling/milling cycle was repeated for a third time. After the final (third) milling step, the jar was cooled in an ice bath for 5 minutes and was then allowed to reach ambient temperature. The isolated HSLS had a viscosity of 50 cps and a DLS particle size of ~380 nm at 200 ppm active ingredient concentration in CIPAC D water. The HSLS was stable showing no separation or caking after being subjected to temperature cycling (between −10° C. and 45° C.) and 2 week storage at both 54° C. and 45° C.

Example 35: Formation of a HSLS Formulation of Nanoparticles or Aggregates of Nanoparticles of Polymer-Associated Alpha-Cypermethrin by Ball Milling in the Presence of Formulating Agents Nanoparticles Derived from p(MAA-co-EA); 5:1 Ratio of Alpha-Cypermethrin:Nanoparticles A HSLS formulation containing ~25% alpha-cypermethrin by mass was prepared according to the following procedure. To an 80 mL stainless steel milling jar (EQ-MJ-3-8055, MTI Corporation, Richmond Calif., USA) were added 100 g of stainless steel balls (2 mm diameter), 6.72 g of technical grade alpha-cypermethrin, 1.27 g polymer nanoparticles derived from poly(MAA-co-EA) [MAA:EA=75:25 by mass, prepared according to Example 1], 1.0 g Morwet D-425 (wetter, sodium salt of naphthalene sulfonate condensate), 0.25 g Rhodasurf BC720 (dispersant, ethoxylated tridecyl alcohol), 0.250 g Aerosil® 380 (fumed silica), 1.44 g of propylene glycol (anti-freeze), 0.250 g Trans10-A (Trans-Chemo, Inc., anti-foam agent, 10% Silicone antifoam; water-based; Ag-grade), 0.0658 g Proxel BD-20 (biocide, Industrial Microbiostat, 19.3% active biocide ingredient, Arch Chemicals Inc.), and 13.01 mL of RO water. The jar was then sealed and milled on a desk top high speed vibrating ball mill (MSK-SFM-3, MTI Corporation, Richmond Calif., USA) for 5 minutes. The jar was then cooled in an ice bath for 5 minutes, milled for an additional 5 minutes, then cooled in an ice bath for an additional 5 minutes. Prior to milling for a third time, the jar was opened and 0.500 g of Xanthan gum (5% aqueous Xanthan gum prepared form Kelzan® M, CP Kelco U.S., Inc.) and 0.250 g Trans10-A were added. The jar was then re-sealed and milled for another 5 minutes. After milling, the jar was cooled in an ice bath for 5 minutes and was then allowed to reach ambient temperature. The isolated HSLS had a viscosity of 51 cps and a DLS Z-ave. particle size of ~719 nm at 200 ppm active concentration in CIPAC D water. The HSLS was stable, showing no separation or caking after being subjected to temperature cycling (between −10° C. and 45° C.). No separation of the aqueous and suspended phase was observed at room temperature over a period of 1 week.

Example 36: Preparation of a HSLS Formulation of Nanoparticles or Aggregates of Nanoparticles of Polymer-Associated Alpha-Cypermethrin Via Ball Milling. [Nanoparticles Derived from p(MAA-co-S); 4:1 Ratio of Alpha-Cypermethrin:Nanoparticles]

A HSLS formulation containing ~20% alpha-cypermethrin by mass was prepared according to the following procedure. An 80 mL stainless steel milling jar (EQ-MJ-3-80SS, MTI Corporation, Richmond Calif., USA) was filed with stainless steel balls (2 mm). 7.993 g of technical grade alpha-cypermethrin and 2.036 g of polymer nanoparticles derived from poly(MAA-co-S) [MAA:S=75:25 by mass, prepared according to Example 1] were added to the jar. The jar was sealed and milled on a desk top high speed vibrating ball mill (MSK-SFM-3, MTI Corporation, Richmond Calif., USA) for 20 minutes, then cooled on an ice bath for 10 minutes. The jar was opened and 1.00 g of Morwet D-425 (surfactant/wetter, sodium salt of naphthalene sulfonate condensate), 1.0 g Proxel BD-20 (biocide, Industrial Microbiostat, 19.3% active biocide ingredient, Arch Chemicals Inc.), 0.80 g Trans10-A (Trans-Chemo, Inc., anti-foam agent, 10% Silicone antifoam; water-based; Ag-grade), 0.406 g of Aerosil 380 (fumed silica), 2.398 g propylene glycol (antifreeze) and 20.00 g of RO (reverse osmosis purified) water were added. The jar was sealed and rotated (not milled) on a roller for 1 hour. After rotation the jar was opened and 0.4004 g of Rhodasurf BC420 (wetter) was added. The jar was sealed, rotated on a roller for 1 hour, milled for 10 minutes, and then cooled in an ice bath for 10 minutes. 4.0 g of Xanthan gum solution (1% aqueous Xanthan gum prepared from Kelzan® M, CP Kelco U.S., Inc.) was then added to the milling jar and incorporated into the mixture via rotation of the jar on a roller for 1 hour to give the final concentrate. DLS Z-average particle size of formulation dispersed in CIPAC D at 200 ppm alpha-cypermethrin: 864 nm.

Example 37 Preparation of a HSLS Formulation of Nanoparticles or Aggregates of Nanoparticles of Polymer-Associated Alpha-Cypermethrin Via Ball Milling. [Nanoparticles Derived from p(MAA-co-BUMA); 4:1 Ratio of Alpha-Cypermethrin:Nanoparticles]

A HSLS formulation containing 20% alpha-cypermethrin by mass was prepared according to the following procedure. An 80 mL stainless steel milling jar (EQ-MJ-3-8055, MTI Corporation, Richmond Calif., USA) was filed with stainless steel balls (2 mm). 8.00 g of technical grade alpha-cypermethrin and 2.01 g of polymer nanoparticles derived from poly(MAA-co-BUMA) [MAA:BUMA=75:25 by mass, prepared according to Example 1] were added to the jar. The jar was sealed and milled on a desk top high speed vibrating ball mill (MSK-SFM-3, MTI Corporation, Richmond Calif., USA) for 20 minutes, then cooled on an ice bath for 5 minutes. The jar was opened and 1.00 g of Morwet D-425 (surfactant/wetter, sodium salt of naphthalene sulfonate condensate), 1.0 Proxel BD-20 (biocide, Industrial Microbiostat, 19.3% active biocide ingredient, Arch Chemicals Inc.), 0.796 g Trans10-A (Trans-Chemo, Inc., anti-foam agent, 10% Silicone antifoam; water-based; Ag-grade), 0.406 g of Aerosil 380 (fumed silica), 2.40 g propylene glycol (antifreeze) and 20.00 g of RO (reverse osmosis purified) water were added. The jar was sealed and rotated (not milled) on a roller for 1 hour. After rotation the jar was opened and 0.4004 g of Rhodasurf BC420 (wetter) was added. The jar was sealed, rotated on a roller for 1 hour, milled for 10 minutes, and then cooled in an ice bath for 10 minutes. 4.0 g of Xanthan gum solution (1% aqueous Xanthan gum prepared from Kelzan® M, CP Kelco U.S., Inc.) was then added to the milling jar and incorporated into the mixture via rotation of the jar on a roller for 1 hour to give the final concentrate. DLS Z-average particle size of formulation dispersed in CIPAC D at 200 ppm alpha-cypermethrin: 656 nm.

III: Formulation Testing

Example 38: Oral Toxicity Bioassay of a Formulation of Lambda Cyhalothrin Prepared According to Example 7

The toxicity of a formulation of lambda cyhalothrin prepared according to Example 7 was compared to a commercially available lambda cyhalothrin emulsion concentrate (EC) formulation (MATADOR 120EC). Briefly, 4 cm leaf disks were cut from leaves of organically grown cabbage plants and were inoculated with a solution containing varying concentrations of the formulation prepared according to Example 7. The inoculating solution was prepared by first dispersing a known amount of the formulation (to make 0.5-1000 ppm solutions of active ingredient) in half the amount of required water. Once the formulation had been totally dispersed, the solution was diluted to its final volume with 1% non-ionic surfactant (NIS) solution (Tween 20, Sigma). Final NIS concentration in the inoculating solution was 0.5% by weight. Each leaf disk was dipped in the inoculating solution for approximately 20 seconds and was placed in a Pall 45 mm×9 mm tight fitting lid Petri dish. A 40 mm filter paper disk moistened with 0.1 ml of distilled water was placed in the bottom of each replicate to aid in plant tissue preservation. Ten (10) cabbage loopers, 2nd instar, were placed in each dish, 2 dishes equal one replicate. Replicates were placed in a research laboratory. Environmental conditions averaged 69 F-75 F with 12-hours of light daily. Evaluations were made 48-hours following infestation for dead cabbage loopers (reported as % mortality). Table 4 below summarizes the effect of the formulation of lambda cyhalothrin on cabbage loopers. The formulation of lambda cyhalothrin prepared according to Example 7 showed comparable performance to the commercial formulation even without the addition of any formulants such as dispersants, wetters, fillers, etc. at the use rate of lambda cyhalothrin (100-200 ppm), but showed lower performance at lower use rates (<1 ppm).

TABLE 24

Average percent mortality of cabbage looper (*Trichoplusia ni*) larvae (2nd instar) 48 hours after exposure to cabbage leaves dipped in a solution of NIS + solid formulation prepared according to Example 7, or commercially formulated (MATADOR 120EC) at various concentrations.

| Treatment | Concentration | n | Average Corrected Percent Mortality |
|---|---|---|---|
| MATADOR 120EC | 0.5 ppm | 35 | 100[a]* |
|  | 1 ppm | 35 | 91.4 ± 8.57[ab] |
|  | 5 ppm | 35 | 100[a] |
|  | 10 ppm | 25 | 100[a] |
|  | 100 ppm | 25 | 100[a] |
|  | 1000 ppm | 25 | 100a |
| Lambda cyhalothrin formulation according to Example 7 | 0.5 ppm | 40 | 47.5 ± 13.0[c] |
|  | 1 ppm | 40 | 82.5 ± 12.78[ab] |
|  | 5 ppm | 40 | 100[a] |
|  | 10 ppm | 30 | 100[a] |
|  | 100 ppm | 30 | 100[a] |
|  | 1000 ppm | 30 | 100[a] |

*Within and between columns followed by the same letter are not significantly different at $\alpha = 0.05$.

Example 39: Oral Toxicity Bioassay of Formulations of Bifenthrin Prepared According to the Current Disclosure (48 Hour Mortality Assays of Bifenthrin Formulations)

The efficacy of bifenthrin formulations prepared according to the present disclosure were compared to commercial formulations in 48 hour looper mortality assays. Each formulation was prepared to the indicated concentration in 0.5 wt % NIS (Induce) at a concentration of 0.1, 0.5 or 1 ppm active ingredient. The assay was performed according to the procedure outlined in Example 38 and the results are given in table 6, below. As can be seen, the bifenthrin formulations of the present disclosure demonstrated comparable or enhanced performance compared to the commercial formulations.

TABLE 25

Results of oral toxicity bioassay of formulations of bifenthrin prepared according to the current disclosure (*commercial control (Brigade ® 2EC) mortality in parentheses)

| Formulation Example, type of formulation, ratio bifenthrin: nanoparticles, nanoparticle composition (mass fraction of monomers given in [brackets]) | % mortality* | | |
|---|---|---|---|
| | 0.1 ppm | 0.5 ppm | 1 ppm |
| Example 5 solid powder formulation (WP), 1:1 spray dried powder, p(MAA[90]-co-EA[10]) | 0 (0) | 53 (40) | 80 (80) |
| Example 33, HSLS, 3.5:1, p(MAA[75]-co-S[25])) | 0 (0) | 67 (25) | 63 (67) |
| Example 34, HSLS, 3:1, p(MAA[75]-co-BUMA[25])) | 0 (0) | 48 (25) | 88 (67) |
| Example 16, HSLS, 1:1 HSLS, p(MAA[90]-co-EA[10]) | 4 (0) | 45 (25) | 92 (67) |
| Example 32, HSLS, 5:1, p(MAA[75]-co-EA[25]) | 0 (0) | 58 (25) | 67 (67) |
| Example 31 HSLS, 5:1, p(MAA[90]-co-EA[10]) | 0 (0) | 64 (25) | 67 (67) |

*commercial control (Brigade ® 2EC) mortality in parenthesis

Example 40: Field-to-Lab Method to Evaluate Residual Activity of WG Formulations of Nanoparticles or Aggregates of Nanoparticles of Polymer-Associated Lambda Cyhalothrin The residual activity of a WG formulation of nanoparticles or aggregates of nanoparticles of polymer associated lambda cyhalothrin was compared against a commercial formulation (KARATE WITH ZEON). Field plots were prepared by tilling the soil 4 to 6 inches in depth. Lettuce plugs, 4" height, purchased from a local nursery were transplanted into plots that were arranged in a randomized complete block design spaced 30 inches apart. Three replicates consisting of 2 plants per replicate (with each replicate located in a different area of the block), were inoculated with a WG formulation of nanoparticles or aggregates of nanoparticles of polymer-associated lambda cyhalothrin as described in Example 21. To prepare the inoculation solution, a known amount of WG (weighed out to obtain 18 g lambda cyhalothrin/hectare) was first fully dispersed in half the amount of the required water, by mixing for at least 4 minutes, and then diluted to the final desired concentration with 1% non-ionic surfactant (NIS) solution (Induce, Helena Chemical Company). Final concentration of the NIS in solution was 0.5%. Each replicate was individually caged immediately in a wire tomato cage 30 inches in height, 12 inches in diameter covered with anti-virus insect screening. The inoculating solution was applied by using a 3-nozzle surround boom at a 15 GPA spray volume. In cases where the spray containing the WG formulation came into contact with the farmer, the formulation could be easily washed off without showing any signs of skin irritation. All plants were allowed to acclimatize for 7 days before inoculation. Similarly, three replicates were inoculated with the commercial lambda cyhalothrin formulation using the same active ingredient concentrations and NIS as was used for the WG. Three replicates were used as a control where no inoculation was done.

Seven (7) and fourteen (14) days following inoculation, two (2) 4 cm leaf disks were cut from leaves that were exposed to the WG formulation, the commercial formulation and the control. One disk was taken from each plant in a replicate. Each leaf disk was placed in a Pall 45 mm×9 mm tight fitting lid Petri dish. A 40 mm filter paper disk moistened with 0.1 ml of distilled water was placed in the bottom of each replicate to aid in plant tissue preservation. Ten (10) cabbage loopers, 2nd instar, were placed in each dish, 2 dishes equal one replicate. Replicates were placed in research laboratory. Environmental conditions averaged high temperature 75 F to low temperature of 69 F with 12-hours of light daily. Evaluations were made 48-hours following infestation for live, knockdown and dead cabbage loopers.

Table 26 below gives a summary of the results for the field to lab residual activity.

TABLE 26

Summary of residual activity for WG formulation on lettuce plants

| Treatment Type | % Mortality (7 Days After Application) | % Mortality (14 Days After Application) |
|---|---|---|
| WG formulation | 90 | 76 |
| KARATE WITH ZEON | 50 | 42 |

Example 41: Field-to-Lab Method to Assess Upward Foliar Mobility of a WG Formulation of Nanoparticles or Aggregates of Nanoparticles of Polymer-Associated Lambda Cyhalothrin The foliar upward mobility activity of a WG formulation of nanoparticles or aggregates of nanoparticles of polymer associated lambda cyhalothrin was compared against a commercial formulation (Karate w/Zeon). Field plots were prepared by tilling the soil 4 to 6 inches in depth. Lettuce plugs, 4" height, purchased from a local nursery were transplanted into plots that were arranged in a randomized complete block design spaced 30 inches apart. Three replicates consisting of 2 plants per replicate (with each replicate located in a different area of the block), were inoculated with a WG formulation of nanoparticles or aggregates of nanoparticles of polymer-associated lambda cyhalothrin as described in Example 21. During inoculation, the growing point of each plant was protected from spray with a 4 cm tall by 3.5 cm diameter plastic cup. To prepare the inoculation solution, a known amount of WG (weighed out to obtain 18 g lambda cyhalothrin/hectare) was first fully dispersed in half the amount of the required water, by mixing for at least 4 minutes, and then diluted to the final desired concentration with 1% non-ionic surfactant (NIS) solution (Induce, Helena Chemical Company). Final concentration of the NIS in solution was 0.5%. Each replicate was individually caged immediately in a wire tomato cage 30 inches in height, 12 inches in diameter covered with anti-virus insect screening. The inoculating solution was applied by using a 3-nozzle surround boom at a 15 GPA spray volume. In cases where the spray containing the WG formulation came into contact with the farmer, the formulation could be easily washed off without showing any signs of skin irritation. All plants were allowed to acclimatize for 6 days before inoculation. Similarly, three replicates were inoculated with the commercial lambda cyhalothrin formulation using the same active ingredient concentrations and NIS as was used for the WG. Three replicates were used as a control where no inoculation was done.

Ten (10) days following inoculation, two (2) 4 cm leaf disks were cut from the newly expanded & protected foliage of replicates that were exposed to the WG formulation, the commercial formulation and the control. One disk was taken from each plant in a replicate. Each leaf disk was placed in a Pall 45 mm×9 mm tight fitting lid Petri dish. A 40 mm filter paper disk moistened with 0.1 ml of distilled water was placed in the bottom of each replicate to aid in plant tissue preservation. Ten (10) cabbage loopers, 2nd instar, were placed in each dish, 2 dishes equal one replicate. Replicates were placed in research laboratory. Environmental conditions averaged 69 F-75 F with 12-hours of light daily. Evaluations were made 48-hours following infestation for live, knockdown and dead cabbage loopers.

Table 27 gives a summary of the foliar mobility of the WG formulation.

TABLE 27

Foliar mobility of the WG formulation compared to a commercial formulation

| Treatment Type | % Mortality In New Growth |
|---|---|
| WG formulation | 61.7 |
| KARATE WITH ZEON | 28.3 |
| Untreated control | 1.7 |

Example 42: UV Stability of Formulations of Nanoparticles or Aggregates of Nanoparticles of Polymer Associated Lambda Cyhalothrin The stability of a WG formulation of nanoparticles or aggregates of nanoparticles of polymer associated lambda cyhalothrin was compared to a commercial formulation containing a UV-blocker (MATADOR 120 EC). A WG formulation of lambda cyhalothrin was prepared according to Example 21. The granules were dispersed in water to produce a solution that was 2 mg/mL in lambda cyhalothrin. Similarly, the commercial formulation was diluted with water to obtain a solution that was 2 mg/mL in lambda cyhalothrin. A solution containing surfactant and technical grade lambda cyhalothrin was also prepared at the same active ingredient concentration (2 mg/mL). A thin film of each solution was then cast on a microscope slide, and was exposed to a solar simulator (Fade Test UV simulator, model 16S-300-003; Solar Light Co, Glenside, Pa. USA) for different periods of time (5 mins-240 mins). The amount of non-photo degraded lambda cyhalothrin was assayed by extracting the active from the thin film after exposure and then using thin layer chromatography (TLC) to determine the extent of photo degradation.

Table 28 summarizes the UV stability of these lambda cyhalothrin formulations.

TABLE 28

UV Stability of lambda cyhalothrin formulations

| Formulation | Time to total degradation |
|---|---|
| Lambda cyhalothrin alone | 5-8 minutes |
| MATADOR 120EC (commercial formulation with UV-blocker) | 120-130 minutes |
| WG formulation containing nanoparticles of polymer associated lambda cyhalothrin | 210-240 minutes |

The following two formulations (Example 43 and Example 44) were prepared for the UV-stability tests of Example 45.

Example 43: Formation of a HSLS Formulation of Lambda-Cyhalothrin and Benzophenone from Solid Formulations of Nanoparticles or Aggregates of Nanoparticles of Polymer-Associated Lambda-Cyhalothrin and Benzophenone for UV Stability Tests [Nanoparticles Derived from p(MAA-co-EA); 1:1 and 1:2 Ratio of Lambda-Cyhalothrin:Nanoparticles]

A HSLS formulation of lambda-cyhalothrin and benzophenone was prepared from two solid formulations of lambda-cyhalothrin and a solid formulation benzophenone (prepared according to the spray drying procedure outlined in Example 2). The first solid "1:1 solid" was prepared by mixing 3 g of technical grade lambda-cyhalothrin and 3 g polymer nanoparticles (derived from poly(MAA-co-EA), MAA:EA=90:10, prepared according to Example 1) with 200 mL MeOH followed by spray drying. The second solid "1:2 solid" was prepared by mixing 1.5 g of technical grade lambda-cyhalothrin and 3 g of polymer nanoparticles (particles same as 1:1 solid) with 200 mL MeOH followed by spray drying. Similarly, a solid formulation of benzophenone "benzophenone-polymer nanoparticle solid" was prepared by mixing 160 mg of benzophenone and 1 g polymer nanoparticles (particles the same as the 1:1 solid, above) was mixed with 200 mL MeOH and spray dried. A HSLS formulation was prepared by adding to a 20 mL scintillation vial with a tuning fork stirrer: 1.2 g of the "1:1 solid"; 1.8 g of the "1:2 solid", 100 mg Geropon T-77 (wetter), 200 mg Geropon TA172 (dispersant), 500 mg propylene glycol (anti-freeze), 400 mg Dow Corning FG-10 (anti-foam agent), 250 mg Proxel BD-20 (biocide, Industrial Microbiostat, 19.3% active biocide ingredient, Arch Chemicals Inc.), 42 mg benzophenone-polymer nanoparticle solid and 5.41 g of RO (reverse osmosis purified) water. The mixture was stirred overnight at 1500 rpm. The HSLS was stable under cycling (between −10° C. and 45° C.) and gave a DLS particle size of 1000 nm at 200 ppm active concentration in CIPAC D water.

Example 44: Formation of a WP Formulation of Lambda-Cyhalothrin and Benzophenone from Solid Formulations of Nanoparticles or Aggregates of Nanoparticles of Polymer-Associated Lambda-Cyhalothrin and Benzophenone for UV Stability Tests [Nanoparticles Derived from p(MAA-co-EA); 1:2 Ratio of Lambda-Cyhalothrin:Nanoparticles]

A WP formulation of lambda-cyhalothrin and benzophenone was prepared from a solid formulation of lambda-cyhalothrin and a solid formulation of benzophenone (prepared according to the spray drying procedure outlined in Example 2). The solid formulation of lambda-cyhalothrin was prepared by mixing 5 g of technical grade lambda-cyhalothrin and 10 g polymer nanoparticles (derived from poly(MAA-co-EA), MAA:EA=90:10, prepared according to Example 1) with 200 mL MeOH followed by spray drying. Similarly, a solid formulation of benzophenone "benzophenone-polymer nanoparticle solid" was prepared by mixing 160 mg of benzophenone and 1 g polymer nanoparticles (particles the same as those of the lambda-cyhalothrin solid, above) was mixed with 200 mL MeOH and spray dried. To make the WP, the following were mixed together using a mortar and pestle: 7.5 g 1:2 solid; 1.9 g polymer nanoparticles (derived from poly(MAA-co-EA), MAA:EA=90:10, prepared according to Example 1), 0.0225 g benzophenone-polymer nanoparticle solid; 0.1 g sodium dodecyl benzyl sulfonate; 0.5 g Reax88B. The obtained solid mixture was stable under cycling (between −10° C. and 45° C.) and gave a DLS particle size of 1000 nm at 200 ppm active concentration in CIPAC D water.

Example 45: Comparative UV Stability of HSLS and WP Lambda-Cyhalothrin Formulations of the Present Disclosure and Commercially Lambda-Cyhalothrin Available Formulations The UV stability of a HSLS and WP formulation of lambda cyhalothrin formulations of the present disclosure (prepared according to Example 43 and Example 44, respectively) were compared with the commercial products Matador® and Warrior®.

The WP and HSLS lambda-cyhalothrin formulations described above, along with 2 commercial formulations (Matador and Warrior II) were tested for their UV stability using a fade test UV simulator (Model 16S-300-003, Solar Light Co., Inc, Glenside, Pa., USA) with spot size 1.8 cm and the sample distance of 16 cm from the light source. Light intensity (UVA and UVB) was 100 $mW/cm^2$. Briefly, each sample was dispersed at 200 ppm active concentration in RO (reverse osmosis purified) water. 1.5 cm×3 cm glass strips were cut from microscope cover slips (VWR) and were used as substrates for the UV exposure tests. For each sample and exposure time point tested, a 504 spot of the test solution was placed on one end of the slide and was allowed to dry. After the sample was dried, another 504 of the test solution was placed on the dried spot. This was repeated 2 more times to give a total of 2004 of test solution deposited on the spot. The spot was then exposed to the UV simulator for the time of interest (e.g. 1 hour or 2 hours). After exposure, the spotted glass slide was sonicated in a vial of acetonitrile to extract the remaining active. The acetonitrile wash was analyzed for active content using HPLC. The percentage of active degraded was then calculated. All of the UV stability tests were performed in duplicate. The results of the UV stability tests are summarized in the table below. As can be seen, the formulations of the present disclosure demonstrate comparable or enhanced stability compared to the commercial formulations.

TABLE 29

Comparative UV Stability of HSLS and WP lambda-cyhalothrin formulations of the present disclosure and commercially available formulations UV stability (% active degraded)

| Sample | 1 hour exposure | 2 hours exposure |
|---|---|---|
| Matador | 17.6 | 35.3 |
| Warrior II | 25.0 | 47.2 |
| HSLS of lambda-Cyhalothrin (From Example 43) | 9.4 | 36.5 |
| WP of lambda-Cyhalothrin (From Example 44) | 17.8 | 23.3 |

Example 46: Lab Scale Trial to Demonstrate Efficacy of a WG Formulation of Nanoparticles or Aggregates of Nanoparticles of Polymer-Associated Cypermethrin Made According to Example 24

The effect of a WG formulation of cypermethrin prepared according to Example 24 on lepidopteran species was compared to a commercial cypermethrin formulation (AMMO). 4 cm leaf disks were cut from leaves of organically grown cabbage plants and were inoculated with a solution containing varying concentrations of the WG formulation. The inoculating solution was prepared by first dispersing a known amount of the WG formulation (to make 0.5 and 0.1 ppm solutions of active ingredient) in half the amount of required water. Once the WG formulation had been totally dispersed, the solution was diluted to its final volume with 1% non-ionic surfactant (NIS) solution (Induce, Helena Chemical Company). Final NIS concentration in the inoculating solution was 0.5% by weight. Each leaf disk was dipped in the inoculating solution for approximately 20 seconds and was placed in a Pall 45 mm×9 mm tight fitting lid Petri dish. A 40 mm filter paper disk moistened with 0.1 ml of distilled water was placed in the bottom of each replicate to aid in plant tissue preservation. Ten (10) cabbage loopers, 2nd instar, were placed in each dish, 2 dishes equal one replicate. Replicates were placed in a research laboratory. Environmental conditions averaged 69 F-75 F with 12-hours of light daily. Evaluations were made 48-hours following infestation for dead cabbage loopers (reported as % mortality). Efficacy of the WG formulation was tested in the field on cabbage plants and generated similar results.

Table 30 summarizes the effect of these cypermethrin formulations on cabbage loopers.

TABLE 30

Cypermethrin formulation efficacy against cabbage loopers

| Treatment Type | (Concentration) % Mortality |
|---|---|
| WG formulation of cypermethrin prepared according to Example 24 | (0.5 ppm) 100 |
| | (0.1 ppm) 90 |
| AMMO | (0.5 ppm) 35 |
| | (0.1 ppm) 5 |
| Untreated control | (0 ppm) 0 |

Example 47: Lab Scale Trial to Demonstrate Efficacy of a WG Formulation of Nanoparticles or Aggregates of Nanoparticles of Polymer-Associated Cypermethrin Made According to Example 22

The effect of a WG formulation of cypermethrin prepared according to Example 22 on lepidopteran species was compared to a commercial cypermethrin formulation (AMMO). 4 cm leaf disks were cut from leaves of organically grown cabbage plants and were inoculated with a solution containing varying concentrations of the WG formulation. The inoculating solution was prepared by first dispersing a known amount of the WG formulation (to make 1, 0.5 and 0.1 ppm solutions of active ingredient) in half the amount of required water. Once the WG formulation had been totally dispersed, the solution was diluted to its final volume with 1% non-ionic surfactant (NIS) solution (Induce, Helena Chemical Company). Final NIS concentration in the inoculating solution was 0.5% by weight. Each leaf disk was dipped in the inoculating solution for approximately 20 seconds and was placed in a Pall 45 mm×9 mm tight fitting lid Petri dish. A 40 mm filter paper disk moistened with 0.1 ml of distilled water was placed in the bottom of each replicate to aid in plant tissue preservation. Ten (10) cabbage loopers, 2nd instar, were placed in each dish, 2 dishes equal one replicate. Replicates were placed in a research laboratory. Environmental conditions averaged 69 F-75 F with 12-hours of light daily. Evaluations were made 48-hours following infestation for dead cabbage loopers (reported as % mortality).

Table 31 summarizes the effect of these cypermethrin formulations on cabbage loopers.

TABLE 31

Efficacy of cypermethrin formulations against cabbage loopers

| Treatment Type | (Concentration) % Mortality |
|---|---|
| WG formulation of cypermethrin prepared according to Example 22 | (1.0 ppm) 100 (0.5 ppm) 95 (0.1 ppm) 90 |
| AMMO | (1.00 ppm) 100 (0.5 ppm) 85 (0.1 ppm) 30 |
| Untreated control | (0 ppm) 0 |

Example 48: Field to Lab Determination of Root Uptake of WG Formulations of Nanoparticles or Aggregates of Nanoparticles of Polymer-Associated Lambda Cyhalothrin Made According to Example 21

The root uptake of WG formulations of lambda cyhalothrin prepared according to Example 21 was compared to a commercial formulation (KARATE WITH ZEON). Cabbage plants were obtained from a local nursery and were transplanted into 4-inch containers filled with silt loam soil. One plant equals one replicate. Replicate plants were placed in Zone 3 of a research greenhouse on a wire-mesh raised bench and arranged in a randomized complete block design. The research greenhouse was monitored by Procom, Micro Grow Greenhouse System temperature control system. Environmental conditions averaged high temperature 87 F to low temperature of 72 F during trial dates. Average humidity levels ranged from 40% to 75%. Replicates received natural lighting for the duration of the trial. Water was monitored for one week prior to inoculation; plants received 50 ml of water daily. Prior to inoculation, each plant received 20 ml of water to moisten the soil.

Inoculating solutions were tank mixed according to rate specifications: briefly, a known amount of the WG formulation (to obtain 18 g active ingredient/hectare) was first fully dispersed in half the required volume of water, then was diluted to the final volume with 1% non-ionic surfactant (NIS) solution (Induce, Helena Chemical Company). 20 ml of this inoculating solution was dispersed onto the soil surface. No leaching of solution resulted following application. Solutions containing the commercial formulation were also prepared with the same use rate and NIS. 48-hours following application, 2 leaf disks, 47 mm each, were cut from the upper first true leaves of the plant. One leaf disk was placed into a 9×50 mm Petri dish labeled with replicate subsample identification. Each Petri dish contained a 47 mm filter paper moistened with 0.125 ml of water to add in leaf tissue preservation. Gloves were changed and punch was cleaned between each subsample cut to prevent cross contamination. Ten (10) cabbage loopers, 2nd instar, were placed into each petri dish. Two petri dishes equal one replicate. Evaluations were made 48-hours after infestation. Ratings were taken on live, knockdown and dead cabbage loopers in each subsample.

Table 32 summarizes the root uptake of these lambda cyhalothrin formulations.

TABLE 32

Root uptake of lambda cyhalothrin formulations

| Treatment Type | % Mortality |
|---|---|
| WG formulation as described in Example 20 | 97.5 |
| KARATE WITH ZEON | 86.3 |
| Untreated control | 15.1 |

Example 49: Leaf Dip Bioassay to Test for Rainfastness of Bifenthrin Formulations Prepared According to Example 4

The rainfastness of a WG formulation of bifenthrin prepared according to Example 4 was compared to a commercial bifenthrin formulation (TALSTAR). 4 cm leaf disks were cut from leaves of organically grown cabbage plants and were inoculated with a solution containing varying concentrations of the WG formulation. The inoculating solution was prepared by first dispersing a known amount of the WG formulation (to make 1, 0.5 and 0.1 ppm solutions of active ingredient) in half the amount of required water. Once the WG formulation had been totally dispersed, the solution was diluted to its final volume with 1% non-ionic surfactant (NIS) solution (Induce, Helena Chemical Company). Final NIS concentration in the inoculating solution was 0.5% by weight. Each leaf disk was dipped in the inoculating solution for approximately 5 seconds, was allowed to air dry for 2 hours (no Rain). To test for rainfastness, some of the inoculated leaves were then dipped in deionized water for 5 seconds, and were allowed to air dry for 2 more hours (Rain). Each inoculated leaf (Rain and no Rain) was then placed in a Pall 45 mm×9 mm tight fitting lid Petri dish. A 40 mm filter paper disk moistened with 0.1 ml of distilled water was placed in the bottom of each replicate to aid in plant tissue preservation. Four (4) cabbage loopers, 2nd instar, were placed in each dish, 2 dishes equal one replicate. Replicates were placed in a research laboratory. Environmental conditions averaged 69 F-75 F with 12-hours of light daily. Evaluations were made 48-hours following infestation for dead cabbage loopers (reported as % mortality).

Table 33 demonstrates rainfastness of these bifenthrin formulations.

TABLE 33

Mortality results of several bifenthrin concentrations from various formulations under "rain" and "no-rain" conditions.

| Treatment Type | Active Concentration and Application conditions | % Mortality |
|---|---|---|
| WG formulation of bifenthrin prepared according to Example 4 | (1.00 ppm, Rain) | 80 |
| | (1.00 ppm, no Rain) | 76.9 |
| | (0.5 ppm, Rain) | 42 |
| | (0.5 ppm, no Rain) | 32 |
| | (0.1 ppm, Rain) | 12 |
| | (0.1 ppm, no Rain) | 12 |
| TALSTAR | (1.00 ppm, Rain) | 58 |
| | (1.00 ppm, no Rain) | 53 |
| | (0.5 ppm, Rain) | 21 |
| | (0.5 ppm, no Rain) | 26 |
| | (0.1 ppm, Rain) | 8 |
| | (0.1 ppm, no Rain) | 8 |
| Untreated control | (Rain) | 3.8 |
| | (no Rain) | 16 |

Example 50: High-Salt Stability/Compatibility of Bifenthrin Formulations Prepared According to Example 4

140 mg of a solid formulation of bifenthrin prepared according to Example 4 was dispersed in 140 mL tap water. To this, 50 mL of a high salt, concentrated fertilizer ((composition (10-34-0 fertilizer at 11.71b/gal (sp. gr. 1.403 g/L)) was added. A milky solution was formed immediately after mixing, and no settling of flocks was observed within a three hour period. A commercially available WP Bifenthrin formulation (Brigade) was treated the same way and was also mixed with the same a high salt, concentrated fertilizer composition. A milky solution was formed and settling of flocks was observed within 10 minutes. The stability of a HSLS formulation of bifenthrin of the present disclosure under high salt conditions was also tested. Upon mixing a dispersion prepared from an HSLS with the high salt, concentrated fertilizer as described above, no settling of flocks was observed within a three hour period.

Example 51: Formation of a Solid Formulation of Nanoparticles or Aggregates of Nanoparticles of Polymer-Associated Lambda Cyhalothrin from an Aqueous Dispersion Containing Phosphate Buffered Saline (PBS)

300 mg of polymer nanoparticles derived from poly(methacrylic acid (MAA)-co-ethyl acrylate (EA)) (MAA:EA=90:10) was made according to the procedure outlined in Example 1. The solid was dispersed in 15 mL technical grade methanol in a 50 mL glass beaker until a clear solution was formed, and was then filtered through coarse filter paper to remove any undispersed solids. 300 mg of technical grade lambda-cyhalothrin was then added to the filtered dispersion. The resulting solution was clear, and was stirred at 500 rpm using a magnetic stir bar on a stirrer hot plate for one hour. 1 L of PBS buffer (Invitrogen, 1×, pH 7.4 which contains: 137 mM NaCl; 2.7 mM KCl; 10 mM $Na_2HPO_4$; 2 mM $KH_2PO_4$) was then placed in a 2 L glass beaker and was stirred at 500 rpm using an overhead mixer. The methanol solution containing the nanoparticles and lambda cyhalothrin was then slowly fed into the stirred buffer at a rate of ~1-2 mL/min using a peristaltic pump. The feeding tube was submerged under the buffer during the entire addition process. After all the methanol has been added, the resulting milky solution was then left to mix for another 20 minutes. The solution was then concentrated by removing water/solvent using a rotary evaporator to about ½ its initial volume. The concentrated solution was then freeze dried to obtain a solid formulation of lambda cyhalothrin. The solid was redispersible in water at a concentration of ~200 ppm active ingredient. A volume average DLS particles size of ~300 nm was measured for the solid re-dispersed in deionized water at 400 ppm total solids in the measured dispersion.

Example 52: High-Salt Stability/Compatibility of a Lambda Cyhalothrin Formulation Prepared According to Example 2

The compatibility/dispersibility of a lambda cyhalothrin formulation prepared according to Example 2 was tested in CIPAC (Collaborative International Pesticides Analytical Council) standard water G (8000 ppm hardness, pH 7.0-7.0, $Mg^{2+}$ only). CIPAC standard water G was prepared according to MT 18 in CIPAC handbook F, p 59. To prepare a 200 ppm lambda cyhalothrin solution, 8-10 mg of the solid formulation prepared according to Example 2 was placed in a 20 mL scintillation vial. To this, 20 mL of CIPAC standard water G was added. After the addition of liquid, the solid formulation was allowed to wet for a few minutes, then the vial was covered and tipped 20 times to fully disperse the formulation. A milky solution was formed immediately after mixing, and no settling of flocks was observed within a three hour period.

Example 53—Demonstration of Unexpectedly Incompatible Formulation Components An HSLS of Bifenthrin was prepared according to the procedure outlined in Example 30, except using 1 g of Reax88B was (wetter, sodium lignosulfonate) employed in place of adding 1 g of Morwet D-425 (wetter, sodium salt of naphthalene sulfonate condensate). After milling, as described above, clear separation of the HSLS was observed. The separation of the HSLS was not expected since the only component that was changed was the wetter, both of which components have similar functional groups (sulfonates).

Example 54 Trial to Demonstrate the Recovery of Pre-Formed Polymer Nanoparticles from Nanoparticles or Aggregates of Nanoparticles of Polymer-Associated Active Ingredient The following experiment was performed to demonstrate that pre-formed polymer nanoparticles that have been associated with active ingredient to generate nanoparticles or aggregates of nanoparticles of polymer associated active ingredient can be recovered after extraction of the active ingredient. For the purposes of the following example, DLS results are reported as measured size followed by (% volume in brackets). DLS particle size was measured using a Malvern Zetasizer ZS.

Polymer nanoparticles derived from poly(MAA-co-EA) (MAA:EA=90:10 by mass) were prepared according to the procedure outlined in Example 1. The measured DLS volume particle size of a dispersion (1 mg/mL solids in CIPAC D water) of these polymer nanoparticles was found to be 5 nm (99.7%). A dry powder formulation was prepared by mixing 14 g of dried polymer nanoparticles and 14 g of technical grade bifenthrin in 500 mL technical grade methanol. The mixture was then stirred for 24 hours at 500 rpm and then spray dried in a Buchi Mini Spray Dryer B290 (Inlet Temperature of 220° C., aspirator gas flow rate of approximately 35 $m^3$/h, feed rate of approximately 7 mL/min, air flow 601 L/hr) to obtain a solid formulation of nanoparticles or aggregates of nanoparticles of polymer-associated bifenthrin. This solid formulation was dispersible in CIPAC D water and gave a DLS Volume particle size distribution of 90 nm (70%) and 500 nm (30%).

To determine whether preformed polymer nanoparticles retain their initial characteristics (e.g. size), after having been associated with active ingredient, the active ingredient was extracted with acetonitrile (the polymer nanoparticles themselves are insoluble in acetonitrile, while bifenthrin is highly soluble). 100 mg of the dry formulation was added to a 20 ml vial and mixed with 15 mL technical grade acetonitrile. The cloudy mixture was stirred for 4 days. The insoluble fraction was separated by centrifugation at 14.5 (×1000) rpm. The pellet (residue) was then was then washed with acetonitrile two more times to ensure that all of the bifenthrin had been removed. The washed residue was then air dried for 18 hours then re-dispersed in CIPAC D water at a concentration of 1 mg/mL. A DLS volume particle size distribution of 4 nm (99.9%) was measured for this dispersed sample. This result demonstrates that that the polymer nanoparticles retain their small particle size and water dispensability after being incorporated into a dry formulation.

Example 55: Lab Scale Trial to Demonstrate Efficacy of Formulations of Nanoparticles or Aggregates of Nanoparticles of Polymer Associated Bifenthrin Prepared According to the Current Disclosure Against Lygus Bugs The toxicity of formulations of bifenthrin prepared according to Example 5 (solid powder) and Example 16 (HSLS formulation) is compared to a commercially available bifenthrin emulsion concentrate (EC) formulation. Briefly, inoculating solutions are prepared by first dispersing a known amount of the formulation (to make final inoculating solutions of active ingredient at 0.1, 1, 10, 50, 100, 200, 300 and 500 ppm) in half the required volume of water with 20% by volume Billy Bee honey. Once the formulation is completely dispersed, the solution is diluted to its final volume with an aqueous solution containing non-ionic surfactant (NIS) solution (Tween 20, Sigma). The final NIS concentration in the inoculating solution is 0.5% by volume, and the final concentration of honey is 10% by volume.

For each trial, 0.5 mL of the inoculating solution is added to a floral foam substrate and allowed to absorb into the substrate. The foam is placed into a vial followed by one *Lygus lineolaris* specimen and the vial is capped with cotton. Five to ten repetitions of each formulation are used, each having one bug per vial. Vials are then maintained at room temperature (~21±2° C.), in a 18:6 hour light:dark cycle. Evaluations of dead *L. lineolarisare* made 24, 48 and 72 hours following introduction of the bugs to the foam (reported as % mortality). The formulations of bifenthrin prepared according to current disclosure show comparable or enhanced performance compared to the commercial bifenthrin formulations.

Example 56: Lab Scale Trial to Demonstrate Efficacy of Formulations of Nanoparticles or Aggregates of Nanoparticles of Polymer Associated Bifenthrin Prepared According to the Current Disclosure Against Mites The toxicity of formulations of bifenthrin prepared according to Example 5 (solid powder) and Example 16 (HSLS formulation) is compared to a commercially available bifenthrin emulsion concentrate (EC) formulation. Briefly, inoculating solutions are prepared by first dispersing a known amount of the formulation (to make final inoculating solutions of active ingredient at 0.1, 1, 10, 50, 100, 200, 300 and 500 ppm) in half the required volume of water. Once the formulation has been completely dispersed, the inoculating solution is diluted to its final volume with an aqueous solution containing non-ionic surfactant (NIS) solution (Tween 20, Sigma). The final NIS concentration in the inoculating solution is 0.5% by volume.

For each treatment, a freshly cut 5 cm circle of green bean (*Phaseolus vulgaris*) leaf is submerged for 5 seconds in each solution (one leaf is equivalent to one repetition; one to three repetitions are used). The leaves are then left to dry thoroughly on a drying rack. Deli containers (125 mL) are used to contain the mites by creating 'mite islands'. Sponge circles roughly 1.5 inches high, 5-6 cm in diameter are glued to the bottom of the deli containers. Reverse osmosis treated water is then added to the dishes until the water level is roughly 1 inch high, thereby saturating the sponge. Once the leaf disks are dry, they are transferred ventral side up onto the damp sponges. One leaf is placed in each deli container. Using a dissecting scope and a probe, ten adult two-spotted spider mites (*Tetranychus urticae*) are removed from a colony and added to the treated leaf disk. The containers (without lids) are placed in an incubator maintained at 25±1° C. with a 18:6 hour light:dark cycle.

Evaluations of dead *T. urticae* are made 48 hours following introduction to the leaf disk (reported as % mortality). The formulations of bifenthrin prepared according to the current disclosure show comparable or enhanced performance compared to the commercial bifenthrin formulations.

Example 57 Lab Scale Demonstration of Improvement of Soil Mobility Characteristics of an Active Ingredient Using a HSLS Formulation Prepared According to the Current Disclosure The following static soil binding experiment was performed to investigate the soil mobility characteristics of formulations prepared according to the current disclosure compared to those of commercially available formulations. It should be noted that soil mobility is related to soil binding and adsorption, and that formulations that reduce or prevent the binding or adsorption of active ingredients to soil can impart enhanced soil mobility properties to the active.

A HSLS containing ~18% bifenthrin formulation was prepared according to Example 33, but using a 2:1 ratio of polymer nanoparticles to bifenthrin. This formulation was tested against a commercial bifenthrin formulation (Brigade® 2EC) to determine their soil adsorption characteristics. Briefly, 2 g of air dried soil (silt loam texture, total carbon 2.45%) was equilibrated with 45.0 mL 0.01M $CaCl_2$ solution for 12 hours. This was done by placing the soil and the solution in a 100 mL Nalgene bottle, and agitating it on an orbital shaker for 12 hours. After equilibration, 5 mL of a 200 ppm active solution (made by dispersing the formulations in 0.01M $CaCl_2$) was added and the resulting mixture was agitated on an orbital shaker for another 24 hours. The mixture was then transferred to a 50 mL centrifuge tube and was spun at 900 rpm for 3 minutes. 2 mL of the supernatant was then analyzed for active content by extracting bifenthrin with hexanes. The amount of extracted active was determined by HPLC analysis. Tabulated results showing % active ingredient lost after being exposed to soil are shown in the Table below:

TABLE 34

Amount of initial bifenthrin in solution and amount of bifenthrin lost after solution containing formulations were exposed to soil

| Bifenthrin Formulation | Starting Bifenthrin Concentration(ppm) | % Bifenthrin lost after being exposed to soil |
| --- | --- | --- |
| Brigade 2EC | 198 | 98% |
| Talstar SC | 190 | 90% |
| Formulation prepared according to the current disclosure. | 190 | 26% |

The invention claimed is:

1. An aqueous formulation comprising:
   nanoparticles comprising a polymer and a pyrethroid compound with an average diameter of between about 1 nm and about 500 nm;
   wherein the polymer is a polyelectrolyte copolymer comprised of between about 50 weight percent and about 95 weight percent methacrylic acid monomers and between about 50 weight percent and about 5 weight percent ethyl acrylate or styrene monomers;
   between about 0.5 weight percent and about 5 weight percent of a naphthalene sulfonate condensate dispersant;
   between about 0.5 weight percent and about 5 weight percent of a sodium dodecylbenzene sulfonate wetting agent;
   between about 0.1 weight percent and about 1 weight percent of an anti-foaming agent;
   between about 0.01 weight percent and about 0.1 weight percent of a preservative; and
   water;
   wherein the nanoparticles comprise between about 5 weight percent and about 50 weight percent of the formulation.

2. The aqueous formulation of claim 1, wherein the pyrethroid compound comprises between about 5 weight percent and about 40 weight percent of the formulation.

3. The aqueous formulation of claim 1, wherein a ratio of a weight percent of the pyrethroid compound to a weight percent of the polymer is between about 1:1 to 5:1.

4. The aqueous formulation of claim 1; wherein the pyrethroid compound has a melting point of less than 80° C.

5. The aqueous formulation of claim 1; wherein the pyrethroid compound is selected from the group consisting of bifenthrin, gamma-cyhalothrin, lambda-cyhalothrin; cypermethrin, zeta-cypermethrin; beta-cypermethrin, esfenvalerate, fenvalerate, permethrin, resmethrin, acrinathrin, and combinations thereof.

6. The aqueous formulation of claim 1, further comprising a thickener.

7. The aqueous formulation of claim 1, further comprising an anti-freeze agent.

8. The aqueous formulation of claim 1, further comprising a fungicide.

9. The aqueous formulation of claim 1, wherein the polyelectrolyte copolymer is a poly(methacrylic acid-co-ethyl acrylate) copolymer.

10. The aqueous formulation of claim 6, wherein the thickener comprises between about 0.05 weight percent and about 5 weight percent of the formulation.

11. The aqueous formulation of claim 7, wherein the anti-freeze agent comprises between about 1 weight percent and about 10 weight percent of the formulation.

12. The aqueous formulation of claim 1, wherein the pyrethroid compound has a melting point of less than 100° C.

13. The aqueous formulation of claim 1, without a UV-blocker.

14. The aqueous formulation of claim 1, further comprising a liquid fertilizer.

15. The aqueous formulation of claim 14, wherein the fertilizer comprises at least one of the elements selected from the group consisting of: boron, copper, manganese, iron, chorine, molybdenum, zinc sulfur, nitrogen, phosphorus and potassium.

16. A method of controlling pests comprising applying the aqueous formulation of claim 1 to a plant, a soil adjacent to a plant, to soil where a seed is or will be planted.

17. The method of claim 16, wherein the pests to be controlled are members of an order selected from the group consisting of lepidoptera, diptera, Siphonaptera, ixodida, blattaria, isoptera, hymenoptera, hemiptera, coleopteran, thysanoptera and combinations thereof.

18. The method of claim 16, wherein the pests are mites.

19. The method of claim 16 wherein the pyrethroid compound is bifenthrin and is applied at a rate of between about 4 and about 37 grams of bifenthrin per hectare and the pests to be controlled are selected from the group consisting of Alfalfa Caterpillar, Aphids, Aster Leafhopper, Bean Leaf Beetle, Beet Armyworm, Cloverworm, Corn Earworm, Corn Rootworm (adult), Cucumber Beetles, Cutworms, European Corn Borer, Fall Armyworm, Flea Beetle, Grasshoppers, Imported Cabbageworm, Japanese Beetle (Adult), Leafhoppers, Leafminer, Loopers, Mexican Bean Beetle (adult), Pea Leaf Weevil, Pea Weevil, Plant Bug, Saltmarsh Caterpillar, Sap Beetle, Southern Armyworm, Stink Bugs, Tarnished Plant Bug, Thrips, Tobacco budworm, Webworms, Western Bean Cutworm, Whitefly, and Yellowstriped armyworm.

20. The method of claim 16 wherein the pyrethroid compound is lambda-cyhalothrin and is applied at a rate of about 2 and about 17 grams of lambda-cyhalothrin per hectare and the pests are selected from the group consisting of Bean Leaf Beetle, Cabbage Looper Corn Earworm, Cutworm spp., Green Cloverworm, Mexican Bean Beetle, Mexican Corn Rootworm Beetle (Adult), Northern Corn Rootworm Beetle (Adult), Painted Lady (Thistle) Caterpillar, Potato Leafhopper, Saltmarsh Caterpillar, Southern Corn Rootworm Beetle (Adult), Soybean Aphids, Three-cornered Alfalfa Hopper, Thrips, Velvetbean Caterpillar, Western Corn Rootworm Beetle (Adult), and Woollybear Caterpillar.

21. The aqueous formulation of claim 1, wherein the polyelectrolyte copolymer is a poly(methacrylic acid-co-styrene) copolymer.

22. The aqueous formulation of claim 1, wherein the polyelectrolyte copolymer is water soluble at pH 7.

23. The aqueous formulation of claim 1, wherein the polyelectrolyte copolymer has a water solubility at pH 7 of greater than 30%.

24. An aqueous formulation comprising:
   nanoparticles comprising a polymer and a pyrethroid compound with an average diameter of between about 1 nm and about 500 nm;
   wherein the polymer is a polyelectrolyte copolymer comprised of between about 75 weight percent and about 90 weight percent acrylic acid monomers and between about 25 weight percent and about 10 weight percent styrene monomers;
   between about 0.5 weight percent and about 5 weight percent of a naphthalene sulfonate condensate dispersant;
   between about 0.5 weight percent and about 5 weight percent of a sodium dodecylbenzene sulfonate wetting agent;
   between about 0.1 weight percent and about 1 weight percent of an anti-foaming agent;
   between about 0.01 weight percent and about 0.1 weight percent of a preservative; and
   water;
   wherein the nanoparticles comprise between about 5 weight % and about 50 weight % of the formulation.

* * * * *